United States Patent
Marsault et al.

(10) Patent No.: US 10,716,797 B2
(45) Date of Patent: Jul. 21, 2020

(54) STEROID ALKALOIDS AND COMPOSITIONS AND KITS THEREOF

(71) Applicant: SOCPRA SCIENCES ET GÉNIE S.E.C., Sherbrooke (CA)

(72) Inventors: Éric Marsault, Sherbrooke (CA); François Malouin, Eastman (CA); Félix Chagnon, Waterloo (CA); Isabelle Guay, Magog (CA); Simon Boulanger, Longueuil (CA)

(73) Assignee: SOCPRA SCIENCES ET GÉNIE S.E.C. (CA)

( * ) Notice: Subject to any disclaimer, the term of this patent is extended or adjusted under 35 U.S.C. 154(b) by 0 days.

(21) Appl. No.: 16/137,040

(22) Filed: Sep. 20, 2018

(65) Prior Publication Data

US 2019/0008875 A1 Jan. 10, 2019

Related U.S. Application Data

(63) Continuation of application No. 15/105,761, filed as application No. PCT/CA2014/051262 on Dec. 23, 2014, now Pat. No. 10,137,137.

(60) Provisional application No. 61/919,896, filed on Dec. 23, 2013.

(51) Int. Cl.
| | | |
|---|---|---|
| *A61K 31/58* | (2006.01) |
| *A61K 31/57* | (2006.01) |
| *C07J 41/00* | (2006.01) |
| *C07J 71/00* | (2006.01) |
| *A61K 45/06* | (2006.01) |
| *A61K 31/7036* | (2006.01) |
| *C12N 9/14* | (2006.01) |

(52) U.S. Cl.
CPC .............. *A61K 31/58* (2013.01); *A61K 31/57* (2013.01); *A61K 31/7036* (2013.01); *A61K 45/06* (2013.01); *C07J 41/005* (2013.01); *C07J 71/0005* (2013.01); *C12N 9/14* (2013.01)

(58) Field of Classification Search
CPC .... A61K 2300/00; A61K 31/57; A61K 31/58; A61K 45/06; A61K 31/7036; C07J 41/005; C07J 71/0005; C12N 9/14
USPC .......................................... 514/171; 517/171
See application file for complete search history.

(56) References Cited

U.S. PATENT DOCUMENTS

| | | | |
|---|---|---|---|
| 2,770,618 A | 11/1956 | Kuhn |
| 3,013,008 A | 12/1961 | Counsell |
| 3,419,661 A | 12/1968 | Elder |
| 3,558,608 A | 1/1971 | Klimstra |
| 7,985,422 B2 | 7/2011 | Vaya |
| 8,263,125 B2 | 9/2012 | Vaya |
| 2004/0096499 A1 | 5/2004 | Vaya |
| 2006/0024365 A1 | 2/2006 | Vaya |

FOREIGN PATENT DOCUMENTS

| | | |
|---|---|---|
| CA | 2395642 C | 7/2001 |
| CN | 101054399 A | 10/2007 |
| WO | 2001/49279 | 7/2001 |
| WO | 2012109752 | 8/2012 |

OTHER PUBLICATIONS

Quyen, L. et al. (1990) Synthesis of the Steroid Alkaloid Soladunalinidine and Other 5a¬Spirosolan-3-amines, Liebigs Ann. Chem., 1990, 6, p. 519-524.
Ragle, B.E. et al. (2010) Prevention and treatment of *Staphylococcus aureus* pneumonia with a beta-cyclodextrin derivative. Antimicrob Agents Chemother 54, 298-304.
Roddick, J.G. (1974) Steroidal glycoalkaloid alpha-tomatine. Phytochemistry 13: 9-25.
Rodrigue, S. et al. (2010) Unlocking Short Read Sequencing for Metagenomics. PLoS One 5(7): e11840. doi:10.1371/journal.pone. 0011840.
Rowan, D.D. et al. (1983) Antifungal stress metabolites from Solanum aviculare, Phytochem., 22(9), p. 2102-2104.
Ruiz-Rubio, M. et al. (2001) Metabolism of the tomato saponin alpha-tomatine by phytopathogenic fungi. In Studies in Natural Products Chemistry. vol. 25. Rahman, A. (ed). Oxford: Elsevier, pp. 293-326.
Rupnik, M. et al. (2009) Clostridium difficile infection: new developments in epidemiology and pathogenesis. Nat Rev Microbiol 7: 526-536.
Sato, Y. et al. (1956) New Dihydro Derivatives of Tomatidine and Solasodine, J. Am. Chem. Soc., 78(13), p. 3150-3153.
Sato, Y. et al. (1960) Chemistry of the Spiroaminoketal Side Chain of Solasodine and Tomatidine. IV. Chemistry of the Tomatidine Side Chain, J. Org. Chem., 25, p. 1962-1965.

(Continued)

*Primary Examiner* — Sabiha N Qazi
(74) *Attorney, Agent, or Firm* — Lavery, De Billy, LLP; Julie Gauvreau

(57) ABSTRACT

The present invention provides bacterial ATP synthase inhibitors such as a compound of formula (I):

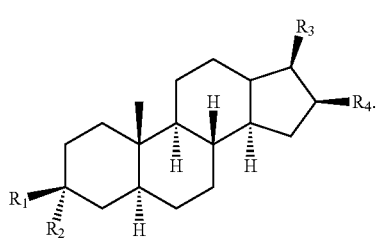

(I)

There are provided compositions and kits using such compounds and inhibitors.

11 Claims, 12 Drawing Sheets
Specification includes a Sequence Listing.

(56) References Cited

OTHER PUBLICATIONS

Sato, Y. et al. (1965) Structure of Tomatillidine, J. Org. Chem., 1965, 30(3), p. 754-760.
Sato, Y. et al. (1969) Alkaloids from Solanum congestiflorum, J. Org. Chem., 34(6), p. I 577-I582.
Schmitz, F.-J. et al. (1999). The prevalence of aminoglycoside resistance and corresponding resistance genes in clinical isolates of *staphylococci* from 19 European hospitals. J. Antimicrob. Chemother. 43 : 253-259.
Schreiber, K. et al. (1964) Synthese von 22,26-imin0-5(x-cholestan-3p-olen aus 3p-acetoxy-pregn-5-en-20-0n und deren sterische zuordnung2, Tetrahedron, 20, p. 1707-1718.
Schreiber, K. et al. (1965) Uber Tomatid-5-en-3P-ol aus *Solanum dulcamara* L. und Jessen abbau zu 3P-acetoxy-pregna-5,16-dien-20-on, Justus Liebigs Annalen der Chemie, 681, p. 187-195.
Sears, P. M. et al. (2003) Management and treatment of staphylococcal mastitis. Vet. Clin. Food Anim. Pract. 19:171-185.
Segala, E. et al. (2012) New mutations in the Mycobacterial ATP synthase: New insights into the binding of the diarylquinoline TMC207 to the ATP synthase C-ring structure. Antimicrob. Agents Chemother. 56:2326-2334.
Sendi, P. et al.(2009) *Staphylococcus aureus* as an intracellular pathogen: the role of small colony variants. Trends Microbiol 17: 54-58.
Shah, P.M. (2005) The need for new therapeutic agents: what is the pipeline? Clin Microbiol Infect 11 Suppl 3: 36-42.
Sibley, C.D. et al. (2009) The relevance of the polymicrobial nature of airway infection in the acute and chronic management of patients with cystic fibrosis. Curr Opin Investig Drugs 10: 787-794.
Sibley, C.D. et al. (2011) The polymicrobial nature of airway infections in cystic fibrosis: Cangene Gold Medal Lecture. Can J Microbiol 57: 69-77.
Simons, V. et al. (2006) Dual Effects of Plant Steroidal Alkaloids on *Saccharomyces cerevisaiae*, Antimicrob. Agents Chemother., 50, p. 2732-2740.
Songer, J. G., et al. (2005) Clostridial enteric infections in pigs. J. Vet. Diagn. Invest. 17:528-536.
Songer, J.G. (2010) Clostridia as agents of zoonotic disease. Vet Microbiol 140: 399-404.
Stepan, J. et al. (2004) Molecular diagnostics of clinically important *Staphylococci*. Folia Microbiol (Praha) 49: 353-386.
Stewart, P.S. (2002) Mechanisms of antibiotic resistance in bacterial biofilms. Int J Med Microbiol 292: 107-113.
Talbot, G.H. et al. (2006) Bad bugs need drugs: an update on the development pipeline from the Antimicrobial Availability Task Force of the Infectious Diseases Society of America. Clin Infect Dis 42: 657-668.
Tenhagen, B. A., et al. (2006). Prevalence of mastitis pathogens and their resistance against antimicrobial agents in dairy cows in Brandenburg, Germany. J Dairy Sci 89(7): 2542-51.
Tschesche, R. et al. (1978) Zur Syntheese von 22,26-Epiminocholestanolen, Chem. Ber., ///(2), p. 801-802.
Tschesche, R. et al. (1978), Zur Biogenese Des Aza-Oxa-Spiran-Systems Der Steroidalkoide Vom Spirosolan-typ in Solanaceen, Phytochem., 17(2), p. 251-255.
Tuchscherr, L. et al. (2011) *Staphylococcus aureus* phenotype switching: an effective bacterial strategy to escape host immune response and establish a chronic infection. EMBO Mol Med, 3, 1-3.
Ubuka, T. (1963) Experimental isovalthinuria. III. Induction by bile acids, and hypocholesterolemic agents, Acta Med. Okayama, 17(6), p. 273-278.
Uhle, F.C. (1961) The Synthesis pf Azaoxaspirane Steroid Alkaloids, J. Am. Chem. Soc., 83(6) , p. I460-I472.
Van Immerseel, F. et al. (2004) Clostridium perfringens in poultry: an emerging threat for animal and public health. Avian Pathol. 33:537-549.
Vergison, A. (2007) National survey of molecular epidemiology of *Staphylococcus aureus* colonization in Belgian cystic fibrosis patients. J. of Antimicrob Chemother. 59:893-899.
Vial, L., Lepine (2008) Burkholderia pseudomallei, B. thailandensis, and B. ambifaria produce 4-hydroxy-2-alkylquinoline analogues with a methyl group at the 3 position that is required for quorum-sensing regulation. J Bacteriol 190: 5339-5352.
Voggu, L. (2006) Microevolution of cytochrome bd oxidase in *Staphylococci* and its implication in resistance to respiratory toxins released by Pseudomonas. J Bacteriol 188: 8079-8086.
Vuong, C. et al. (2002) *Staphylococcus epidermidis* infections. Microbes Infect 4: 481-489.
Wellinghausen, N. et al. (2009) Characterization of clinical Enterococcus faecalis small-colony variants. J Clin Microbiol 47: 2802-2811.
Wikler, M.A. (2016) Methods for Dilution Antimicrobial Susceptibility Tests for Bacteria That Grow Aerobically; Approved Standard—Seventh Edition, Clinical ans Laboratory Standards Institute, 26(2), p. 1 and 49.
Wilson, S.G. et al. (1976) Selection and characterization of strains of *Staphylococcus aureus* displaying unusual resistance to aminoglycosides. Antimicrob Agents Chemother 10: 519-525.
Witte, W. et al. (2008) Emergence and spread of antibiotic-resistant Gram-positive bacterial pathogens. Int J Med Microbiol 298: 365-377.
Wolter, D.J. et al. (2013) *Staphylococcus aureus* small-colony variants are independently associated with worse lung disease in children with cystic fibrosis. Clin Infect Dis. 57(3):384-91. doi: 10.1093/cid/cit270. Epub Apr. 26.
Wong, W. C. et al. (1995) A Concise Synthesis of Atipamezole Synthesis, p. 139-141.
Xie, W. (2001) Structure-activity relationship of Aza-steroids as PI-PLC inhibitors, Bioorganic & Medicinal Chemistry, 9, 1073-1083.
Zha, X. et al. (2010) Synthesis and in vitro antitumor activities of novel soladulcidine derivatives, Zhongguo Yaoke Daxue Xuebao (Journal of China Pharmaceutical University), 41(6), p. 493-498.
U.S. Appl. No. 13/984,991 to Malouin et al., Non final rejection dated Jun. 10, 2015.
U.S. Appl. No. 13/984,991 to Malouin et al., Restriction requirement dated Jun. 25, 2014.
U.S. Appl. No. 13/984,991 to Malouin et al., Restriction requirement dated Dec. 2, 2014.
EP12747258.7 to Malouin et al., EPO Communication 161(2) & 162 dated Oct. 9, 2013.
PCT/CA2012050087 to Malouin et al., IPRP dated Aug. 21, 2013.
PCT/CA2014051262 to Malouin et al., IPRP dated Jul. 7, 2016.
PCT/CA2012050087 to Malouin et al., ISR/WO dated May 3, 2012.
PCT/CA2014051262 to Malouin et al., ISR/WO dated Mar. 10, 2015.
Chagnon et al. (2014) Unraveling the structure-activity relationship of tomatidine, a steroid alkaloid with unique antibiotic properties against persistent forms of *Staphylococcus aureus*, European Journal of Medicinal Chemistry 80: 605-620.
Extended European Search Report issued in EP14873837.0 dated Dec. 15, 2017.
Restriction Requirement issued in U.S. Appl. No. 15/105,761 dated May 2, 2017.
Office Action issued in U.S. Appl. No. 15/105,761 dated Oct. 27, 2017.
Notice of Allowance ssued in U.S. Appl. No. 15/105,761 dated Jun. 22, 2018.
Adam, G. et al. (1963) Solanum-Alkaloide XXVI. Preparative Trennung stereoisomerer lmino-choelstane and weiterer Steroide <lurch Dilnnschicht-Chromatographie unter Verwendung von Jod als indifferentes Nachweisreagens, Z. Chem., 3(3), p. 100-102.
Adam, G. et al. (1964) Solanum-Alkaloide XXXIX. Synthese von 22,26-imino-5a¬icholestan-3P-olen aus 3P-acetoxy-pregn-5-en-20-on und deren sterische zuordnung, Tetrahedron, 20(1), p. 1707-1718.
Alexander, E.H. et al. (2001) Factors influencing the internalization of *Staphylococcus aureus* and impacts on the course of infections in humans. Appl Microbiol Biotechnol 56: 361-366.
Allegrucci, M. et al. (2008) Formation of *Streptococcus pneumoniae* non-phase-variable colony variants is due to increased mutation frequency present under biofilm growth conditions. J Bacteriol 190: 6330-6339.

(56) References Cited

OTHER PUBLICATIONS

Andries K. et al. (2005) A Diarylquinoline Drug Active on the ATP Synthase of Mycobacterium tuberculosis. Science, 307: 223-227.
Archer, G.L. (1998) *Staphylococcus aureus*: a well-armed pathogen. Clin Infect Dis 26: 1179-1181.
Armas, P. et al. (1988) Steroidal N-Nitrosoamines. Part 4. Intramolecular Functionalization of N-Nitroamine Radicals: Synthesis of 1,4-Nitroimine Compounds, J. Chem. Soc. Perkin Trans. I, 1988, 12, p. 3255-3265.
Atalla, H. et al. (2008) Characterization of a *Staphylococcus aureus* small colony variant (SCV) associated with persistent bovine mastitis. Foodborne Pathog Dis 5: 785-799.
Avni, T. et al. (2010) Prophylactic antibiotics for burns patients: systematic review and meta-analysis. BMJ 2010;340: c241 doi: 10.1136/bmj.c241.
Ayesa, S. (2009) Solid-phase parallel synthesis and SAR of 4-amidofuran-3-one inhibitors of cathepsin S: effect of sulfonamides P3 substituents on potency and selectivity. Bioorg Med Chem, 17, 1307-24.
Bad Bug Book (2012) *Bacillus cereus* and other *Bacillus* spp. Foodborne Pathogenic Microorganisms and Natural Toxins Handbook. Food and Drug Administration (www.fda.gov).
Balemans, W. et al. (2012) Novel Antibiotics Targeting Respiratory ATP Synthesis in Gram-Positive Pathogenic Bacteria Antimicrob. Agents Chemother. 56: 4131-4139.
Bednarek, P. et al. (2009) Plant-microbe interactions: chemical diversity in plant defense. Science 324: 746-748.
Beierlein, J.M. et al. (2011) New developments in vaccines, inhibitors of anthrax toxins, and antibiotic therapeutics for Bacillus anthracis. Curr Med Chem. 18(33):5083-94.
Bird, G.J. et al. (1978) Soladunalinidine, a new steroidal alkaloid from Solanum dunalianum, Tett. Lett., 2, p. I 59-160.
Bird, G.J. et al. (1979) Structures of the Steroidal Alkaloids 25-Isosolaforidine and Solacallinidine Isolated from Solanum cal/ium, Aust. J. Chem., 32(3), p. 597-609.
Black, J.G. (2008) Microbiology: Principles and Explorations 7th ed. John Wiley & Sons.
Bolger, M.B. et al. (2007) In vitro and in vivo activity of 16,17-dehydro-epipregnanolones: 17,20-bond torsional energy analysis and D-ring conformation. Pharm Res 1996, 13, 1488-94.
Brouillette, E. (2004) Persistence of a *Staphylococcus aureus* small-colony variant under antibiotic pressure in vivo. FEMS Immunol Med Microbiol 41: 35-41.
Brouillette, E. et al. (2004b). Mouse mastitis model of infection for antimicrobial compound efficacy studies against intracellular and extracellular forms of *Staphylococcus aureus*. Vet. Microbiol. 101:253-262.
Bryan, L.E. et al. (1981) Mechanisms of aminoglycoside resistance of anaerobic bacteria and facultative bacteria grown anaerobically. J Antimicrob Chemother 8 Suppl D: 1-8.
Canadian Cystic Fibrosis Foundation (2007) Patient data registry report. Toronto, ON, Canada.
Casey, A.L., Lambert, P.A., and Elliott, T.S. (2007) *Staphylococci*. Int J Antimicrob Agents 29 Suppl 3: S23-32.
Ceri, H. et al. (1999) The Calgary Biofilm Device: new technology for rapid determination of antibiotic susceptibilities of bacterial biofilms. J Clin Microbiol 37(6): 1771-6.
Chambers, H.F. et al. (2009) Waves of resistance: *Staphylococcus aureus* in the antibiotic era. Nat Rev Microbiol 7: 629-641.
Chastre, J. et al. (2002) Ventilator-associated pneumonia. Am J Respir Crit Care Med 165: 867-903.
Chatterjee, I. et al. (2007) Enhanced post-stationary-phase survival of a clinical thymidine-dependent small-colony variant of *Staphylococcus aureus* results from lack of a functional tricarboxylic acid cycle. J Bacteriol 189: 2936-2940.
Clinical and Laboratory Standards Institute (CLSI) (2006) Methods for dilution antimicrobial susceptibility tests for bacteria: Approved Standard.
Coleman et al. (2010) Characterization of Plant-Derived Saponin Natural Products against Candida albicans, ACS Chem. Biol., 5(3), p. 321-332. See compounds Al 1 and A20.
Costerton, J.W. et al. (1999). Bacterial biofilms: a common cause of persistent infections. Science 284: 1318-1322.
Cystic Fibrosis Foundation (2008) Patient registry annual report. Washington, D.C.
Dasenbrook, E.C. et al. (2010) Association between respiratory tract methicillin-resistant *Staphylococcus aureus* and survival in cystic fibrosis. Jama 303: 2386-2392.
Davies D. (2003) Understanding biofilm resistance to antibacterial agents. Nat Rev Drug Discov 2: 114-122.
Davis, BD. (1982) Bactericidal synergism between beta-lactams and aminoglycosides: mechanism and possible therapeutic implications. Rev Infect Dis. 4(2):237-245.
Deslouches, B. et al. (2005) Activity of the De Novo Engineered Antimicrobial Peptide WLBU2 against Pseudomonas aeruginosa in Human Serum and Whole Blood: Implications for Systemic Applications. Antimicrob. Agents chemother. 49: 3208-3216.
Eliopoulos, G.M et al. (1996) Antimicrobial combinations. In Antibiotics in Laboratory Medicine, 4th ed. (V. Lorian, Ed.), pp. 330-396. Williams and Wilkins, Baltimore, MD.
Friedman, M. (2002) Tomato glycoalkaloids: role in the plant and in the diet. J Agric Food Chem 50: 5751-5780.
Galli, J. et al. (2007) Recurrent upper airway infections and bacterial biofilms. J Laryngol Otol 121: 341-344.
Gibson, R.L. et al. (2003) Pathophysiology and management of pulmonary infections in cystic fibrosis. Am J Respir Crit Care Med 168: 918-951.
Ginnes, R. B. et al. (1996) Respiration. In *Escherichia coli* and *Salmonella*, cellular and molecular biology, p. 217-261. Ed. F. C. Neidhardt. American Society for Microbiology, Washington.
Goerke, C. et al. (2004) Regulatory and genomic plasticity of *Staphylococcus aureus* during persistent colonization and infection. Int J Med Microbiol 294: 195-202.
Goldberg, J.B. et al. (1995) Avirulence of a Pseudomonas aeruginosa algC Mutant in a Burned-Mouse Model of Infection. Infect. Immun. 63: 4166-4169.
Gonzalez-Lamothe, R. et al. (2009) Plant antimicrobial agents and their effects on plant and human pathogens. Int J Mol Sci 10: 3400-3419.
Guillet, C., O. et al. (2010) Human Listeriosis Caused by Listeria ivanovii. Emerging Infectious Diseases, 16:136-138.
Hamon, M.A. et al. (2012) Listeriolysin O: the Swiss army knife of Listeria. Trends Microbiol., Aug;20(8):360-368.
Harlid, R., Andersson, G., Frostell, C.G., Jorbeck, H.J., and Ortqvist, A.B. (1996) Respiratory tract colonization and infection in patients with chronic tracheostomy. A one-year study in patients living at home. Am J Respir Crit Care Med 154: 124-129.
Harrison, F. (2007) Microbial ecology of the cystic fibrosis lung. Microbiology 153: 917-923.
Hecht, D.W. (2006) Anaerobes: antibiotic resistance, clinical significance, and the role of susceptibility testing. Anaerobe 12: 115-121.
Hoffman, L.R. et al. (2006) Selection for *Staphylococcus aureus* small-colony variants due to growth in the presence of Pseudomonas aeruginosa. Proc Natl Acad Sci U S A 103: 19890-19895.
Hong, S. et al. (2008) ATP Synthase and the Actions of Inhibitors Utilized to Study Its Roles in Human Health, Disease, and Other Scientific Areas. Microbiol. Mol. Biol. Rev. 72:590-641.
Hubert D. et al. (2012) Association between *Staphylococcus aureus* alone or combined with Pseudomonas aeruginosa and the clinical condition of patients with cystic fibrosis. J. Cystic Fibrosis. Publish ahead of print 2012.
Jacques, M. et al. (2010) Biofilm formation in bacterial pathogens of veterinary importance. Anim Health Res Rev 11: 97-121.
Jensen K.B. et al. (2002) Synthesis of Guanidinium-Derived Receptor Libraries and Screening for Selective Peptide Receptors in Water, Chemistry—A European Journal, 8:1300-1309.
Kessler, E. et al. (1993) Secreted LasA of Pseudomonas aeruginosa is a staphylolytic protease. J Biol Chem 268: 7503-7508.

(56) References Cited

OTHER PUBLICATIONS

Kircher, H.W. et al. (1982) Preparation of Some Unsaturated Side-Chain Derivatives of Cholesterol, J. Org. Chem., 47 (9), p. I 722-1724.
Kloos, W.E. et al. (1994) Update on clinical significance of coagulase-negative Staphylococci. Clin Microbiol Rev 7: 117-140.
Kraml, M. et al. (1967) Agents Affecting Lipid Metabolism. XXVI. Specificity of Some Inhibitors of the Late Stages of Cholesterol Biosynthesis, Lipids, 2(1), p. 5-7.
Kusano, G. et al. (1987) Antifungal Properties ofSolanum Alkaloids, Chem. Pharm. Bull., 35(12), p. 4862-4867.
Lavie, Y. et al. (2001) Inhibitory Effect of Steroidal Alkaloids on Drug Transport and Multidrug Resistance in Human Cancer Cells, Anticancer Res., 2/(2A), p. 1189-1194.
Li, W. et al.(2009) Expeditious synthesis of hippuristanol and congeners with potent antiproliferative activities. Chemistry, 15, 10356-9.
Li, W. et al. (2009) Fast and accurate short read alignment with Burrows-Wheeler Transform. Bioinformatics, 25:1754-60. [PMID: 19451168].
Lightbown, J.W. et al. (1956) Inhibition of cytochrome systems of heart muscle and certain bacteria by the antagonists of dihydrostreptomycin: 2-alkyl-4-hydroxyquinoline N-oxides. Biochem J 63: 130-137.
Lyczak, J.B. et al. (2002) Lung infections associated with cystic fibrosis. Clin Microbiol Rev 15: 194-222.
Machan, Z.A. et al. (1992) 2-Heptyl-4-hydroxyquinoline N-oxide, an antistaphylococcal agent produced by Pseudomonas aeruginosa. J Antimicrob Chemother 30: 615-623.
Malouin, F. et al. (2005) Identification of antimicrobial compounds active against intracellular Staphylococcus aureus. FEMS Immunol. Med. Microbiol. 45:245-252.
Malouin, F. et al.(2011) Tomatidine Inhibits Replication of Staphylococcus aureus Small Colony Variants in Cystic Fibrosis Airway Epithelial Cells, Antimicrob. Agents Chemother., 55, p. I937-1945.
Malouin, F. et al. (2012) Tomatidine acts in synergy with aminoglycoside antibiotics against multiresistant Staphylococcus aureus and prevents virulence gene expression, J. Antimicrob. Chemother., 67, p. 559-568.
Martin-Hernandez, A.M. et al. (2000) Effects of targeted replacement of the tomatinase gene on the interaction of Septoria lycopersici with tomato plants. Mol Plant Microbe Interact 13: 1301-1311.
Mates, S. M. et al. (1983) Membrane potential in anaerobically growing Staphylococcus aureus and its relationship to gentamicin uptake. Antimicrob. Agents Chemother. 23:526-530.
Maxwell, A. et al. (1995) 3?-aminospirolane steroidal alkaloids from so/anum triste, J. Nat. Prod, 58(4), p. 625-628.
Maxwell, A. et al. (1996) 3-Aminospirolane alkaloids from solanum arboreum, Phytochemistry, 43(4), p. 913-915.
Mazur, Y. et al. (1960) The Synthesis of the Steroidal Sapogenins, J. Am. Chem. Soc., 82(22), p. 5889-5908.
Mckenna, J. (1953) Steroidal Alkaloids, Quarterly Reviews, Chemical Society, 7(3), p. 23 I-254.
McVay, C.S. et al. (2007) Phage Therapy of Pseudomonas aeruginosa Infection in a Mouse Bum Wound Model. Antimicrob. Agents Chemother. 51:1934-1938.
Mead, P.S. et al. (1999) Food-related illness and death in the United States. Emerg Infect Dis 5: 607-625.
Meccia, G. et al. (1987) On the Configuration of Solaquidine, J. Nat. Prod., 50(4), p. 642-645.
Melter, O. et al. (2010) Small colony variants of Staphylococcus aureus-review. Folia Microbiol (Praha) 55: 548-558.
Miller, M.H. et al. (1978) Single and combination antibiotic therapy of Staphylococcus aureus experimental endocarditis: emergence of gentamicin-resistant mutants. Antimicrob Agents Chemother 14: 336-343.

Milner, S.E. et al. (2011) Bioactivities of GJycoalkaloids and Their Aglycones from Solanum Species, J. Agric. Food Chem., 59, p. 3454-3484.
Mingyu, H. et al. (2011) Multicolor, One- and Two-Photon Imaging of Enzymatic Activities in Live Cells with Fluorescently Quenched Activity-Based Probes (qABPs), JACS 133(31): 12009-12020.
Mitchell, G. et al. (2009) Tomatidine (TO) affects virulence regulators of prototypical Staphylococcus aureus (SA) and small-colony variants (SCV) of cystic fibrosis patients. Abstr. 49th Intersci. Conf. Antimicrob. Agents Chemother., abstr. C1-1341.
Mitchell, G. et al. (2010b) Staphylococcus aureus sigma B-dependent emergence of small-colony variants and biofilm production following exposure to Pseudomonas aeruginosa 4-hydroxy-2-heptylquinoline-N-oxide. BMC Microbiol 10: 33.
Mitchell, G. et al. (2010c) Defects in the cystic fibrosis transmembrane conductance regulator (CFTR) increase Staphylococcus aureus intracellular infection of human pulmonary cells. Abstr. 100th Gen. Meet. Am. Soc. Microbiol., abstr. D-1179.
Mitchell, G. et al. (2011) Tomatidine Inhibits the Replication of Staphylococcus aureus Small-Colony Variants in Cystic Fibrosis Airway Epithelial Cells. Antimicrob. Agents Chemother. 55 :1937-1945.
Mitchell, G. et al.(2012) Tomatidine acts in synergy with aminoglycoside antibiotics against multiresistant Staphylococcus aureus and prevents virulence gene expression. J. Antimicrob. Chemother. 67: 559-568.
Mitchell, G. et al. (2013) SigB is a dominant regulator of virulence in Staphylococcus aureus small-colony variants. PLoS One 8(5): e65018. doi:10.1371/journal.pone.0065018.
Mitchell, G., et al. (2010a) A role for sigma factor B in the emergence of Staphylococcus aureus small-colony variants and elevated biofilm production resulting from an exposure to aminoglycosides. Microb Pathog 48: 18-27.
Moisan, H. et al. (2006) Transcription of virulence factors in Staphylococcus aureus small-colony variants isolated from cystic fibrosis patients is influenced by SigB. J Bacteriol 188: 64-76.
Moskowitz, S. M. et al. (2004) Clinically feasible biofilm susceptibility assay for isolates of Pseudomonas aeruginosa from patients with cystic fibrosis. J Clin Microbiol 42(5): 1915-22.
Nagaoka, T. et al. (1993) Steroidal alkaloids from roots of tomato stock, Phytochem, 34(4), p. I 153-1157.
Nagy, E. (2010) Anaerobic infections: update on treatment considerations. Drugs 70: 841-858.
Nino, J. et al.(2009) Biological activities of steroidal alkaloids isolated from Solanum leucocarpum, Pharmaceutical Biology, 47(3), p. 255-259.
Osbourn, A.E. (1996) Preformed Antimicrobial Compounds and Plant Defense against Fungal Attack. Plant Cell 8: 1821-1831.
Palmer, M.L. et al. (2006) Protease-activated receptor regulation of Cl-secretion in Calu-3 cells requires prostaglandin release and CTFR activation. Am J Physiol Cell Physiol 290: C1189-1198.
Parkins, M.D. et al. (2010) Newer antibacterial agents and their potential role in cystic fibrosis pulmonary exacerbation management. J Antimicrob Chemother 65: 1853-1861.
Paulsen, H. et al. (1967) Monosaccharide mit stickstoflhaltigem Ring, XIV Untersuchungen ilber die magnetische Anisotropie der Amidgruppe, Chem. Ber., 100(10), p. 3385-3396. See N-formyl compound under y-Methyl on p. 3390.
Petrella, S. et al. (2006) Genetic Basis for Natural and Acquired Resistance to the Diarylquinoline R207910 in Mycobacteria. Antimicrob. Agents Chemother. 50: 2853-2856.
Proctor, R.A. et al. (2006) Small colony variants: a pathogenic form of bacteria that facilitates persistent and recurrent infections. Nat Rev Microbiol 4: 295-305.
Pyorala, S. et al. (2009) Coagulase-negative Staphylococci-emerging mastitis pathogens. Vet Microbiol 134: 3-8.
Qazi, S. et al. (2006) N-acylhomoserine lactones antagonize virulence gene expression and quorum sensing in Staphylococcus aureus. Infect Immun 74: 910-919.

FIG. 6A

ATP synthase subunit c
(NWMN_2012)

S. aureus hemB         ... 43  TAGGAGCAGGT 55...
S. aureus hemB (SaR1) ... 43  TAGGATCAGGT 55...

S. aureus hemB        ...185  AATTGCATTCA 197...
S. aureus hemB (SaR2) ...185  AATTACATTCA 197...

FIG. 6C

```
Bacterial species :              ATP synthase
                                 subunit C alias :  Amino acid sequence :
L. monocytogenes HCC23           LMHCC_0064         MSLGVIAAAIAVGLGALGGIGNGLIVSKTVEGVARQPEARSMLQTIMFI  50
L. ivanovii PAM 55               LIV_2444           MSLGVIAAAIAVGLGALGGIGNGLIVSKTVEGVARQPEARSMLQSIMFV  50
S. aureus N315                   SA1910             MNL---IAAAIAIGLSALGGIGNGLIVSKTVEGVARQPEARQGLMGIMFI  48
S. aureus Newman                 NWMN_2012          MNL---IAAAIAIGLSALGGIGNGLIVSRTVEGVARQPEARQGLMGIMFI  48
S. aureus USA300_FPR3757         SAUSA300_2063      MNL---IAAAIAIGLSALGGIGNGLIVSRTVEGVARQPEARQGLMGIMFI  48
S. haemolyticus JCSC1435         SH0927             MGL---IAAAIAIGLSALGGIGNGLIVSRTVEGVARQPEARQGLMSIMFI  48
S. lugdunensis N920143           SLUG_09580         MGL---IAAAIAIGLSALGGIGNGLIVSRTVEGVARQPEARQGLMSIMFI  48
S. epidermidis ATCC 12228        SE1705             MNL---IAAAIAIGLSALGGIGNGLIVSRTVEGVARQPEARQGLMGIMFI  48
S. pasteuri SP1                  STP1_0542          MNL---IAAAIAIGLSALGGIGNGLIVSRTVEGVARQPEARQGLMGIMFI  48
S. warneri SG1                   A284_03925         MNL---IAAAIAIGLSALGGIGNGLIVSRTVEGVARQPEARQGLMGIMFI  48
S. saprophyticus 15305           SSP0776            MNL---IAAAIAIGLSALGGIGNGLIVSRTVEGVARQPEARQGLMGIMFI  48
B. subtilis 6051-HGW             BSU6051_36860      MNL---IAAAIAIGLSALGGIGNGLIVSRTVEGIARQPEAGKELRTLMFM  48
B. anthracis Ames                BA_5552            MSLGVIAAAIAIGLSALGGIGNGLIVSRTIEGVARQPELKGALQTIMFI  50
B. cereus ATCC 14579             BC5311             MSLGVIAAAIAIGLSALGGIGNGLIVSRTIEGVARQPELKGALQTIMFI  50
Consensus                                           MXLXXIAAAIAXGLXALGGIGNGLIVSXTXEGXARQPEXXXLXXXMFX  50
B. coagulans 36D1                Bcoa_1456          MSLGILAAAIAVGLAALGRTVEGIARQPEARGLLQTTMFI  50
Consensus                                           MXLXXXAAAIAXGLXALGGIGNGLIVXXTXEGXARQPEXXXLXXXMFX  50

↓
L. monocytogenes                   GIGLVEALPIIAVVIGMVLNK  72
L. ivanovii PAM 55                 GVALVEALPIIAVVIGMVLNK  72
S. aureus N315                     GVGLVEALPIIGVVIGMTFAG  70
S. aureus Newman                   GVGLVEALPIIGVVIGMTFAG  70
S. aureus USA300_FPR3757           GVGLVEALPIIGVVIGMTFAG  70
S. haemolyticus JCSC1435           GIGLVEALPIIGVVIGMTLFQ  70
S. lugdunensis N920143             GIGLVEALPIIGVVIGMTLFR  70
S. epidermidis ATCC 12228          GVGLVEALPIIGVVIGMTFAG  70
S. pasteuri SP1                    GVGLVEALPIIGVVIGMTFAG  70
S. warneri SG1                     GVGLVEALPIIGVVIGMTFAG  70
S. saprophyticus 15305             GIGLVEALPIIGVVIGMSL--  68
B. subtilis 6051-HGW               GIALVEALPIIAVVIGLAFFG  70
B. anthracis Ames                  GVALVEALPIIGVVIGIVMNK  72
B. cereus ATCC 14579               GVALVEALPIIGVVIGIVMNK  72
Consensus                          GXXLVEALPIIXVVIGXXXXX  72
B. coagulans 36D1                  GIGLVEALPIIAVVIGTALGR  72
Consensus                          GXXLVEALPIIXXIXXXXXX  72
```

STEROID ALKALOIDS AND COMPOSITIONS AND KITS THEREOF

CROSS REFERENCE TO RELATED APPLICATIONS

This application is a continuation application of U.S. patent application Ser. No. 15/105,761 now allowed filed on Jun. 17, 2016, which is a National Entry application of PCT application Serial No PCT/CA2014/051262 filed on Dec. 23, 2014 and published in English under PCT Article 21(2), which itself claims benefit of U.S. provisional application Ser. No. 61/919,896, filed on Dec. 23, 2013. All documents above are incorporated herein in their entirety by reference.

FIELD OF THE INVENTION

The present invention relates to antimicrobial compounds and potentiators for antimicrobial compounds. The present invention is also concerned with the use of bacterial ATP synthase inhibitors such as steroid alkaloids, as antimicrobial agents, and potentiators of the antimicrobials activity of aminoglycosides against pathogenic bacterial strains, methods of manufacturing same, disinfection, sterilization or antisepsis methods using the same.

REFERENCE TO SEQUENCE LISTING

Pursuant to 37 C.F.R. 1.821(c), a sequence listing is submitted herewith as an ASCII compliant text file named 765-USPTO-SEQUENCE LISTING 14692-55_ST25, that was created on Jun. 17, 2016 and having a size of 27 kilobytes. The content of the aforementioned file is hereby incorporated by reference in its entirety.

BACKGROUND OF THE INVENTION

Staphylococci

Staphylococci are widely disseminated Gram-positive opportunistic bacterial pathogens responsible for many medical problems in humans, including skin and soft-tissue infections, surgical infections, endocarditis and hospital-acquired bacteriemia (Casey et al., 2007; Kloos and Bannerman, 1994). These bacteria are also the cause of several diseases in animals such as birds, cows, dogs, poultries, rabbits and others (Jacques et al., 2010; Pyorala and Taponen, 2009; Stepan et al., 2004). Staphylococci are divided in coagulase-positive species, *Staphylococcus aureus* (*S. aureus*) being the most clinically relevant of this group, and coagulase-negative species, such as *Staphylococcus epidermidis* (*S. epidermidis*), the most prevalent pathogen associated with infections of implanted medical devices (Vuong and Otto, 2002). The emergence and spread of resistance to multiple antibiotics in staphylococci is now considered a real health treat and impaired therapeutic endeavor to combat these bacteria (Witte et al., 2008).

*S. aureus* is an opportunistic pathogen that has extraordinary versatility. Diseases caused by this pathogen can affect several hosts, organs and body sites and may become both life threatening as well as chronic (Archer, 1998; Goerke and Wolz, 2004). For example, *S. aureus* is associated with significant mortality rates in hospitals and increased health costs (Talbot et al., 2006), but is also the most common cause of difficult-to-treat bovine mastitis (Sears and McCarthy, 2003). The ability of *S. aureus* to cause a broad spectrum of diseases is related to its numerous virulence factors (Archer, 1998) and it is likely that the coordinated or selected expression of specific groups of virulence factors contribute to the development of specific types of infections. For example, the formation of biofilms and the persistence within non-phagocytic host cells seem to facilitate the development of chronic infections by offering the bacterium protection against the host immune system and the action of antibiotics (Alexander and Hudson, 2001; Brouillette et al., 2004; Galli et al., 2007; Stewart, 2002).

Bacterial Small-Colony Variants

Bacterial small-colony variants (SCVs) are derived from normal bacterial strains and show a slow-growth phenotype (i.e., they produce small colonies when cultivated on solid media). *S. aureus* SCVs are known to form biofilms (Mitchell et al, 2010a; Mitchell et al, 2010b) and persist within non-phagocytic host cells (Sendi and Proctor, 2009). SCVs are bacteria with a dysfunctional oxidative metabolism causing an alteration in the expression of virulence factors, a slow growth and a loss of colony pigmentation (Proctor et al., 2006). This dysfunctional oxidative metabolism causes a decreased susceptibility to aminoglycosides because these antibiotics require the proton-motive force in order to penetrate the bacterium (Bryan and Kwan, 1981). The proton gradient (proton-motive force) normally generated by a functional electron transport chain is also used by the bacterial ATP synthase (also called $F_oF_1$-ATPase) to generate ATP (Hong and Pedersen, 2008). In *S. aureus*, the SCV phenotype results from mutations affecting the electron-transport system and several SCV isolates are auxotrophic for either hemin or menadione, which are needed to synthesize electron-transport system components. SCVs can also be auxotrophic for thiamine because thiamine is required for the biosynthesis of menadione. Other SCVs are no longer able to synthesize thymidine due to mutations in the folate pathway and this also results in a defect in electron transport although the fundamental basis of this is not well understood (Proctor et al., 2006). Some SCVs present yet unknown auxotrophy but still have in common electron transport deficiency which may result, for example, from a defect in the bacterial ATP synthase (Proctor et al., 2006). *S. aureus* SCVs are isolated from chronic infections, such as lung infections in cystic fibrosis (CF) patients and from osteomyelitis, septic arthritis, bovine mastitis and infection of orthopedic devices (Atalla et al., 2008; Moisan et al., 2006; Proctor et al., 2006). SCVs that are MRSA (methicillin-resistant *S. aureus*) and multiresistant to several class of antibiotics have also been reported (Vergison et al, 2007). It is now thought that switching from the normal to the SCV phenotype is an integral part of the pathogenesis of *S. aureus* and that novel therapeutic strategies targeting SCVs are needed to combat infections caused by bacterial species capable of generating electron transport-deficient SCVs (Tuchscherr et al., 2011).

The SCV phenotype is widespread among microbes. SCVs have been described for several bacterial species and have been recovered from many different clinical specimens such as abscesses, blood, bones and joints, the respiratory tract and soft tissues (Proctor et al., 2006). For examples, SCVs were detected among the staphylococci such as *Staphylococcus aureus*, *Staphylococcus epidermidis*, *Staphylococcus lugdunensis* and *Staphylococcus capitis*, among the enteric-disease causing bacteria such as *Salmonella* serovars, *Shigella* spp., *Escherichia coli* and *Vibrio cholerae*, among the nosocomial pathogens such as *Pseudomonas aeruginosa*, *Burkholderia cepacia*, *Escherichia coli*, *Serratia marcescens*, *Stenotrophomonas maltophilia* and *Enterococcus faecalis*, among the respiratory tract pathogens such as *Streptococcus pneumoniae* and *Coryne-*

*bacterium* spp., among uro-genital pathogens such as *Neisseria gonorrhoeae* and also in a variety of other species such as *Brucella melitensis* and *Lactobacillus lactophilus* (Allegrucci and Sauer, 2008; Melter and Radojevic, 2010; Proctor et al., 2006; Wellinghausen et al., 2009). In most of these cases, the SCV phenotype is consequent to a defect in the electron transport chain either caused by alteration of electron transport proteins, restriction in necessary coenzymes, cofactors or precursors or an overall reduction of some metabolic pathways such as the tricarboxilic cycle that ultimately affect and reduce electron transport (Chatterjee et al., 2007; Proctor et al., 2006).

Cystic Fibrosis

Although cystic fibrosis (CF) is fundamentally a genetic disorder, the majority of patients afflicted by this disease will ultimately succumb from respiratory failure subsequent to chronic bacterial infections (Lyczak et al., 2002). More recent investigations reveal that the CF airways are colonized by complex polymicrobial communities constituted of numerous microorganisms, encompassing more bacterial species than originally thought, and suggest that interactions between these microorganisms influence the course of the disease (Sibley and Surette, 2011). Some focus has been directed toward understanding the outcome of the interactions between *P. aeruginosa* and *S. aureus* because they are often co-isolated from the CF airways (Harrison, 2007; Hoffman et al., 2006; Mitchell et al., 2010b). The polymicrobial nature of CF lung infections needs to be considered in the development of novel therapeutic approaches (Sibley et al., 2009; Sibley and Surette, 2011).

*Staphylococcus aureus* is one of the most common pulmonary pathogens recovered from North American CF patients (Canadian Cystic Fibrosis Foundation, 2007; Cystic Fibrosis Foundation, 2008). While it is well accepted that antibiotic therapy leads to improvement of lung function and may reduce morbidity associated with CF, decisions regarding which antibiotics to use and when to treat remain largely empirical (Lyczak et al., 2002; Parkins and Elborn, 2010). Consequently, many antibiotics are currently used to treat CF patients infected with bacteria, including aminoglycoside antibiotics (Gibson et al., 2003; Lyczak et al., 2002). A major problem encountered by CF patients is the emergence of bacteria resistant to antibiotics. For example, the prevalence of methicillin-resistant *Staphylococcus aureus* (MRSA), most often multi-resistant to antibiotics (Chambers and Deleo, 2009), is increasing among CF patients (Parkins and Elborn, 2010). MRSA infections have been associated with a decline of lung function in CF patients (Dasenbrook et al., 2010). Recent studies demonstrate the deleterious effect of *S. aureus* SCVs and of MRSA and *Pseudomonas aeruginosa* co-infections in CF children and adults, respectively (Hubert et al, 2012; Wolter et al, 2013).

Burn Patients

Gram positive bacteria, mainly staphylococci and MRSA, as well as *Pseudomonas aeruginosa* cause severe infections or co-infections of burn wounds. Prophylactic and therapeutic antibiotics for burns patients often include aminoglycoside antibiotics (Avni et al, 2010).

Bovine Mastitis

Bovine mastitis is the most frequently occurring and costly disease affecting dairy producers. The transmittable bacterium *Staphylococcus aureus*, the coagulase-negative staphylococci and also many streptococci (*S. agalactiae, S. dysgalactiae, S. uberis* and others) are amongst the most common causes of intramammary infections leading to bovine mastitis (Tenhagen et al., 2006) and current antibiotic therapies usually fail to eliminate the infection from dairy herds (Sears, P. M. and K. K. McCarthy, 2003). Both the normal and SCV phenotypes of pathogenic bacteria were recovered from mastitis cases (Atalla et al., 2008).

Infections Caused by Antibiotic-Resistant Bacteria

Infections caused by antibiotic-resistant bacteria represent an overwhelming growing problem both in human and veterinary medicine. One reason explaining this widespread of drug resistances is that the currently available antibiotics have been largely designed on a limited number of chemical scaffolds, which allowed pathogens to adapt and circumvent common antibiotic action mechanisms (Shah, 2005; Talbot et al., 2006).

Foodborne Bacteria and Illnesses

A number of bacterial species such as *Listeria* spp. and *Bacillus* spp. can contaminate food and cause infections in humans. To name a few, *Listeria monocytogenes, L. ivanovii*, and *Bacillus cereus* can cause listeriosis (Guillet et al, 2010) and food poisoining (Bad Bug Book, FDA). *Bacillus subtilis, B. coagulans, B. licheniformis* and *B. sphaericus* are also known to cause illnesses. *Bacillus anthracis* causes anthrax and can often be acquired by contact with food producing animals and cattle (beef cattle, sheeps, etc.) and this bacterium is also well-known for its endospores that have been used as biological weapons (Beierlein and Anderson, 2011).

It would be highly desirable to identify antibiotic compounds targeting electron transport-deficient microbes (e.g., SCVs) and/or potentiating the growth inhibitory activity of aminoglycosides against pathogenic bacteria (e.g., antibiotic-resistant bacteria and/or those causing chronic and severe infections) and/or reducing bacterial resistance development toward aminoglycosides. It would also be highly desirable to identify antibiotic compounds that can be used to reduce bacterial colonization in food, preserve food or treat infections caused by foodborne pathogens.

The present description refers to a number of documents, the content of which is herein incorporated by reference in their entirety.

SUMMARY OF THE INVENTION

The present invention relates in part to the discovery that specific steroid alkaloids possess not only the ability to inhibit electron-transport deficient (e.g., SCVs, bacteria affected by another organism producing inhibitors of the electron transport chain) bacteria (e.g., Firmicutes (e.g., preferably the Bacillales *Staphylococcus, Bacillus* and *Listeria*)) but also possess antibacterial activity against normal Firmicutes (e.g., preferably the Bacillales *Staphylococcus, Bacillus* and *Listeria*) and the ability to potentiate the antibacterial activity of aminoglycosides against Firmicutes (e.g., preferably the Bacillales *Staphylococcus, Bacillus* and *Listeria*).

The present invention also shows that bacterial ATP synthase inhibitors targeting specific regions of the ATP synthase subunit C (e.g., steroid alkaloids) may be used to potentiate the antimicrobial activity of aminoglycosides (e.g., tobramycin, streptomycin, kanamycin, gentamicin, plazomycin and amikacin) against Firmicutes (e.g., preferably the Bacillales *Staphylococcus, Bacillus* and *Listeria*) and to inhibit electron-transport deficient (e.g., SCVs, bacteria affected by another organism producing inhibitors of the electron transport chain) bacteria (e.g., Firmicutes (e.g., preferably the Bacillales *Staphylococcus, Bacillus* and *Listeria*)).

Compounds and Compounds for Use

More particularly, the present invention provides in an embodiment, a compound of formula (I):

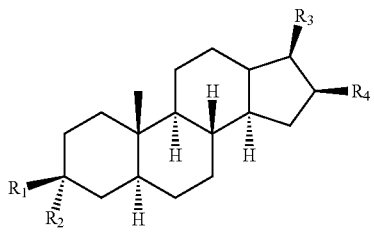

(I)

wherein:
R1 is H; and R2 is —OH or —NR5R6; or
R1 is —OH or —NR5R6; and R2 is H;
   wherein R5 and R6 are identical or different and are selected from the group consisting of H;
   substituted or unsubstituted alkyl; substituted or unsubstituted aryl; substituted or unsubstituted aralkyl; and substituted or unsubstituted —(CH$_2$)nNR7R8,
      wherein n is 2-10; and
      R7 and R8 are identical or different and are selected from the group consisting of H, substituted or unsubstituted alkyl, substituted or unsubstituted aryl and substituted or unsubstituted aralkyl;
   wherein the substituted alkyl(s), substituted aryl(s), substituted aralkyl(s) and substituted —(CH$_2$)nNR7R8 comprise(s) one or more identical or different substitutions selected from alkyl, aryl and aralkyl;
R3 is —C(CH$_3$)(NHR9),
   wherein R9 is H, substituted or unsubstituted alkyl, or substituted or unsubstituted —(CH$_2$)mNR11R12,
      wherein m is 2-10; and
      R11 and R12 are identical or different and are selected from the group consisting of H, substituted or unsubstituted alkyl, substituted or unsubstituted aryl and substituted or unsubstituted aralkyl
   wherein the substituted alkyl(s), substituted aryl(s), substituted aralkyl(s) and substituted —(CH$_2$)mNR11R12 comprise(s) one or more identical or different substitutions selected from alkyl, aryl and aralkyl; and
R4 is H,
   with the proviso that when R3 is —C(CH$_3$)(NHR9), R4 is H, R1 is OH and R2 is H, R9 is substituted or unsubstituted alkyl; or
R3 and R4 form together with the carbon atoms to which they are attached form a spirocyclic structure of formula II:

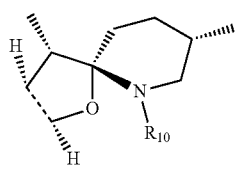

(II)

wherein R10 is H, substituted or unsubstituted alkyl, or substituted or unsubstituted —(CH$_2$)pNR13R14,
      wherein p is 2-10; and
      R13 and R14 are identical or different and are selected from the group consisting of H, substituted or unsubstituted alkyl, substituted or unsubstituted aryl and substituted or unsubstituted aralkyl;
   wherein substituted alkyl, substituted aryl, substituted aralkyl and substituted —(CH$_2$)pNR13R14 comprises one or more identical or different substitutions selected from alkyl, aryl and aralkyl,
   with the proviso that when R3 and R4 form together a spirocyclic structure of formula II, neither R1 nor R2 is —OH;
with the proviso that when R1 is NH2 and R2 is H; or R1 is H and R2 is NH2, R10 is not H,
or a stereoisomer or mixture of stereoisomers or a salt thereof,
(A) in combination with an aminoglycoside antibiotic for preventing or treating a bacterial infection in a subject; or
(B) (a) for preventing or treating an infection caused by an electron transport-deficient bacteria in a subject; or (b) for the disinfection, sterilization and/or antisepsis of an object contaminated with an electron transport-deficient bacteria.

In another aspect, the present invention provides a compound of formula (I):

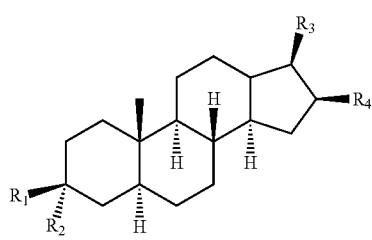

(I)

wherein:
R1 is H; and R2 is —OH or —NR5R6; or
R1 is —OH or —NR5R6; and R2 is H;
   wherein R5 and R6 are identical or different and are selected from the group consisting of H; substituted or unsubstituted alkyl; substituted or unsubstituted aryl; substituted or unsubstituted aralkyl; substituted or unsubstituted cycloalkyl, and substituted or unsubstituted —(CH$_2$)nNR7R8,
      wherein n is 2-10; and
      R7 and R8 are identical or different and are selected from the group consisting of H, substituted or unsubstituted alkyl, substituted or unsubstituted aryl; substituted or unsubstituted cycloalkyl, and substituted or unsubstituted aralkyl;
   wherein the substituted alkyl(s), substituted aryl(s), substituted aralkyl(s), substituted cycloalkyl(s), and substituted —(CH$_2$)nNR7R8 comprise(s) one or more identical or different substitutions selected from alkyl, aryl, cycloalkyl and aralkyl;
R3 is —C(CH$_3$)(NHR9),
   wherein R9 is H, substituted or unsubstituted alkyl, or substituted or unsubstituted —(CH$_2$)mNR11R12,
      wherein m is 2-10; and
      R11 and R12 are identical or different and are selected from the group consisting of H, substituted or unsubstituted alkyl, substituted or unsubstituted aryl, substituted or unsubstituted cycloalkyl, and substituted or unsubstituted aralkyl
   wherein the substituted alkyl(s), substituted aryl(s), substituted aralkyl(s), substituted cycloalkyl(s), and substituted —(CH$_2$)mNR11R12 comprise(s) one or more identical or different substitutions selected from alkyl, aryl, cycloalkyl and aralkyl; and
R4 is H,
with the proviso that when R3 is —C(CH₃)(NHR9), R4 is H, R1 is OH and R2 is H, R9 is substituted or unsubstituted alkyl;
wherein the substituted alkyl comprises one or more identical or different substitutions selected from alkyl, aryl, cycloalkyl and aralkyl; or
R3 and R4 form together with the carbon atoms to which they are attached form a spirocyclic structure of formula II:

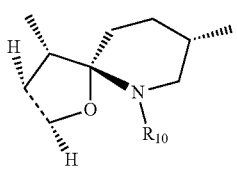

(II)

wherein R10 is H, substituted or unsubstituted alkyl, or substituted or unsubstituted —(CH₂)pNR13R14, wherein p is 2-10; and
R13 and R14 are identical or different and are selected from the group consisting of H, substituted or unsubstituted alkyl, substituted or unsubstituted aryl, substituted or unsubstituted cycloalkyl, and substituted or unsubstituted aralkyl;
wherein substituted alkyl, substituted aryl, substituted aralkyl, substituted cycloalkyl, and substituted —(CH₂)pNR13R14 comprises one or more identical or different substitutions selected from alkyl, aryl, cycloalkyl and aralkyl,
with the proviso that when R3 and R4 form together a spirocyclic structure of formula II, neither R1 nor R2 is —OH; and
with the proviso that when R1 is NH2 and R2 is H; or R1 is H and R2 is NH2, R10 is not H, or a stereoisomer or mixture of stereoisomers or a salt thereof,
(A) in combination with an aminoglycoside antibiotic for preventing or treating a bacterial infection in a subject; or
(B) (a) for preventing or treating an infection caused by an electron transport-deficient bacteria in a subject; or (b) for the disinfection, sterilization and/or antisepsis of an object contaminated with an electron transport-deficient bacteria.

In a specific embodiment of the compound, R3 is —C(CH₃)(NHR9), and R4 is H, with the proviso that when R1 is OH and R2 is H, R9 is substituted or unsubstituted alkyl.

In another specific embodiment of the compound, R9 is substituted or unsubstituted alkyl. In another specific embodiment of the compound, R9 is —(CH₂)qCHR15R16, wherein q is 1 to 6. In another specific embodiment of the compound, R15 and R16 are identical or different and are selected from the group consisting of H, substituted or unsubstituted alkyl, substituted or unsubstituted aryl, substituted or unsubstituted cycloalkyl, and substituted or unsubstituted aralkyl, wherein substituted alkyl, substituted aryl, substituted cycloalkyl, substituted aralkyl and substituted —(CH₂)pNR13R14 comprises one or more identical or different substitutions selected from alkyl, aryl, cycloalkyl and aralkyl. In another specific embodiment of the compound, R15 and R16 are identical or different and are selected from the group consisting of H, substituted or unsubstituted alkyl. In another specific embodiment of the compound, R15 and R16 are identical or different and are selected from the group consisting of H and unsubstituted alkyl. In another specific embodiment of the compound, R15 and R16 are identical or different and are selected from the group consisting of H and —CH₃. In another specific embodiment of the compound, R15 and R16 are H. In another specific embodiment of the compound, R15 and R16 are —CH₃. In another specific embodiment of the compound, q is 2 or 3. In another specific embodiment of the compound, wherein q is 2. In another specific embodiment of the compound, R1 is H and R2 is —OH; or R1 is —OH and R2 is H.

In another specific embodiment, the compound is

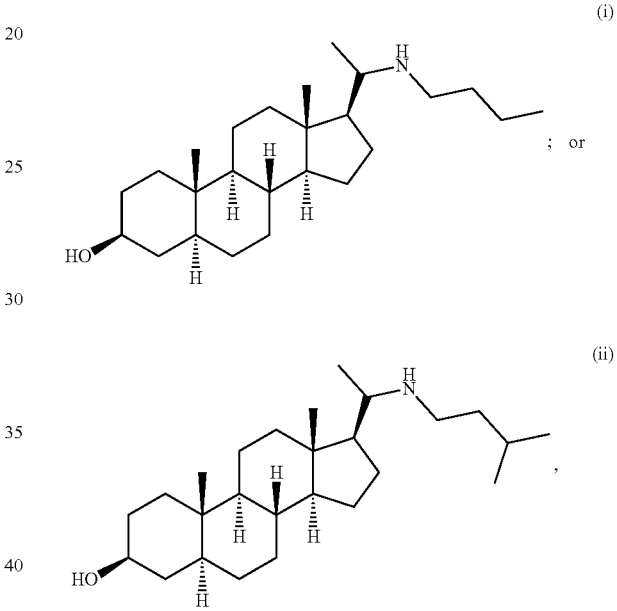

or a salt, stereoisomer or any mixture of stereoisomers of (i) or (ii).

In another specific embodiment, R3 and R4 form together a spirocyclic structure of formula II.

In another specific embodiment, R10 is H, or substituted or unsubstituted alkyl. In another specific embodiment, R10 is H, or substituted or unsubstituted alkyl C1-C5. In another specific embodiment, R10 is H.

In another specific embodiment, R1 is H and R2 is —NR5R6; or R1 is —NR5R6 and R2 is H.

In another specific embodiment, R5 is H and R6 is —(CH₂)nNR7R8 or R6 is H and R5 is —(CH₂)nNR7R8. In another specific embodiment, R7 and R8 are identical or different and are selected from the group consisting of H and substituted or unsubstituted alkyl. In another specific embodiment, R7 and R8 are are identical or different and are selected from the group consisting of H and substituted or unsubstituted alkyl C1 to C3. In another specific embodiment, R7 and R8 are H. In another specific embodiment, n is 2 to 6. In another specific embodiment, n is 2. In another specific embodiment, n is 4. In another specific embodiment, n is 6.

In another specific embodiment, the compound is

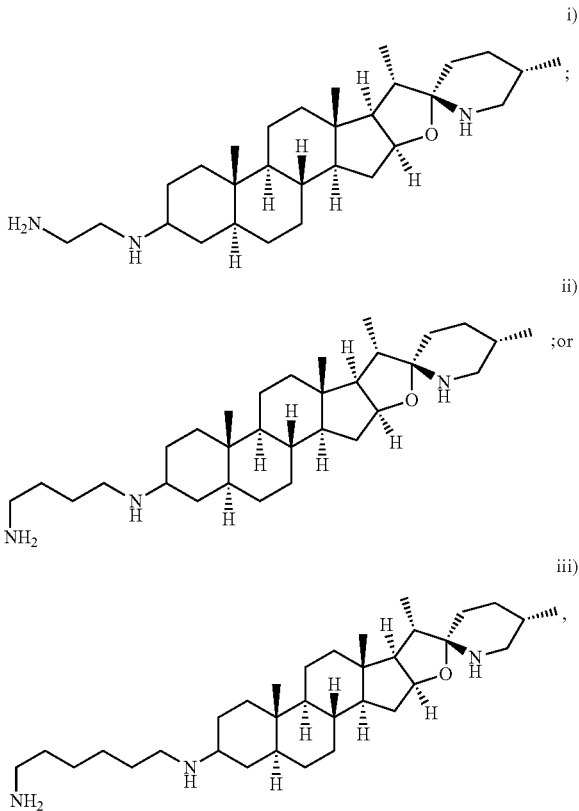

or or a salt, stereoisomer or any mixture of stereoisomers of any one of (i) to (iii).

In accordance with another aspect, the present invention provides a compound inhibiting a bacterial ATP synthase by targeting (1) a first conserved region of the bacterial ATP synthase subunit C polypeptide ("first conserved region") defined by (A) LX$_1$X$_2$X$_3$AAAIAX$_4$GLX$_5$ALG AGIGNGLIVX$_6$X$_7$TX$_8$EGX$_9$ARQPEX$_{10}$ (SEQ ID NO: 24) wherein X1, X2, X3, X4, X5, X6, X7, X8, X9, or X10 are any amino acid; or X1 is an aliphatic amino acid or absent, preferably glycine or absent; X2 is an aliphatic amino acid or absent, preferably valine or absent; X3 is an aliphatic amino acid, preferably isoleucine or leucine; X4 is an aliphatic amino acid, preferably valine or isoleucine; X5 is any amino acid, preferably an aliphatic amino acid or an hydroxyl or sulfur containing amino acid, more preferably glycine, serine or alanine; X6 is any amino acid, preferably an aliphatic amino acid or an hydroxyl or sulfur containing amino acid, preferably serine or glycine; X7 is a basic amino acid, preferably lysine or arginine; X8 is an aliphatic amino acid, preferably valine or isoleucine; X9 is an aliphatic amino acid, preferably valine or isoleucine; and X10 is an aliphatic amino acid, preferably alanine or leucine; or (B) defined by LX$_1$X$_2$IAAAIAX$_3$GLX$_4$ALG AGIGNGLIVSX$_5$TX$_6$EGX$_7$ARQPEX$_8$ (SEQ ID NO: 27), wherein X1 is an aliphatic amino acid or absent, preferably glycine or absent; X2 is an aliphatic amino acid or absent, preferably valine or absent; X3 is an aliphatic amino acid, preferably valine or isoleucine; X4 is any amino acid, preferably an aliphatic amino acid or an hydroxyl or sulfur containing amino acid, more preferably glycine or serine; X5 is a basic amino acid, preferably lysine or arginine; X6 is an aliphatic amino acid, preferably valine or isoleucine; X7 is an aliphatic amino acid, preferably valine or isoleucine; and X8 is an aliphatic amino acid, preferably alanine or leucine; and/or (2) a second conserved region of the bacterial ATP synthase subunit C polypeptide ("second conserved region"), defined by GZ$_1$Z$_2$LVEALPIIZ$_3$VVIAF (SEQ ID NO: 30), wherein Z1, Z2 and Z3 are any amino acid, or wherein Z1 is an aliphatic amino acid, preferably valine or isoleucine; Z2 is an aliphatic amino acid, preferably glycine or alanine; and Z3 is an aliphatic amino acid, preferably glycine or alanine, (A) in combination with an aminoglycoside antibiotic for preventing or treating a infection by a Firmicutes phylum bacteria of the order Bacillales in a subject; or (B) (a) for preventing or treating a bacterial infection caused by an electron transport-deficient bacteria in a subject; or (b) for the disinfection, sterilization and/or antisepsis of an object contaminated with an electron transport-deficient bacteria, wherein the inhibitor is not tomatidine, tomatidine 3-sulfate, tomatidine 3-phosphate, 3α-hydroxytomatidine, 3-oxo-tomatidine, 3-aminotomatidine, N-formyl tomatidine, N-formyl-3α-acetyltomatidine, 3α-hydroxytomatidine, N-formyl-3-oxotomatidine, 3-oxotomatidine, O-allyl-N-formyltomatidine, O-allyltomatidine, tomatidine methanesulfonate, tomatidine citrate, O-acetyl-N-benzylpregn-5,6-en-3β-ol-20-amine, pregnan-3β-ol-20-amine, O-acetylpregn-5,6-en-3β-ol-20-((N,N-dimethylamino)propyl)amine, pregnan-3β-ol-20-((N,N-dimethylamino)propyl)amine, O-acetylpregnan-3β-ol-20-(boc-aminoethyl)amine, O-acetylpregnan-3β-ol-20-(boc-aminopropyl)amine, O-acetylpregnan-3β-ol-20-(boc-aminobutyl)amine, pregnan-3β-ol-20-(boc-aminoethyl)amine, pregnan-3β-ol-20-(boc-aminopropyl)amine, pregnan-3β-ol-20-(boc-aminobutyl)amine, pregnan-3β-ol-20-(aminoethyl)amine, pregnan-3β-ol-20-(aminopropyl)amine, pregnan-3β-ol-20-(aminobutyl)amine, O-t-butyldimethylsilylpregnanolone, t-Butyldimethysilylpregnane-3,20-diol, pregnane-3,20-diol, pregnanolone, O-t-butyldimehylsilyl-21-bromopregnanolone, N,N-dimethyl-21-aminopregnanolone, 21-piperidinopregnanolone, N-methyl-21-aminopregnanolone, 21-piperazinopregnanolone, aminothiazole, 3β-hydroxy-20-(pyrid-2-yl)-5α-pregnane, 3β-hydroxy-20-(thiazol-2-yl)-5α-pregnane, 3β-hydroxy-20-(piperidin-2-yl)-5α-pregnane, 3β-hydroxy-20-(thiazol-4-yl)-5α-pregnane, 3β-hydroxy-20-(imidazol-4-yl)-5α-pregnane, 3-methoxymethyltomatidine, 26-amino-3β-hydroxy-16β-methoxy-21-methyl-5α-cholestano-22,26-piperidine, (25S)-26-Acetyl amino-3β,16β-dihydroxy-5a-cholestane, 3β-hydroxy-20-(2-aminothiazol-4-yl)-5α-pregnane hydrochloride or a salt thereof.

In accordance with another aspect, the present invention provides a compound inhibiting a bacterial ATP synthase by targeting the ATP synthase subunit C conserved region: (i) LX$_1$X$_2$X$_3$AAAIAX$_4$GLX$_5$ALG AGIGNGLIVX$_6$X$_7$TX$_8$EGX$_9$ARQPEX$_{10}$ as set forth in SEQ ID NO: 24, 25 or 26; or (ii) GZ$_1$Z$_2$LVEALPIIZ$_3$VVI AF as set forth in SEQ ID NO: 30, 31 or 32, (A) in combination with an aminoglycoside antibiotic for preventing or treating a infection by a Firmicutes phylum bacteria of the order Bacillales in a subject; or (B) (a) for preventing or treating a bacterial infection caused by an electron transport-deficient bacteria in a subject; or (b) for the disinfection, sterilization and/or antisepsis of an object contaminated with an electron transport-deficient bacteria, wherein the inhibitor is not tomatidine, tomatidine 3-sulfate, tomatidine 3-phosphate, 3α-hydroxytomatidine, 3-oxo-tomatidine, 3-aminotomatidine, N-formyl tomatidine, N-formyl-3α- acetyltomatidine, 3α-hydroxytomatidine, N-formyl-3-oxo-tomatidine, 3-oxotomatidine, O-allyl-N-formyltomatidine, O-allyltomatidine, tomatidine methanesulfonate, tomatidine citrate, O-acetyl-N-benzylpregn-5,6-en-3β-ol-20-amine, pregnan-3β-ol-20-amine, O-acetylpregn-5,6-en-3β-ol-20-((N,N-dimethylamino)propyl)amine, pregnan-3β-ol-20-((N,N-dimethylamino)propyl)amine, O-acetylpregnan-3β-ol-20-(boc-aminoethyl)amine, O-acetylpregnan-3β-ol-20-(boc-aminopropyl)amine, O-acetylpregnan-3β-ol-20-(boc-aminobutyl)amine, pregnan-3β-ol-20-(boc-aminoethyl) amine, pregnan-3β-ol-20-(boc-aminopropyl)amine, pregnan-3β-ol-20-(boc-aminobutyl)amine, pregnan-3β-ol-20-(aminoethyl)amine, pregnan-3β-ol-20-(aminopropyl) amine, pregnan-3β-ol-20-(aminobutyl)amine, O-t-butyldimethylsilylpregnanolone, t-Butyldimethysilylpregnane-3,20-diol, pregnane-3,20-diol, pregnanolone, O-t-butyldimehylsilyl-21-bromopregnanolone, N,N-dimethyl-21-aminopregnanolone, 21-piperidinopregnanolone, N-methyl-21-aminopregnanolone, 21-piperazinopregnanolone, aminothiazole, 3β-hydroxy-20-(pyrid-2-yl)-5α-pregnane, 3β-hydroxy-20-(thiazol-2-yl)-5α-pregnane, 3β-hydroxy-20-(piperidin-2-yl)-5α-pregnane, 3β-hydroxy-20-(thiazol-4-yl)-5α-pregnane, 3β-hydroxy-20-(imidazol-4-yl)-5α-pregnane, 3-methoxymethyltomatidine, 26-amino-3β-hydroxy-163-methoxy-21-methyl-5α-cholestano-22,26-piperidine, (25S)-26-Acetyl amino-3β,16β-dihydroxy-5a-cholestane, 3β-hydroxy-20-(2-aminothiazol-4-yl)-5α-pregnane hydrochloride or a salt thereof.

In a specific embodiment, the compound is (i) the compound, stereoisomer, mixture of stereoisomers or salt as defined above; or (ii) (R)-3-((R)-(6-bromo-2-methoxyquinolin-3-yl)(phenyl)methyl)-7-(4-methylpiperazin-1-yl)-1-phenylheptan-3-ol; (1R,2S)-1-(6-bromo-2-methoxyquinolin-3-yl)-2-(2,5-difluorophenyl)-6-(dimethylamino)-1-phenylhexan-2-ol; (R)-3-((R)-(6-bromo-2-methoxyquinolin-3-yl)(4-methoxyphenyl)methyl)-1-(dimethylamino)-5-phenylpentan-3-ol; or (S)-3-((R)-(6-bromo-2-methoxyquinolin-3-yl)(phenyl)methyl)-7-(methylamino)-1-phenylheptan-3-ol.

In a specific embodiment, the compound is for preventing or treating a bacterial infection in a subject; or (b) for the disinfection, sterilization and/or antisepsis of an object contaminated by the bacteria. In another specific embodiment, the bacterial infection or contamination is caused by normal bacteria.

In another specific embodiment, the compound is in combination with an aminoglycoside antibiotic for preventing or treating a bacterial infection in a subject. In another specific embodiment, the compound further comprises the use of a beta-lactam.

In another specific embodiment, the bacterial infection is caused by electron-transport deficient bacteria. In another specific embodiment, the bacteria are small-colony variants (SCVs). In another specific embodiment, the bacterial infection is caused by multidrug resistant bacteria. In another specific embodiment, the bacteria are Firmicutes phylum bacteria. In another specific embodiment, the Firmicutes phylum bacteria are Bacillales. In another specific embodiment, the bacteria are of the genus *Staphylococcus*. In another specific embodiment, the bacteria are of the genus *Listeria*. In another specific embodiment, said subject is a human.

In accordance with another aspect, the present invention provides a compound as defined above, or a stereoisomer, any mixture of stereoisomers or a salt thereof.

In accordance with another aspect, there is provided a compound of the invention (e.g., listed in Table 1 below) or a salt, stereoisomer or any mixture of stereoisomers of such compound. In accordance with another embodiment, there is provided a compound of the invention (e.g., listed in Table 1 below) which has a moderate to high potentiation activity and or a moderate to high antibacterial activity or a salt, stereoisomer or any mixture of stereoisomers of such compound.

Compositions and Kits

In accordance with another aspect, there is provided a composition comprising at least one of the compounds as defined herein, and (i) an antibiotic; (ii) an antiseptic; (iii) a disinfectant; (iv) a diluent; (v) an excipient; (vi) a pharmaceutically acceptable carrier; or (vii) any combination of (i)-(vi).

In a specific embodiment, said composition is a pharmaceutical composition. In another specific embodiment, the composition comprises (i) the compound as defined herein; and (ii) an antibiotic, which is an aminoglycoside antibiotic. In another specific embodiment, the composition further comprises a beta-lactam antibiotic.

In accordance with another aspect of the present invention, there is provided a kit comprising the compound defined herein or the above-mentioned composition, and instructions to use same in the prevention or treatment of a bacterial infection.

In a specific embodiment of the kit, the kit comprises: (i) one or more compounds defined herein; and/or (ii) one or more compositions defined herein, and instructions to use same in the prevention or treatment of a microbial infection. In another specific embodiment of the kit, the kit further comprises (iii) an antiseptic; (iv) a disinfectant; (v) a diluent; (vi) an excipient; (vii) a pharmaceutically acceptable carrier; or (viii) any combination of (iii)-(vii). In another specific embodiment of the kit, the kit comprises: (a) an antibiotic; (b) an antiseptic; (c) a disinfectant; (d) any combination of (a)-(c).

In accordance with another aspect, there is provided a kit comprising the compound as defined herein, and instructions to use same in (a) the prevention or treatment of a bacterial infection; or (b) the disinfection, sterilization and/or antisepsis of an object.

In a specific embodiment, the kit further comprises an aminoglycoside antibiotic. In another specific embodiment, the kit further comprises a beta-lactam antibiotic.

In another specific embodiment, the kit further comprises: (iii) an antiseptic; (iv) a disinfectant; (v) a diluent; (vi) an excipient; (vii) a pharmaceutically acceptable carrier; or (viii) any combination of (iii)-(vii).

In another specific embodiment, the kit further comprises: (i) an antibiotic; (ii) an antiseptic; (iii) a disinfectant; or (iv) any combination of (i)-(iii).

More specifically, in accordance with another aspect of the present invention, there is provided a kit comprising the compound as defined above, and instructions to use same in (a) the prevention or treatment of a microbial infection; or (b) the disinfection, sterilization and/or antisepsis of an object.

In a specific embodiment of the kit, the kit further comprises an aminoglycoside antimicrobial agent. In another specific embodiment of the kit, the aminoglycoside antimicrobial agent is amikacin, gentamicin, kanamycin, streptomycin, tobramycin or plazomycin. In another specific embodiment of the kit, the kit further comprises a beta-lactam antimicrobial agent.

In a specific embodiment of the composition or kit, the aminoglycoside antimicrobial agent is amikacin, gentamicin, kanamycin, streptomycin, tobramycin or plazomycin. In a specific embodiment of the composition, the composition further comprises a beta-lactam antimicrobial agent. In a specific embodiment of the composition, the composition comprises a compound as defined herein or a salt, stereoisomer or any mixture of stereoisomers of such compound. In another specific embodiment of the composition, the composition comprises a compound as listed in Table 1 below or a salt, stereoisomer or any mixture of stereoisomers of such compound. In accordance with yet another embodiment, the composition comprises a compound as listed in Table 1 below which has a moderate to high potentiation activity and or a moderate to high antibacterial activity or a salt, stereoisomer or any mixture of stereoisomers of such compound.

In another specific embodiment of the compounds for uses (or corresponding methods or uses), said subject or object is food, a cow or a human. In another specific embodiment of the compounds for uses (or corresponding methods or uses), said subject is a human.

Screening Methods

In accordance with another aspect of the present invention, there is provided a method of identifying a pathogen, the microbial infection of which is treatable by the compound as defined herein or a composition comprising the compound, said method comprising contacting said bacterial pathogen with said compound or composition and determining the effect of said compound or composition on the growth or survival of said pathogen, wherein a decrease in the growth or survival of said pathogen in the presence as compared to in the absence of said compound or composition is an indication that said bacterial pathogen is treatable by said compound or composition.

In a specific embodiment of the method, use and compositions for uses of the present invention, said subject is an animal (e.g., cattle such as cow; goat, ewe, ass, horse, pig, cat, dog, etc.). In another specific embodiment, said subject is a cow. In another specific embodiment, said subject is a human.

Other advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

(FIG. 3B) the effect of compound 14 (Cpd; 8 μg/mL) on Listeria monocytogenes SCVs compared to that obtained with tomatidine hydrochloride salt (TO; 8 μg/mL) used at the same concentration expressed in percent of residual CFUs. Compound 14 is bactericidal against the L. monocytogenes SCV.

(FIG. 4B) a comparison of the effect of compound 14 (Cpd) used alone with that of tomatidine hydrochloride salt (TO) against normal Staphylococcus aureus grown in biofilms. In combination with gentamicin, Compound 14 is bactericidal against normal S. aureus grown in biofilm (in FIG. 4A, Log 10 CFU/peg). Compound 14 can also disrupt biofilm formation when used alone (in FIG. 4B, residual OD562 nm (%)).

FIGS. 6A-C presents in FIG. 6A, two different mutations identified in the nucleotide sequence of the ATP synthase gene (gene NWMN_2012, from the S. aureus Newman annotation) of S. aureus NewbouldΔhemB (hemB) mutants obtained after sequential passages on tomatidine (e.g., mutant SaR1) and on tomatidine and gentamicin (e.g., mutant SaR2). The position and nature of the mutations are indicated in bold characters (parental strain ATP synthase subunit S. aureus hemB nucleotide sequences (SEQ ID NOs: 1 and 3) vs. corresponding ATP synthase subunit S. aureus mutants SaR1 (SEQ ID NO: 2) or SaR2 (SEQ ID NO: 4) nucleotide sequences). In FIG. 6B-C the amino acid sequence of the target of tomatidine, identified as the bacterial ATP synthase subunit c (gene NWMN_2012, from the S. aureus Newman annotation). The amino acid sequences for the ATP synthase subunit c were found on pubmed/protein (http://www.ncbi.nlm.nih.gov/pubmed) with the following accession numbers. In B-C amino acid sequences or residues for S. aureus Newman BAF68284.1 (GenBank) (SEQ ID NO: 5); Listeria monocytogenes HCC23 (YP_002349041.1) (SEQ ID NO: 6) Bacillus subtilis 6051-HGW (YP_007535682) (SEQ ID NO: 7); Bacillus cereus ATCC 14579 (NP_834973) (SEQ ID NO: 8); Bacillus anthracis Ames (NP_847710) (SEQ ID NO: 9); Streptococcus pneumoniae D39 (YP_816803.1 (NCBI)) (SEQ ID NO: 10); E. coli AAA24732.1 (GenBank) (SEQ ID NO: 11); Mycobacterium smegmatis MC2 155 (YP_006569554.1 (NCBI)) (SEQ ID NO: 12); and Homo sapiens P48201.1 (UniProtKB/Swiss-Prot) (SEQ ID NO: 13) are shown. In C, amino acid sequences for the following strains are also shown Staphylococcus aureus N315 (SEQ ID NO: 5); Staphylococcus aureus USA300_FPR3757 (SEQ ID NO: 5)); Listeria ivanovii PAM 55 (SEQ ID NO: 14); Staphylococcus haemolyticus JCSC1435 (SEQ ID NO: 15); Staphylococcus lugdunensis N920143 (SEQ ID NO: 16); Staphylococcus epidermidis strain ATCC12228 (Q8CNJ2 UniProtKB/Swiss-Prot) (SEQ ID NO: 17); Staphylococcus pasteuri SP1 (SEQ ID NO: 18); Staphylococcus warneri SG1 (SEQ ID NO: 19); Staphylococcus saprophyticus 15305 (SEQ ID NO: 20); (SEQ ID NO: 7); and Bacillus

*coagulans* 36D1 (SEQ ID NO: 21). Consensus sequences are depicted that are derived from the alignment of the full ATP synthase subunit C amino acid sequences of species/strains shown in panel C including *B. coagulans* (SEQ ID NO: 22); and of species/strains shown in panel C except *coagulans* (SEQ ID NO: 23). Each of the "X"s in these consensus sequences refers to any amino acid. Within these consensus sequences (SEQ ID NOs: 22-23) are shown highlighted sequences corresponding to first (SEQ ID NOs: 24 and 27) and second (SEQ ID NO: 30) conserved regions of the ATP synthase subunit C polypeptide. The comparative amino acid sequence alignments were performed using the ClustalW2™ program (http://www.ebi.ac.uk/Tools/services/web/toolform.ebi?tool=clustalw2). The proton-binding glutamic acid (E [or aspartic acid, D in *E. coli*]) is indicated by an arrow. The changes in amino acids for mutated positions reported for the diarylquinoline-resistant strains of *Mycobacterium tuberculosis* or *M. smegmatis* (MyR) (MyR denotes a mixture of these two species) or of *Streptococcus pneumoniae* (SpR) are indicated below the alignments (Andries et al, 2005; Petrella et al, 2006; Balemans et al, 2012; Segala et al, 2012), along with the changes in amino acids found in the tomatidine-resistant *Staphylococcus aureus* hemB mutants (SaR1 and SaR2). Notably, the nature of the amino acids that is present at the positions of the mutations for *S. aureus* SaR1 and SaR2 is conserved at both positions among the listed Firmicutes (boxed positions). Single-letter amino acid abbreviations: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

Figure 7:
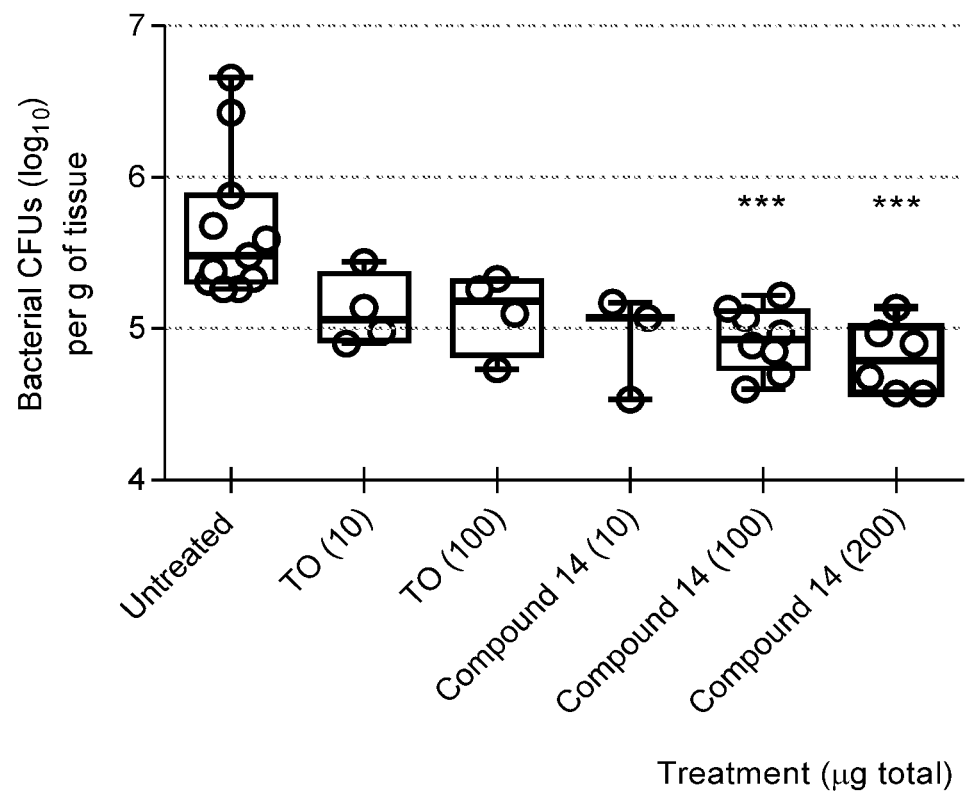

FIG. 7 presents compound 14's efficacy in a murine lung infection (pneumonia) model.

DESCRIPTION OF ILLUSTRATIVE EMBODIMENTS

Antimicrobial Activity of Compounds of the Present Invention

In certain embodiments, the present invention relates to the unexpected discovery that inhibitors of bacterial ATP synthase targeting specific regions of the subunit C of the enzyme have a very potent growth inhibitory activity against not only electron transport-deficient bacteria but also against normal (i.e. non electron-transport deficient) bacteria (e.g., firmicutes phylum (e.g., preferably the Bacillales *Staphylococcus, Bacillus* and *Listeria*)).

The present invention also encompasses using a compound of the present invention with at least another active ingredient (e.g., another antibiotic agent).

Compounds of the present invention may be used as antimicrobial compounds against microbial targets described herein, through their ATP synthase inhibitory activity or through other mechanisms.

Potentiating Activity of Compounds of the Present Invention

In other embodiments, the present invention also relates to the surprising discovery that bacterial ATP synthase inhibitors targeting specific regions of subunit C of the ATP synthase enzyme selectively potentiate the inhibitory activity of aminoglycoside antimicrobial agents against normal (i.e. non electron transport-deficient (e.g., non-SCVs)) bacteria (e.g., firmicutes (e.g., preferably the Bacillales *Staphylococcus, Bacillus* and *Listeria*)) such as *Staphylococcus* spp, *Bacillus* and *Listeria*. In addition to increasing the potency of aminoglycoside-based therapies, such inhibitors/compounds of the present invention used in combination with aminoglycosides may also reduce the development of resistance to aminoglycosides in bacteria. The present invention thus also relates to the use of at least one compound of the present invention in combination with an aminoglycoside antimicrobial agent to improve the antibiotic efficacy of the aminoglycoside (i.e., to create a synergy and to reduce the development of resistance) in a therapeutic approach that selectively treat or prevent bacterial infections caused by bacteria such as firmicutes phylum (e.g., preferably the Bacillales *Staphylococcus, Bacillus* and *Listeria*) in subjects in need thereof.

Compounds of the present invention may be used as potentiators of the inhibitory activity of aminoglycoside antimicrobial agents against microbial targets described herein, through their ATP synthase inhibitory activity or through other mechanisms.

Definitions

The use of the word "a" or "an" when used in conjunction with the term "comprising" in the claims and/or the specification may mean "one" but it is also consistent with the meaning of "one or more", "at least one", and "one or more than one".

As used herein the term "microbe" includes without being limited to a bacterium.

As used here in the term "infection" refers to a monomicrobic or a polymicrobic infection. It refers to infections involving at least one microbial target of the present invention (e.g., a normal bacteria (e.g., firmicutes (e.g., preferably the Bacillales *Staphylococcus, Bacillus* and *Listeria*)), an electron transport-deficient bacteria (SCVs, etc.), a bacterial pathogen targeted by aminoglycoside firmicutes (e.g., preferably the Bacillales *Staphylococcus, Bacillus* and *Listeria*)). In a particular embodiment, such bacteria are of the Firmicutes phylum. In a more specific embodiment, such bacteria are preferably the Bacillales. In a more specific embodiment such bacteria are Bacillales such as *Staphylococcus, Listeria* and *Bacillus* spp. Without being so limited, infections targeted by the compounds of the present invention includes food-borne infections, an infection of the airways of cystic fibrosis patients, hospital-acquired pneumonia, or an infection associated with burns, implantation of catheter, or endotracheal tube, etc.

As used herein the terms "polymicrobic infection" are interchangeable with the terms "mixed infection", "co-infection" or "polymicrobial infection". As used herein, they refer to a co-culture, an infection, a colonization, a community or a population of microbes of different species or strains found together either as planktonic organisms or embedded in a biofilm structure. More particularly, polymicrobic infections targeted by compounds of the present invention include at least one microorganism (e.g., bacteria) producing at least one electron transport inhibitor (e.g., *Pseudomonas aeruginosa* (Lightbown and Jackson, 1956; Machan et al., 1992; Mitchell et al., 2010b; Voggu et al., 2006)) and/or at least one molecule related to 4-hydroxy-2-alkylquinolines produced by certain microorganisms (e.g., bacteria) (e.g., *Burkholderia* species (Vial et al., 2008)). Without being so limited, such polymicrobic infections may be found in any pathologic situation where staphylococci and *P. aeruginosa* co-infect a same host (e.g., cystic fibrosis and hospital-acquired infections (e.g., pneumonia and infections associated with burns, catheters, and endotracheal tubes)) (Chastre and Fagon, 2002; Harlid et al, 1996; Harrison, 2007; Hoffman et al, 2006).

The use of the word "bacterium" in this specification and claim(s) may be interchanged with the words "bacteria", "bacterial pathogen", "infectious agent", "strain" or "bacterial strain" (e.g., living either as planktonic microorganism, embedded in a biofilm structure or intracellular).

As used herein the terms "reducing the development of resistance" toward an antimicrobial agent (e.g., aminoglycoside) refers to a reduction in the number of bacteria that become resistant to the antimicrobial agent when treated with the antimicrobial agent in combination with a compound of the present invention as compared to when treated with the antimicrobial agent alone. As used herein the term "reduce", "reduction" or "decrease" or "prevention" of development of resistance toward an antimicrobial agent refers to a reduction in development of resistance toward an antimicrobial agent of at least 10% as compared to reference (e.g., treatment with antimicrobial agent alone) development of resistance, in an embodiment of at least 20% lower, in a further embodiment of at least 30%, in a further embodiment of at least 40%, in a further embodiment of at least 50%, in a further embodiment of at least 60%, in a further embodiment of at least 70%, in a further embodiment of at least 80%, in a further embodiment of at least 90%, in a further embodiment of 100% (complete prevention).

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Compound

As used herein, the terms "molecule", "compound" and "agent" are used interchangeably and broadly to refer to natural, synthetic or semi-synthetic molecules or compounds. The term "compound" therefore denotes, for example, chemicals, macromolecules, cell or tissue extracts (from plants or animals) and the like. Non-limiting examples of compounds include peptides, antibodies, carbohydrates, nucleic acid molecules and pharmaceutical agents. The compound can be selected and screened by a variety of means including random screening, rational selection and by rational design using, for example, ligand modeling methods such as computer modeling. As will be understood by the person of ordinary skill, molecules having non-naturally occurring modifications are also within the scope of the term "compound". For example, the compounds of the present invention can be modified to enhance their activity, stability, and/or bioavailability, and also to lower its toxicity. The compounds or molecules identified in accordance with the teachings of the present invention have a therapeutic value in diseases or conditions related to microbial infections.

As used herein, the terms "bacterial ATP synthase subunit C" refers to an ATP synthase subunit C defined by the sequence as set forth in SEQ ID NO: 22 (consensus derived from ATP synthase subunit C polypeptides of bacterial species depicted in FIG. 6C). In a specific embodiment, it refers to a sequence as set forth in SEQ ID NO: 23. In these sequences, each "X" refers to any amino acid. In another embodiment, each X refers to any amino acid belonging to the same class as any of the amino acid residues in the corresponding position of the ATP synthase subunit C polypeptide sequence of any species of Bacillales. In another embodiment, each X refers to any amino acid in the corresponding position of the ATP synthase subunit C polypeptide sequence of any *Staphylococcus* (e.g., coagulase-positive or -negative), *Bacillus* or *Listeria*. In another embodiment, each X refers to any amino acid belonging to the same class as any of the amino acid residues in the corresponding position of the ATP synthase subunit C polypeptide sequence of *S. aureus, S. intermedius, S. epidermidis, S. haemolyticus, S. hyicus, S. chromogenes, S. stimulans, S. saprophyticus, S. hominis, S. lugdunensis, S. capitis, Bacillus subtilis, Bacillus anthracis, Bacillus cereus, Bacillus coagulans, Listeria monocytogenes* or *Listeria ivanovii*. In another embodiment, each X refers to any amino acid belonging to the same class as any of the amino acid residues in the corresponding position of the ATP synthase subunit C polypeptide sequence of any bacterial species depicted in FIG. 6C. The Table below indicates which amino acid belongs to each amino acid class.

| Class | Name of the amino acids |
| --- | --- |
| Aliphatic | Glycine, Alanine, Valine, Leucine, Isoleucine |
| Hydroxyl or Sulfur/Selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their Amide | Aspartate, Glutamate, Asparagine, Glutamine |

In another embodiment, each X refers to any amino acid in the corresponding position of the ATP synthase subunit C polypeptide sequence of *S. aureus, S. intermedius, S. epidermidis, S. haemolyticus, S. hyicus, S. chromogenes, S. stimulans, S. saprophyticus, S. hominis, S. lugdunensis, S. capitis, Bacillus subtilis, Bacillus anthracis, Bacillus cereus, Bacillus coagulans, Listeria monocytogenes* or *Listeria ivanovii*. In another embodiment, each X refers to any amino acid in the corresponding position of the ATP synthase subunit C polypeptide sequence of any bacterial species depicted in FIG. 6C.

As used herein, the terms "bacterial ATP synthase inhibitor targeting the ATP synthase subunit C" refer to any inhibitor that specifically targets or interacts with (1) a first conserved region of the bacterial ATP synthase subunit C polypeptide ("first conserved region") defined by (A) $LX_1X_2X_3AAAIAX_4GLX_5ALG$ $AGIGNGLIVX_6X_7TX_8EGX_9ARQPEX_{10}$ (SEQ ID NO: 24) wherein X1, X2, X3, X4, X5, X6, X7, X8, X9, or X10 are any amino acid; or X1 is an aliphatic amino acid or absent, preferably glycine or absent; X2 is an aliphatic amino acid or absent, preferably valine or absent; X3 is an aliphatic amino acid, preferably isoleucine or leucine; X4 is an aliphatic amino acid, preferably valine or isoleucine; X5 is any amino acid, preferably an aliphatic amino acid or an hydroxyl or sulfur containing amino acid, more preferably glycine, serine or alanine; X6 is any amino acid, preferably an aliphatic amino acid or an hydroxyl or sulfur containing amino acid, preferably serine or glycine; X7 is a basic amino acid, preferably lysine or arginine; X8 is an aliphatic amino acid, preferably valine or isoleucine; X9 is an aliphatic amino acid, preferably valine or isoleucine; and X10 is an aliphatic amino acid, preferably alanine or leucine; or (B) defined by $LX_1X_2IAAAIAX_3GLX_4ALG$ $AGIGNGLIVSX_5TX_6EGX_7ARQPEX_8$ (SEQ ID NO: 27), wherein X1 is an aliphatic amino acid or absent, preferably glycine or absent; X2 is an aliphatic amino acid or absent, preferably valine or absent; X3 is an aliphatic amino acid, preferably valine or isoleucine; X4 is any amino acid, preferably an aliphatic amino acid or an hydroxyl or sulfur containing amino acid, more preferably glycine or serine; X5 is a basic amino acid, preferably lysine or arginine; X6 is an aliphatic amino acid, preferably valine or isoleucine; X7 is an aliphatic amino acid, preferably valine or isoleucine; and X8 is an aliphatic amino acid, preferably alanine or leucine. Preferably within this region, it targets any subregion of 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 amino acid residue(s). More preferably, within the first conserved region, the inhibitor targets the subregion ALGAGIG (SEQ ID NO: 33); even more preferably within this region, it targets the subregion LGAGI (SEQ ID NO: 34), ALGAG (SEQ ID NO: 35) or GAGIG (SEQ ID NO: 36); more preferably within this region, it targets the subregion LGA, GAG or AGI; even more preferably within this region, it targets the subregion GA or AG; and even more preferably, it targets the A residue (underlined in the full conserved region). For instance in the strains Staphylococcus aureus Newman BAF68284.1 (SEQ ID NO: 5); Staphylococcus aureus N315 (SEQ ID NO: 5); Staphylococcus aureus USA300_FPR3757 (SEQ ID NO: 5); Staphylococcus epidermidis strain ATCC12228 (Q8CNJ2 UniProtKB/Swiss-Prot) (SEQ ID NO: 17); Staphylococcus haemolyticus JCSC1435 (SEQ ID NO: 15); Staphylococcus lugdunensis N920143 (SEQ ID NO: 16); Staphylococcus pasteuri SP1 (SEQ ID NO: 18); Staphylococcus warneri SG1 (SEQ ID NO: 19); Staphylococcus saprophyticus 15305 (SEQ ID NO: 20); Bacillus subtilis str. 168 (CAA82255.1 (GenBank)) (SEQ ID NO: 7); and Bacillus subtilis 6051-HGW (SEQ ID NO: 7), the first conserved region is located at positions 3 to 38 of these bacteria's ATP synthase subunit C, and residues X1 and X2 is absent. In these strains, the region ALGAGIG (SEQ ID NO: 33) is located at positions 14 to 20 inclusively of these bacteria's ATP synthase subunit C. In the strains Listeria monocytogenes YP_007604993.1 (SEQ ID NO: 6); Listeria ivanovii PAM 55 (SEQ ID NO: 14); Bacillus cereus ISO75 (EJP90090.1 (GenBank)) (SEQ ID NO: 8); Bacillus cereus ATCC 14579 (SEQ ID NO: 8; Bacillus anthracis Ames (SEQ ID NO: 9); Bacillus anthracis str. H9401 (YP_006212349.1 (NCBI)) (SEQ ID NO: 9); and Bacillus coagulans 36D1 (SEQ ID NO: 21), the first conserved region is located at positions 3 to 40 of these bacteria's ATP synthase subunit C, and residues X1 and X2 are present. In these strains, the region ALGAGIG (SEQ ID NO: 33) is located at positions 16 to 22 inclusively of these bacteria's ATP synthase subunit C; and/or with (2) a second conserved region of the bacterial ATP synthase subunit C polypeptide ("second conserved region"), defined by $GZ_1Z_2LVEALPIIZ_3VVIAF$ (SEQ ID NO: 30), wherein Z1, Z2 and Z3 are any amino acid, or wherein Z1 is an aliphatic amino acid, preferably valine or isoleucine; Z2 is an aliphatic amino acid, preferably glycine or alanine; and Z3 is an aliphatic amino acid, preferably glycine or alanine. Preferably within this region, it targets any subregion of 17 amino acid residues. More preferably, it targets IAF; more preferably within this region, it targets IA or AF; even more preferably within this region, it targets the residue A. For instance in the strains S. aureus Newman BAF68284.1 (SEQ ID NO: 5); Staphylococcus aureus N315 (SEQ ID NO: 5); Staphylococcus aureus USA300_FPR3757 (SEQ ID NO: 5); S. epidermidis ATCC12228 (Q8CNJ2 UniProtKB/Swiss-Prot) (SEQ ID NO: 17); Staphylococcus haemolyticus JCSC1435 (SEQ ID NO: 15); Staphylococcus lugdunensis N920143 (SEQ ID NO: 16); Staphylococcus pasteuri SP1 (SEQ ID NO: 18); Staphylococcus warneri SG1 (SEQ ID NO: 19); Staphylococcus saprophyticus 15305 (SEQ ID NO: 20); in Bacillus subtilis str. 168 (CAA82255.1 (GenBank)) (SEQ ID NO: 7); and Bacillus subtilis 6051-HGW (SEQ ID NO: 7), the second conserved region is located at positions 49 to 65 of these bacteria's ATP synthase subunit C. In these strains, the region IAF is located at positions 63 to 65 inclusively of these bacteria's ATP synthase subunit C. In the strain Listeria monocytogenes YP_007604993.1 (SEQ ID NO: 6); Listeria ivanovii PAM 55 (SEQ ID NO: 14); Bacillus cereus ISO75 (EJP90090.1 (GenBank)) (SEQ ID NO: 8); Bacillus cereus ATCC 14579 (SEQ ID NO: 8); Bacillus anthracis Ames (SEQ ID NO: 9); Bacillus anthracis str. H9401 (YP_006212349.1 (NCBI)) (SEQ ID NO: 9); and Bacillus coagulans 36D1 (SEQ ID NO: 21), the second conserved region is located at positions 51 to 67 of this strain's ATP synthase subunit. In that strain, the region IAF is located at positions 65 to 67 of this bacteria's ATP synthase subunit.

In a specific embodiment, the ATP synthase inhibitors of the present invention specifically target bacterial ATP synthase (and not, or to a lesser extent, other types of ATP synthases such as e.g., mitochondrial ATP synthases). Exemplified compounds of the present invention represent some examples of such ATP synthase inhibitors.

As used herein the term "aryl" unless otherwise expressly characterized, may refer to a substituted or unsubstituted aryl (e.g., C5-C6, C5 or C6) (which may be an heterocycle i.e. one or more carbon replaced by another atom (e.g., N, O, S, etc.), wherein the substituent(s), if any, is one or more identical or different substituents selected from an alkyl, aryl, aralkyl, which alkyl, aryl, aralkyl may be substituted or not with one or more alkyl, aryl, cycloalkyl and/or aralkyl, halide, OH, OMe, $NO_2$, $NH_2$ and/or $CO_2H$, including heterocycles. Herein, the term "substituted aryl" is sometimes expressly used. In a specific embodiment, the substituent(s) may be one or more identical or different substituents selected from an alkyl, aryl, cycloalkyl and/or aralkyl.

As used herein the term "alkyl" unless otherwise characterized, may refer to saturated or unsaturated (e.g., allyle), substituted or unsubstituted, and/or linear or branched alkyl (C1 to C10, or C2 to C9, or C3 to C8, of C4 to C7, or C5 to C6, or C1, C2, C3, C4, C5, C6, C7, C8, C9 or C10), wherein the substituent(s), if any, is one or more identical or different substituents selected from an alkyl, aryl, aralkyl, which alkyl, aryl, aralkyl may be substituted or not with one or more alkyl, aryl and/or aralkyl, halide, OH, OMe, $NO_2$, $NH_2$ and/or $CO_2H$. Without being so limited, it includes —$CH_2$—CH=$CH_2$, and —$(CH_2)_3$—CH($CH_3$)$CH_2$. Herein, the term "substituted alkyl" is sometimes also expressly used. In a specific embodiment, the substituent(s) may be one or more identical or different substituents selected from an alkyl, aryl, cycloalkyl and/or aralkyl.

As used herein the term "aralkyl" unless otherwise expressly characterized, refers to a radical derived from an alkyl radical by replacing one or more hydrogen atoms by aryl groups. It includes saturated or unsaturated, substituted or unsubstituted, linear or branched aralkyl (C1 to C10, or C2 to C9, or C3 to C8, of C4 to C7, or C5 to C6, or C1, C2, C3, C4, C5, C6, C7, C8, C9 or C10), wherein the substituent, if any, is one or more identical or different substituents selected from an alkyl, aryl, aralkyl, which alkyl, aryl, aralkyl may be substituted or not with one or more alkyl, aryl and/or aralkyl halide, OH, OMe, $NO_2$, $NH_2$ or $CO_2H$. Herein, the term "substituted aryl" is sometimes also expressly used. In a specific embodiment, the substituent(s) may be one or more identical or different substituents selected from an alkyl, aryl, cycloalkyl and/or aralkyl.

As used herein the term "cycloalkyl" unless otherwise expressly characterized, refers to refer to a substituted or unsubstituted cycloalkyl (e.g., C3-C7, C3, C4, C5, C6, or C7) (which may be an heterocycle i.e. one or more carbon replaced by another atom (e.g., N, O, S, etc.)), wherein the substituent(s), if any, is one or more identical or different substituents selected from an alkyl, aryl, aralkyl, which alkyl, aryl, aralkyl may be substituted or not with one or more alkyl, aryl and/or aralkyl, halide, OH, OMe, $NO_2$, $NH_2$ and/or $CO_2H$. Herein, the term "substituted cycloalkane" is sometimes also expressly used. In a specific embodiment, the substituent(s) may be one or more identical or different substituents selected from an alkyl, aryl, cycloalkyl and/or aralkyl.

As used herein the terms "substituted —$(CH_2)nNR7R8$" refer to —$(CH_2)nNR7R8$ that may comprise one or more identical or different substituents selected from an alkyl, aryl and/or aralkyl, which alkyl, aryl, aralkyl may be substituted or not with one or more alkyl, aryl cycloalkyl and/or aralkyl.

As used herein the terms "substituted —$(CH_2)mNR11R12$" refer to —$(CH_2)mNR11R12$ that may comprise one or more identical or different substituents selected from an alkyl, aryl and/or aralkyl, which alkyl, aryl, aralkyl may be substituted or not with one or more alkyl, aryl, cycloalkyl and/or aralkyl.

As used herein the terms "substituted —$(CH_2)pNR13R14$" refer to —$(CH_2)pNR13R14$ that may comprise one or more identical or different substituents selected from an alkyl, aryl and/or aralkyl, which alkyl, aryl, aralkyl may be substituted or not with one or more alkyl, aryl, cycloalkyl and/or aralkyl.

As used herein the term <<CO>> refers to a carbonyl.

The symbols used herein to denote the orientation of the hydrogen atoms are those used in the tomatidine formula presented below at the left, wherein "=" denotes □-H and "•" β-H. They are used to identify the stereochemistry of tertiary carbons (having three direct neighbors other than hydrogens). The classical representation of the hydrogens is shown in the right formula for tomatidine for comparison purposes. Such convention is used to simplify the formulas.

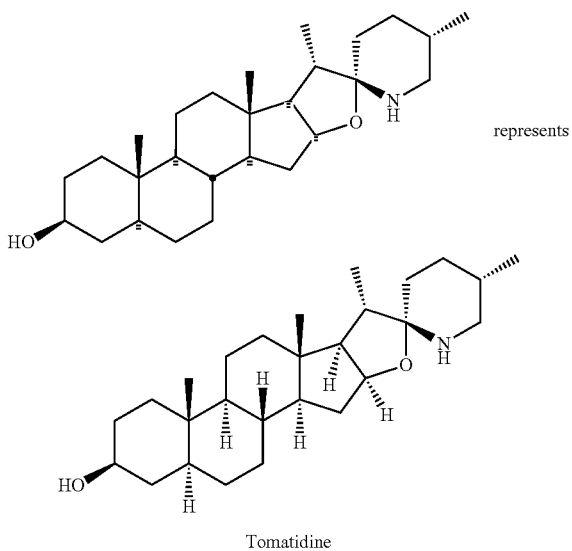

Tomatidine

As used herein the term "aminoglycoside" refers to an aminoglycoside antimicrobial agent and include without being so limited to amikacin, arbekacin, gentamicin, kanamycin, dideoxykanamycin, neomycin, neamine, lividomycin, butirosin, netilmicin, paromomycin, rhodostreptomycin, streptomycin, tobramycin, framycetin, ribostamycin, bekanamycin, dibekacin, hygromycin B, sisomicin, isepamicin, verdamicin, astromicin, apramycin, fortimycin, sorbistin, kasugamycin, istamycin, sagamicin, spectinomycin and other known aminoglycosides. The term aminoglycoside also includes herein the 4,5-disubstituted deoxystreptamines, 4,6-disubstituted deoxystreptamines, aminocyclitols, streptidines, actinanimes, deoxystreptamines, destomycins. It also includes neoglycosides or "next-generation aminoglycosides" (e.g., plazomycin, ACHN-490) namely aminoglycosides able to circumvent bacterial resistance mechanisms used against previous aminoglycosides.

As used herein the term "combination" when used in reference to the use of the compound of the invention in combination with at least one other antibiotic (e.g., aminoglycoside) means i) simultaneously (e.g., in separate compositions or a single composition); ii) simultaneously as a single dual action compound (e.g., a conjugate of the two or more, the compound of the invention chemically linked with at least another antibiotic) in a single composition; or iii) subsequently (e.g., in separate compositions wherein the compound of the present invention is administered before (e.g., immediately before) or after (e.g., immediately after) the at least other antibiotic).

The present invention encompasses therefore the use of a combination of two, three or more active ingredients including at least one compound of the present invention. A combination of three compounds in accordance of the present invention can include a compound of the present invention, an aminoglycoside and a beta-lactam (e.g., Ubrolexin™ (i.e. cefalexin [or cephalexin] and kanamycin)).

Microbial Targets

Compounds of the present invention may be used as antimicrobial agents. In this respect, the compounds of the present invention are used against normal microbes (e.g., bacteria) and "electron transport-deficient microbes".

The compounds of the present invention may be used against normal or electron-transport deficient bacteria, preferably of the Firmicutes phylum. While there are currently more than 274 genera within the Firmicutes phylum, notable genera of Firmicutes include the Bacilli, order Bacillales, *Bacillus, Listeria*, and the *Staphylococcus*. Such microbial species include, more particularly, but are not limited to coagulase-positive and -negative staphylococci such as *S. aureus, S. intermedius, S. epidermidis, S. haemolyticus, S. hyicus, S. chromogenes, S. stimulans, S. saprophyticus, S. hominis, S. lugdunensis* and *S. capitis*. Also more particularly targeted are *Bacillus subtilis, Bacillus anthracis, Bacillus cereus, Bacillus coagulans, Listeria monocytogenes* and *Listeria ivanovii*. The compounds of the present invention most preferably target the Bacillales.

As used herein the term "electron transport-deficient microbes" refers for example to SCVs that have a defect in the electron transport chain, and to bacteria of a polymicrobic infection that have been affected by at least one electron transport inhibitor and/or at least one molecule related to 4-hydroxy-2-alkylquinolines produced by at least one microorganism (e.g., bacteria) (e.g., *Pseudomonas aeruginosa, Burkholderia* species) or also present in the infection. In a specific embodiment it refers to SCVs that have a defect in the electron transport chain, and to bacteria of a polymicrobic infection that have been affected by at least one electron transport inhibitor and/or at least one molecule related to 4-hydroxy-2-alkylquinolines produced by at least one microorganism (e.g., bacteria) (e.g., *Pseudomonas aeruginosa, Burkholderia* species). In another more specific embodiment, it refers to SCVs.

SCVs may have a defect in the electron transport chain caused by mutation, sub-optimal expression, sub-optimal biosynthesis or alteration of electron transport proteins, necessary coenzymes, cofactors or precursors, a defect in the bacterial $F_oF_1$-ATPase or proton pumps or an overall reduction of certain metabolic pathways such as the tricarboxilic cycle that ultimately affects and reduces electron transport. SCVs of a variety of bacterial species of human or animal origins are thus microbial targets of the compounds of the present invention. In a specific embodiment, the SCV is a Firmicutes phylum bacterium.

The term "electron transport-deficient microbes" also refers to bacteria of a polymicrobic infection that are affected by at least one electron transport inhibitor and/or at least one molecule related to 4-hydroxy-2-alkylquinolines produced by at least one microorganism (e.g., bacteria (e.g., *Pseudomonas aeruginosa, Burkholderia* species) also present in the infection.

Compounds of the present invention may also be used as potentiators of antimicrobial agents. As used herein, the term "potentiator" in the context of an "antimicrobial agent potentiator" refers to an agent which increases the antimicrobial activity of another antimicrobial agent on a bacterium and thus creates a synergy, i.e., the activity of the combination of agents is superior to that observed for either agent individually.

In this respect, the compounds of the present invention may be used in combination with aminoglycosides against "normal" (i.e. non electron transport-deficient) bacterial targets of human or animal origins that include but are not limited to Firmicutes phylum bacteria as described above (e.g., staphylococci, *Bacillus, Listeria*, etc.). In a specific embodiment, the normal (i.e. non-electron transport-deficient) target of the compounds of the invention used as potentiators of aminoglycosides is a Gram-positive bacterium.

In a particular embodiment, the compounds of the present invention are used as potentiators of aminoglycosides against normal staphylococcal strains (e.g., *Staphylococcus aureus, Staphylococcus epidermidis*), *Bacillus* or *Listeria* strains.

Subjects and Objects

As used herein the term "object" refers to an animal or to an animal tissue (e.g., skin, hands), an animal cells (e.g., in cell cultures for laboratory purpose or for use for administration to subjects), food (e.g., packaged food preparation, meat, milk, milk products, etc.), a synthetic material or a natural material. Synthetic materials include, without being so limited, working surfaces (e.g., table, counter), instruments, prosthetic devices and biomaterials. The term "Natural material" includes, without being so limited, skin grafts, tissue cultures and organs.

As used herein the term "subject" or "patient" refers to an animal, preferably a mammal such as but not limited to a human, cow, goat, ewe, ass, horse, pig, chicken, cat, dog, etc. who is the object of treatment, observation or experiment.

Excipients/Carriers

As used herein, the terms "pharmaceutically acceptable" refer to molecular entities and compositions that are physiologically tolerable and do not typically produce an allergic or similar untoward reaction, such as gastric upset, dizziness and the like, when administered to animals (e.g., cows, humans). Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin.

Routes of Administration

Compounds of the invention may be administered in a pharmaceutical composition. Pharmaceutical compositions may be administered in unit dosage form. Any appropriate route of administration may be employed, for example, transdermal (topical), parenteral, subcutaneous, intramuscular, intramammary, intracranial, intraorbital, ophthalmic, intraventricular, intracapsular, intraarticular, intraspinal, intracisternal, intraperitoneal, intranasal, aerosol, or oral administration. Examples of specific routes of administration include parenteral, e.g., intravenous, intradermal, subcutaneous, intramammary; oral (e.g., inhalation); transdermal (topical); transmucosal, and rectal administration.

Conventional pharmaceutical practice may be employed to provide suitable formulations or compositions to administer such compositions to patients. Methods well known in the art for making pharmaceutical compositions and formulations are found in, for example, Remington: The Science and Practice of Pharmacy, (20th ed.) ed. A. R. Gennaro A R., 2000, Lippincott: Philadelphia.

Formulations

Therapeutic formulations for oral administration, may be in the form of tablets or capsules; for transmucosal (e.g., rectal, intranasal) or transdermal/percutaneous administration may be in the form of ointments, powders, nebulized or non-nebulized dry powders, nasal drops, sprays/aerosols or suppositories; for topical administration, may be in the form of ointments, creams, gels or solutions; for parenteral administration (e.g., intravenously, intramuscularly, intradermal, intramammary, subcutaneously, intrathecally or transdermally), using for example injectable solutions. Furthermore, administration can be carried out sublingually or as ophthalmological preparations or as an aerosol, for example in the form of a spray. Intravenous, intramuscular or oral administration is generally a preferred form of use. A spray or nebulized or non-nebulized dry powders is a preferred form of use for rapid local administration in the lungs. Ointments, creams, gels or solutions added or not to bandages are preferred forms for treatment of burn wounds.

The pharmaceutical compositions of the present invention may also contain excipients/carriers such as preserving agents, solubilizing agents, stabilizing agents, wetting agents, emulsifiers, sweeteners, colorants, odorants, salts for the variation of osmotic pressure, buffers, coating agents or antioxidants. As mentioned earlier, they may also contain other therapeutically valuable agents.

Oral

For the purpose of oral therapeutic administration, the active compound can be incorporated with excipients and used for example in the form of tablets, troches, dragees, hard or soft gelatin capsules, solutions (e.g., syrups), aerosols, emulsions or suspensions, or capsules. For the preparation of formulations for oral administration, the compounds of the present invention may be admixed with pharmaceutically inert, inorganic or organic excipients (e.g., pharmaceutically compatible binding agents, and/or adjuvant). The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Examples of suitable excipients for tablets, dragees or hard gelatin capsules for example include lactose, maize starch or derivatives thereof, talc or stearic acid or salts thereof. Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

Nasal

For administration by inhalation through the mouth or nose, the compounds may be delivered in the form of an aerosol spray from pressured container or dispenser which contains a suitable propellant, e.g., a gas such as carbon dioxide, or a nebulizer. Nebulized or non-nebulized dry powders may be inhaled. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Transmucosal or Transdermal (Topical)

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. For suppositories, and local or percutaneous application, excipients which may be used include for example natural or hardened oils, waxes, fats and semi-solid or liquid polyols.

Parenteral

Pharmaceutical compositions suitable for injectable use include sterile aqueous solutions (where water soluble) or dispersions and sterile powders for the extemporaneous preparation of sterile injectable solutions or dispersion. Solutions or suspensions used for parenteral application can include the following components: a sterile diluent such as water for injection (where water soluble), saline solution, fixed oils (e.g., paraffin oil), polyalkylene glycols such as polyethylene glycols, glycerine, propylene glycol or other synthetic solvents, oils of vegetable origin, or hydrogenated napthalenes; antibacterial agents such as benzyl alcohol or methyl parabens; antioxidants such as ascorbic acid or sodium bisulfite; chelating agents such as ethylenediaminetetraacetic acid; reducing agents such as dithiothreitol, buffers such as acetates, citrates or phosphates and agents for the adjustment of tonicity such as sodium chloride or dextrose. The pH can be adjusted with acids or bases, such as hydrochloric acid or sodium hydroxide. Biocompatible, biodegradable lactide polymer, lactide/glycolide copolymer, or polyoxyethylene-polyoxypropylene copolymers may be used to control the release of the compounds. Other potentially useful parenteral delivery systems for compounds of the invention include ethylenevinyl acetate copolymer particles, osmotic pumps, implantable infusion systems, and liposomes. The parenteral preparation can also be enclosed in ampoules, disposable syringes or multiple dose vials made of glass or plastic.

For intravenous or intramammary administration, suitable carriers include physiological saline, bacteriostatic water, Cremophor EL™ (BASF, Parsippany, N.J.) or phosphate buffered saline (PBS).

Liposomal suspensions (including liposomes targeted to specific cell types) can also be used as pharmaceutically acceptable carriers. A variety of liposomal formulations suitable for delivering a compound to an animal have been described and demonstrated to be effective in delivering a variety of compound, including, e.g., small molecules, nucleic acids, and polypeptides.

As mentioned earlier, medicaments containing the compounds of the present invention are also an object of the present invention, as is a process for the manufacture of such medicaments, which process comprises bringing one or more of the compounds of the present invention to, if desired, one or more other therapeutically valuable substances into a galenical administration form.

Compounds

Protective Group

The compounds of the present invention may include protective groups. As used herein, and without being so limited, the term "protective group" is meant to refer to a substituent on a heteroatom that may be cleaved in specified reaction conditions to unmask the heteroatom and includes without being so limited tert-butoxycarbonyle (BOC), t-butyldimethylsilyl (TBDMS), methoxymethyl (MOM), etc. Further examples of protecting groups may be found in Protective groups in organic synthesis, 4th edition, Peter G. M. Wuts & Theodora W. Greene editors, Wiley 2007.

Salts, Esters, Hydrates and Solvates

The compounds of the present invention include pharmacologically acceptable salts and ester derivatives thereof as well as hydrates or solvates thereof and all stereoisomeric forms of the referenced compounds. The compounds and pharmacologically acceptable esters thereof of the present invention can form pharmacologically acceptable salts if necessary.

Salts

The terms "pharmacologically acceptable salt thereof" refer to a salt to which the compounds of the present invention can be converted. Preferred examples of such a salt include alkali metal salts such as a sodium salt, a potassium salt, a lithium salt, magnesium or calcium salts; alkaline earth metal salts such as a calcium salt and a magnesium salt; metal salts such as an aluminium salt, an iron salt, a zinc salt, a copper salt, a nickel salt and a cobalt salt; amine salts such as inorganic salts including an ammonium salt; organic salts or ammonium salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt and a tris(hydroxymethyl)aminomethane salt; inorganic acid salts such as hydrohalic acid salts such as a hydrofluoride, a hydrochloride, a hydrobromide or a hydroiodide, a nitrate, a perchlorate, a sulfate or a phosphate; lower alkanesulfonates such as a methanesulfonate (mesylate), trifluoromethanesulfonate or an ethanesulfonate; arylsulfonates such as a benzenesulfonate or a p-toluenesulfonate and the like, which are non toxic to living organisms; organic acid salts such as an acetate, a malate, adipate, a fumarate, a succinate, a citrate, alginate, ascorbate, benzoate, benzenesulfonate, bisulfate, butyrate, camphorate, camphorsulfonate, cinnamate, cyclopentanepropionate, digluconate, dodecylsulfate, ethanesulfonate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, sulfonate, methanesulfonate, trifluoromethanesulfonates, ethanesulfonates 2-naphthalenesulfonate, nicotinate, nitrate, oxalate, pamoate, pectinate, persulfate, 3-phenylpropionate, picrate, pivalate, propionate, tartrate, thiocyanate, tosylate, and undecanoate, a tartrate, an oxalate or a maleate; and amino acid salts such as a glycine salt, a lysine salt, an arginine salt, an ornithine salt, histidine, a glutamate or an aspartate salt. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others. For further example, see S. M. Berge, et al. "Pharmaceutical Salts," J. Pharm. Sci. 1977, 66, 1-19. Such salts can be formed quite readily by those skilled in the art using standard techniques.

More specific examples of the salts formed with an acidic group present in the compounds of the present invention include metal salts such as alkali metal salts (e.g., sodium salts, potassium salts and lithium salts), alkali earth metal salts (e.g., calcium salts and magnesium salts), aluminum salts and iron salts; amine salts such as inorganic amine salts (e.g., ammonium salts) and organic amine salts (e.g., t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts. N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

All salts are intended to be pharmaceutically acceptable salts within the scope of the invention and all salts are considered equivalent to the free forms of the corresponding compounds for purposes of the invention.

Esters

Physiologically/pharmaceutically acceptable esters are also useful as active medicaments. The term "pharmaceutically acceptable esters" embraces esters of the compounds of the present invention, in which hydroxy groups (e.g., in carboxylic acid) have been converted to the corresponding esters and may act as a prodrug which, when absorbed into the bloodstream of a warm-blooded animal, may cleave in such a manner as to release the drug form and permit the drug to afford improved therapeutic efficacy. Such esters can be formed with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms. Further examples are the esters with aliphatic or aromatic acids such as acetic acid or with aliphatic alcohol (e.g., alkyl esters, including methyl, ethyl, propyl, isopropyl, butyl, isobutyl or pentyl esters, and the like) or aromatic alcohols (e.g., benzyl ester).

Esters can be prepared from their corresponding acids or salts by a variety of methods known to those skilled in the art, such as, for example, by first transforming the acid to the acid chloride and then reacting the acid chloride with a suitable alcohol. Other suitable methods for making esters are described in Kemp and Vellaccio, 1980.

Where esters of the invention have a basic group, such as an amino group, the compound can be converted to a salt by reacting it with an acid, and in the case where the esters have an acidic group, such as a sulfonamide group, the compound can be converted to a salt by reacting it with a base. The compounds of the present invention encompass such salts.

Salts and esters of the compounds of the present invention may be prepared by known method by employing appropriate starting materials or intermediate compounds that are readily available and/or are described herein.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The compounds of this invention may be esterified by a variety of conventional procedures including reacting the appropriate anhydride, carboxylic acid or acid chloride with the alcohol group of a compound of this invention. The appropriate anhydride is reacted with the alcohol in the presence of a base to facilitate acylation such as 1,8-bis[dimethylamino]naphthalene or N,N-dimethylaminopyridine. Or, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid in the presence of trifluoroacetic anhydride and, optionally, pyridine, or in the presence of N,N-carbonyldiimidazole with pyridine. Reaction of an acid chloride with the alcohol can be carried out with an acylation catalyst such as 4-DMAP or pyridine.

One skilled in the art would readily know how to successfully carry out these as well as other known methods of etherification of alcohols.

Hydrates

As used herein the terms, "pharmaceutically acceptable hydrate" refer to the compounds of the instant invention crystallized with one or more molecules of water to form a hydrated form.

Prodrugs and Solvates

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of the present invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention or a pharmaceutically acceptable salt, hydrate or solvate of the compound contains a carboxylic acid functional group, a prodrug can comprise an ester formed by the replacement of the hydrogen atom of the acid group with a group such as, for example, (C1-C8)alkyl, (C2-C12)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C1-C2)alkylamino(C2-C3)alkyl (such as 3-dimethylaminoethyl), carbamoyl-(C1-C2)alkyl, N,N-di(C1-C2)alkylcarbamoyl-(C1-C2)alkyl and piperidino-, pyrrolidino- or morpholino(C2-C3)alkyl, and the like.

Similarly, if a compound of the present invention contains an alcohol functional group, a prodrug can be formed by the replacement of the hydrogen atom of the alcohol group with a group such as, for example, (C1-C6)alkanoyloxymethyl, 1-((C1-C6)alkanoyloxy)ethyl, 1-methyl-1-((C1-C6)alkanoyloxy)ethyl, (C1-C6)alkoxycarbonyloxymethyl, N—(C1-C6)alkoxycarbonylaminomethyl, succinoyl, (C1-C6)alkanoyl, α-amino(C1-C4)alkanyl, arylacyl and α-aminoacyl, or α-aminoacyl-α-aminoacyl, where each α-aminoacyl group is independently selected from the naturally occurring L-amino acids, P(O)(OH)2, —P(O)(O(C1-C6)alkyl)2 or glycosyl (the radical resulting from the removal of a hydroxyl group of the hemiacetal form of a carbohydrate), and the like.

If a compound of the present invention incorporates an amine functional group, a prodrug can be formed by the replacement of a hydrogen atom in the amine group with a group such as, for example, R-carbonyl, RO-carbonyl, NRR'-carbonyl where R and R' are each independently (C1-C10)alkyl, (C3-C7)cycloalkyl, benzyl, or R-carbonyl is a natural □-aminoacyl or natural β-aminoacyl, —C(OH)COOY1 wherein Y1 is H, (C1-C6)alkyl or benzyl, —C(OY2)Y3 wherein Y2 is (C1-C4) alkyl and Y3 is (C1-C6)alkyl, carboxy (C1-C6)alkyl, amino(C1-C4)alkyl or mono-N— or di-N,N—(C1-C6)alkylaminoalkyl, —C(Y4)Y5 wherein Y4 is H or methyl and Y5 is mono-N— or di-N,N—(C1-C6)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Stereoisomers, Diastereomers, Enantiomers, Racemates, Tautomers

The compounds of the present invention have asymmetric carbon atoms and can exist in the form of stereoisomers (e.g., diastereomers, optically pure enantiomers) or as racemates or mixtures of two or more stereoisomers of each compound. The term "compound" as used herein embraces all of these forms.

Diastereomers (sometimes called diastereoisomers) are stereoisomers that are not enantiomers. Diastereomerism occurs when two or more stereoisomers of a compound have different configurations at one or more (but not all) of the equivalent (related) stereocenters and are not mirror images of each other. When two diastereoisomers differ from each other at only one stereocenter they are epimers. Each stereocenter gives rise to two different configurations and thus to two different stereoisomers.

Diastereomers differ from enantiomers in that the latter are pairs of stereoisomers which differ in all stereocenters and are therefore mirror images of one another. Enantiomers of a compound with more than one stereocenter are also diastereomers of the other stereoisomers of that compound that are not their mirror image. Diastereomers have different physical properties and different reactivity, unlike enantiomers. Diastereomers of the present invention include, for example (but not limited to) the two diastereomers of compounds 12, 14, 16 and 18, which differ by their stereochemistry in position C3 (steroid numbering) for example.

For purposes of this Specification, "pharmaceutically acceptable tautomer" means any tautomeric form of any compound of the present invention.

It is well understood by those skilled in the art that heterocyclic compounds such as the compounds of the present invention can exist under different tautomeric forms, each tautomeric form being described using a specific formula and a specific name. Herein, the use of the name or formula of one tautomeric form of a compound is meant to refer to and encompass all other tautomeric forms of the same compound.

The purification of enantiomers and the separation of isomeric mixtures of a compound of the present invention may be accomplished by standard techniques known in the art.

Dosages

The dosages in which the compounds of the present invention are administered in effective amounts depend on the nature of the specific active ingredient, the body weight, the age and the requirements of the patient and the mode of application. In general, daily dosages of about 1 mg-5000 mg, preferably 5 mg-500 mg, per day come into consideration.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the present invention can include a series of treatments.

Toxicity and Therapeutic Efficacy

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

The present invention also encompasses kits comprising the compounds of the present invention. For example, the kit can comprise one or more compounds inhibiting the growth of electron transport-deficient microbes (e.g., SCVs) or potentiating the antimicrobial activity of aminoglycoside antibiotics against normal bacterial strains (e.g., staphylococci). The kit may optionally include one or more control sample(s). The compounds or agents can be packaged in a suitable container. The kit can further comprise instructions for using the kit.

The present invention also relates to methods for preparing the above-mentioned compounds.

The present invention is illustrated in further details by the following non-limiting examples.

Example 1

Chemistry

All moisture-sensitive reactions were performed in an inert, dry atmosphere of argon in flame-dried glassware. Air-sensitive liquids were transferred via syringe or cannula through rubber septa. Reagent grade solvents were used for extractions and flash chromatography. THF was distilled from sodium/benzophenone under argon; methanol was distilled from magnesium under argon. All other solvents purchased from commercial sources were used without further purification. Tomatidine hydrochloride (3) was purchased from Molekula. All other reagents were generally purchased from Aldrich and used with no further purification.

Reactions were monitored by analytical thin-layer chromatography (Canadian Life Science, TLC, GLASS plates SIL 60 G-25 UV 254). The plates were visualized first with UV illumination followed by heating with ceric ammonium molybdate (CAM) [1% (w/v) ammonium cerium sulphate, 2.5% (w/v) molybdenum trioxide, 1:9 $H_2SO_4/H_2O$]. Flash column chromatography was performed manually on Silia-Flash® P60 silica. The solvent compositions reported for all chromatographic separations are on a volume/volume (v/v) basis.

High-pressure liquid chromatography (HPLC) was performed on an Agilent 1100™ apparatus using an ACE C18 column, 250×21.2 mm, with 5 μm silica and 15.5% carbon load.

NMR spectra were recorded at room temperature on a Bruker Spectrospin 300™ spectrometer at 300 MHz ($^1H$) and 75 MHz ($^{13}C$), or on a Varian Unity Inova™ at 600 HMz ($^1H$) and 150 MHz ($^{13}C$). $^1H$ NMR spectra are reported in parts per million (ppm) on the δ scale relative to the residual signals of chloroform (δ 7.26 ppm) or methanol (δ 3.31 ppm) as an internal standard with the following multiplicity—s: singlet; d: doublet; t: triplet; q: quartet; quint: quintet; m: multiplet). $^{13}C$ NMR spectra are reported in ppm on the δ scale relative to $CDCl_3$ (δ 77.0 ppm) or $CD_3OD$ (δ 49.0 ppm). High-resolution mass spectrometry (HRMS) was performed on a Maxis (Bruker) Q-TOF.

Example 2

General Procedure for Synthesis of Boc-diaminoalkanes (A)

Boc-alkanediamines 38 and 40 were synthesized as reported by Jensen et al.

Example 3

General Procedure for Reductive Amination of 3β-acetoxy-5-alpha-pregnan-20-one (B)

Reductive amination with pregnanolone acetate derivatives were synthesized as reported by Xie et al, 2001.

Example 4

General Method for Acidic Deprotections (D)

In a 25 mL round bottom flash equipped with a condenser, the starting material was solubilized in 5 mL anhydrous MeOH. To this solution was added a solution of 0.9 mL acetyl chloride in 6 mL anhydrous MeOH. The reaction heated to reflux for 1 h, monitored by TLC. The reaction was allowed to cool at room temperature, then the solvent was removed in vacuo to yield the desired compound.

Example 5

Intermediate N-Formyl Tomatidine (4)

In a 250 mL round flask, tomatidine hydrochloride (3) (200 mg, 0.44 mmol, 1.0 eq) was suspended in dry THF (20 mL) then acetic formic anhydride (380 mg, 4.42 mmol, 10.0 eq) was added, followed by DIPEA (390 µL, 2.20 mmol, 5.0 eq). The reaction was stirred for 15 minutes, then monitored by TLC (50% EtOAc/Hexanes, CAM stain, Rf=0.23 for mono-formylated compound, 0.49 for diformylated compound). The volatiles were removed by evaporation under reduced pressure. The compound was then diluted in a mixture of 125 mL EtOH and 50 mL aqueous $NaHCO_3$ buffer (pH=9.5) and stirred for one week, monitored by TLC until the complete disappearance of the diformylated compound. EtOH was then evaporated, and the resulting aqueous phase was extracted with EtOAc (3×25 mL). The combined organic phases were dried on anhydrous magnesium sulphate then evaporated under reduced pressure.

The crude product was purified by flash chromatography (25% EtOAc/Hexanes) to give 155 mg (79%) of the desired compound 4 as a white solid (m.p. 184-187° C.).

$^1$H NMR (600 MHz, $CDCl_3$) δ (ppm) 8.41 (s, 1H), 4.29 (d, 1H, J=11.5 Hz), 4.13 (dd., 1H, $J_1$=7.3 Hz, $J_2$=15.5 Hz), 3.58 (quint, 1H, J=4.7 Hz), 2.65 (t, 1H, J=11.5), 2.54 (quint, 1H, J=7.1 Hz), 1.98 (quint, 1H, J=5.28 Hz) 1.87 (d, 1H, J=13.7 Hz), 1.82-1.72 (m, 3H), 1.72-1.63 (m, 3H), 1.61-1.45 (m, 7H), 1.40 (d, 1H, J=13.0 Hz), 1.38-1.22 (m, 8H), 1.15 (dt, 1H, $J_1$=12.3 Hz, $J_2$=3.9 Hz), 1.12-1.06 (m, 2H), 1.05 (d, 3H, J=6.8 Hz), 0.95 (dt, 1H, $J_1$=13.7 Hz, $J_2$=3.6 Hz), 0.91 (d, 3H, J=5.9 Hz), 0.89-0.84 (m, 1H), 0.82 (s, 6H), 0.64 (dt, 1H, $J_1$=11.39, $J_2$=3.6 Hz).

$^{13}$C NMR (75.5 MHz, $CDCl_3$) δ (ppm) 158.9, 97.8, 78.5, 72.1, 62.3, 55.8, 54.3, 44.8, 40.2, 38.1, 36.9, 36.8, 35.5, 35.0, 32.2, 31.4, 30.7, 29.7, 29.2, 28.5, 27.5, 21.0, 18.9, 17.0, 15.3, 12.3. HRMS calculated for $C_{28}H_{45}O_3NNa^+$: 466.3292, found: 466.3308 ($MNa^+$).

Example 6

N-formyl-3-oxotomatidine (9)

In a 10 mL round bottom flask, N-formyltomatidine 4 (50 mg, 0.113 mmol, 1.0 eq) and Dess-Martin periodinane (95 mg, 0.225 mmol, 2.0 eq) were stirred in 6.5 mL DCM. The reaction was monitored by TLC (50% AcOEt/Hexanes, Rf: 0.24). Upon completion, the reaction was quenched for 30 minutes with $Na_2S_2O_3$ (0.2M), then extracted 3× with EtOAc. The combined organic phases were washed with brine, dried on anhydrous magnesium sulphate then evaporated under reduced pressure. The crude compound was purified by flash chromatography (50% EtOAc/Hexanes) to yield 34 mg (68%) of the desired compound.

$^1$H NMR (300 MHz, $CDCl_3$) δ (ppm) 8.46 ppm (s, 1H), 4.32 (d, 1H, J=12.8 Hz), 4.17 (quad, 1H, J=8.9 Hz), 2.69 (t, 1H, J=12.6 Hz), 2.58 (quint, 1H, J=6.6 Hz), 2.52-2.24 (m, 3H), 2.16-2.11 (m, 1H), 2.11-1.98 (m, 3H), 1.91 (d, 1H, J=14.0 Hz), 1.86-1.68 (m, 4H), 1.69-1.42 (m, 7H), 1.40-1.20 (m, 7H), 1.19-1.12 (m, 2H), 1.09 (d, 3H. J=7.1 Hz), 1.05 (s, 2H), 0.94 (d, 4H, J=5.5 Hz), 0.88 (s, 3H), 0.77 (dt, 1H, $J_1$=12.6 Hz, $J_2$=4.8 Hz).

Example 7

Intermediate N-Formyl-3-aminotomatidine (11)

In a 25 mL round flask, 44 mg N-formyl-3-oxotomatidine (9) (0.1 mmol) was dissolved in methanol (6 mL) along with ammonium acetate ($NH_4OAc$) (77 mg, 1.0 mmol, 10 eq). The pH was adjusted to 6 with acetic acid, sodium cyanoborohydride ($NaBH_3CN$) (6.9 mg, 0.11 mmol, 1.1 eq) was added and the reaction was refluxed overnight until complete as monitored by TLC (10% MeOH/AcOEt with 0.5% $NEt_3$, Rf: 0). Solvents were removed under reduced pressure, and the solid was suspended in water. The pH was adjusted to 8 with saturated aqueous $NaHCO_3$. The mixture was extracted with 3× EtOAc, and the combined organic fractions were washed with brine, dried on anhydrous magnesium sulphate and evaporated under reduced pressure. The crude compound was purified by flash chromatography (10% MeOH/89% EtOAc/1% $NEt_3$) to yield 21 mg (48%) of the desired compound 11.

$^1$H NMR (300 MHz, $CDCl_3$) δ (ppm) 8.40 (s, 1H), 5.91, (broad s, 2H), 4.28 (d, 1H, J=11.5 Hz), 4.12 (m., 1H), 2.86 (quint, 1H, J=7.1 Hz), 2.65 (t, 1H, J=11.5), 2.53 (quint, 1H, J=7.1 Hz), 2.04-1.92 (m, 3H) 1.90-1.82 (m, 1H), 1.80-1.42 (m, 11H), 1.38-1.18 (m, 9H) 1.17-1.06 (m, 2H), 1.04 (d, 3H, J=7.1 Hz), 0.90 (d, 4H, J=6.2 Hz), 0.81 (s, 6H), 0.69-0.57 (m, 1H).

Example 8

N-Boc-1,2-diaminoethane (38)

Following procedure A, 770 µL diaminoethane was used to yield 76 mg (41%) of compound 38 as a colorless oil.

$^1$H NMR (300 MHz, $CDCl_3$) δ (ppm) 5.28-5.11 (broad s, 1H), 3.13 (q, 2H, J=5.7 Hz), 2.76 (t, 2H, J=5.7 Hz), 2.47-2.20 (broad s, 2H), 1.38 (s, 9H).

Example 9

Intermediate N-Formyl-3-(N-Boc-aminoethyl)aminotomatidine (13)

Following the procedure used for the synthesis of compound 11, 110 mg 9 (0.25 mmol), compound 38 (BocNH$(CH_2)_2NH_2$) (200 mg, 1.25 mmol, 5 eq) and sodium cyanoborohydride ($NaBH_3CN$) (17 mg, 0.27 mmol, 1.1 eq) were used to yield 130 mg (85%) of compound 13. (RF: 0.05 in 10% MeOH/AcOEt with 0.5% $NEt_3$) $^1$HNMR shows the presence of residual starting diamine, which was removed in the next step.

$^1$H NMR (300 MHz, $CDCl_3$) δ (ppm) 8.39 (s, 1H), 5.02, (s large, 1H), 4.28 (d, 1H, J=11.5 Hz), 4.12 (m, 1H), 3.24-3.15 (m, 2H), 2.77-2.69 (m, 2H), 2.64 (m, 1H) 2.54 (m, 1H), 2.44 (m, 1H), 2.04-1.46 (m, 18H) 1.43 (s, 12H), 1.33-1.15 (m, 14H), 1.04 (d, 3H, J=6.9 Hz), 0.90 (d, 3H, J=5.7 Hz), 0.87-0.82 (m, 2H), 0.81 (s, 3H), 0.78 (s, 3H), 0.69-0.57 (m, 1H).

Example 10

3-(N-aminoethyl)-aminotomatidine hydrochloride (14)

Following procedure D, 130 mg of compound 13 were deprotected in quantitative yield (Rf: 0 in 10% MeOH/

AcOEt with 0.5% NEt₃). The crude compound was purified preparative HPLC to yield 48 mg (38%) of desired compound 14. The HPLC elution parameters were as follow (percentage of acetonitrile in water): 0 min, 20%; 2 min, 20%; 27 min, 95%; 32 min, 95%.

$^1$H NMR (300 MHz, CD3OD) δ (ppm) 4.36 (m, 1H), 3.18-3.03 (m, 2H), 2.89 (t, 1H, J=10.7 Hz) 2.20 (m, 1H), 2.08-1.90 (m, 3H), 1.80-1.50 (m, 18H), 1.45-1.14 (m, 12H) 1.09 (d, 3H, J=7.1 Hz), 0.69 (d, 3H, J=6.7 Hz), 0.89 (s, 3H), 0.85 (s, 4H), 0.83-0.66 (m, 2H).

$^{13}$C NMR (75.5 MHz, CD3OD) δ (ppm) 96.1, 81.1, 61.6, 57.6, 56.3, 55.4, 53.7, 44.5, 41.1, 40.8, 40.7, 39.5, 38.6, 35.7, 35.3, 34.8, 31.7, 31.4, 30.7, 28.9, 28.0, 25.8, 25.3, 24.4, 20.6, 17.2, 15.9, 11.1, 10.4.

HRMS calculated for $C_{29}H_{52}ON_3^+$: 458.4105, found: 458.4105 (MH⁺).

Example 11

N-Boc-1,4-diaminobutane (40)

Following procedure A, 1.16 mL diaminobutane was used to yield 171 mg (79%) of compound 40 as a colorless oil.

$^1$H NMR (300 MHz, CDCl₃) δ (ppm) 4.94 (broad s, 1H), 3.04 (broad s, 4H), 2.69 (broad s, 2H), 1.45 (broad s, 4H), 1.36 (s, 9H).

Example 12

Intermediate N-Formyl-3-(N-Boc-aminobutyl)aminotomatidine (15)

Following the procedure used for the synthesis of compound 11, 27 mg 9 (0.060 mmol), compound 40 (BocNH(CH₂)₄NH₂) (57 mg, 0.30 mmol, 5 eq) and sodium cyanoborohydride (NaBH₃CN) (4.1 mg, 0.066 mmol, 1.1 eq) were used to yield 16 mg (44%) of compound 15. (Rf: 0.07 in 10% MeOH/AcOEt with 0.5% NEt₃)

$^1$H NMR (300 MHz, CDCl3) δ (ppm) 8.40 (s, 1H), 5.02, (broad d, 1H), 4.28 (d, 1H, J=11.5 Hz), 4.12 (m, 1H), 3.14-3.04 (s large, 3H), 2.80-2.50 (m, 5H), 2.42 (m, 1H), 2.04-1.93 (m, 2H), 1.86 (d, 1H, J=12.8 Hz), 1.79-1.62 (m, 5H), 1.60-1.46 (m, 12H), 1.42 (s, 12H), 1.35-1.10 (m, 10H), 1.04 (d, 5H, J=6.9 Hz), 0.90 (d, 4H, J=5.8 Hz), 0.81 (s, 3H), 0.78 (s, 3H), 0.69-0.57 (m, 1H).

Example 13

3-(N-aminobutyl)-aminotomatidine hydrochloride (16)

Following procedure D, 16 mg of compound 15 were deprotected in quantitative yield. (RF: 0 in 10% MeOH/AcOEt with traces if NEt₃) The crude compound was purified by preparative HPLC to yield 15 mg (100%) of desired compound 16. The HPLC elution parameters were as follow (percentage of acetonitrile in water): 0 min, 5%; 2 min, 5%; 27 min, 95%; 32 min, 95%.

$^1$H NMR (300 MHz, CD₃OD) δ (ppm) 4.37 (q, 1H, J=4.8 Hz), 3.38 (broad s, 1H), 3.18-3.15-2.87 (m, 7H), 2.20 (t, 1H, J=6.5 Hz), 2.08-1.82 (m, 6H) 1.82-1.63 (m, 11H), 1.61-1.50 (m, 5H), 1.44-1.14 (m, 12H), 1.08 (d, 4H, J=7.4 Hz), 0.96 (d, 3H, J=6.5 Hz), 0.89 (s, 3H), 0.87 (s, 4H), 0.79-0.69 (m, 1H).

$^{13}$C NMR (75.5 MHz, CD₃OD) δ (ppm) 96.5, 80.7, 61.8, 57.1, 55.4, 54.9, 53.8, 45.2, 44.6, 43.6, 41.0, 39.6, 38.6, 36.2, 35.3, 34.8, 31.7, 31.5, 30.8, 29.1, 28.5, 28.0, 26.1, 25.4, 24.5, 24.3, 22.7, 22.3, 20.6, 17.4, 15.9, 13.4, 11.0.

HRMS calculated for $C_{31}H_{57}ON_3^{2+}$: 243.7245, found: 243.7253.

Example 14

Intermediate N-Formyl-3-(aminohexyl)aminotomatidine (17)

Following the procedure used for the synthesis of compound 11, 20 mg 9 (0.045 mmol), hexamethylenediamine (BocNH(CH₂)₆NH₂) (30 μL, 0.225 mmol, 5 eq) and sodium cyanoborohydride (NaBH₃CN) (3.2 mg, 0.050 mmol, 1.1 eq) were used to yield 11 mg (46%) of compound 17 (Rf: 0 in 10% MeOH/AcOEt with 0.5% NEt₃).

$^1$H NMR (300 MHz, CDCl₃) δ (ppm) 4.32-4.25 (m, 1H), 4.18-4.08, (m, 1H), 3.08 (broad s, 3H), 2.74-2.49 (m, 5H), 2.03-1.93 (m, 2H) 1.91-1.81 (m, 1H), 1.80-1.70 (m, 2H), 1.70-1.41 (m, 11H), 1.39-1.09 (m, 14H), 1.05 (d, 3H, J=7.0 Hz), 0.90 (d, 3H, J=5.4 Hz), 0.87-0.82 (m, 2H), 0.82 (s, 3H), 0.80 (s, 3H), 0.69-0.59 (m, 1H).

Example 15

3-(N-aminohexyl)-aminotomatidine hydrochloride (18)

Following procedure D, 11 mg of compound 17 were deprotected in quantitative yield (Rf: 0 in 10% MeOH/AcOEt with 0.5% NEt₃). The crude compound was purified by preparative HPLC to yield 12.5 mg (100%) of compound 18. The HPLC elution parameters were as follow (percentage of acetonitrile in water): 0 min, 20%; 2 min, 20%; 27 min, 95%; 32 min, 95%.

$^1$H NMR (300 MHz, CD3OD) δ (ppm) 4.37 (m, 1H), 3.39 (m, 1H), 3.16-3.05 (m, 1H) 3.04-2.82 (m, 6H), 2.20 (t, 1H, J=6.7 Hz), 2.08-1.95 (m, 3H), 1.90-1.82 (m, 3H), 1.80-1.52 (m, 15H), 1.50-1.16 (m, 18H), 1.09 (d, 3H, J=6.4 Hz), 1.06-0.99 (m, 3H), 0.96 (d, 3H, J=6.8 Hz), 0.90 (s, 3H), 0.88 (s, 4H), 0.75-0.60 (m, 1H).

$^{13}$C NMR (75.5 MHz, CD₃OD) δ (ppm) 96.1, 81.0, 61.6, 57.0, 55.5, 53.8, 53.5, 44.5, 44.2, 40.8, 39.5, 38.8, 35.6, 34.7, 31.5, 31.3, 31.2, 30.8, 29.0, 28.2, 27.6, 26.9, 25.9, 25.5, 25.4, 22.2, 20.2, 17.2, 15.8, 13.1, 10.3.

HRMS calculated for $C_{33}H_{61}ON_3^{++}$: 257.7402, found: 257.7406.

Example 16

Intermediate 3β-Acetoxy-20-butylamino-5α-pregnane (47)

Following procedure B, 50 mg of compound 28 (0.14 mmol), 137 μL (1.39 mmol, 10 eq) of butylamine and 10 mg of sodium cyanoborohydride (0.15 mmol, 1.1 eq) were converted to 24.2 mg (41%) of desired product (Rf: 0.33 in 10% MeOH/AcOEt with 0.5% NEt₃).

$^1$H NMR (300 MHz, CDCl₃) δ (ppm) 4.67 (sept, 1H, J=5.9 Hz), 2.75-2.65 (m, 1H), 2.60-2.52 (m, 1H), 2.50-2.41 (m, 1H), 2.01 (s, 3H), 2.00-1.84 (m, 5H), 1.82-1.44 (m, 11H, 1.40-1.10 (m 12H), 1.09 (d, 5H, J=6.5 Hz), 1.07-0.95 (m, 3H), 0.91 (t, 3H, J=7.4 Hz), 0.81 (s, 3H), 0.65 (s, 4H).

Example 17

3β-Hydroxy-20-butylamino-5α-pregnane hydrochloride (48)

Following procedure D, 15 mg of compound 47 (0.036 mmol), were converted to 13.5 mg (100%) of compound 48 (Rf: 0.05 in 10% MeOH/AcOEt with 0.5% NEt₃).

¹H NMR (300 MHz, CD3OD) δ (ppm) 3.48 (m, 1H), 3.20 (m, 1H), 2.97 (m, 2H), 1.97-1.84 (m, 2H), 1.79-1.07 (m, 23H), 1.01-0.85 (m, 5H), 0.81 (s, 3H), 0.72 (s, 3H), 0.69-0.61 (m, 1H).

¹³C NMR (75.5 MHz, CD$_3$OD) δ (ppm) 70.4, 57.4, 56.0, 54.1, 52.7, 44.7, 42.7, 42.6, 39.1, 37.4, 36.8, 35.2, 35.2, 31.7, 30.7, 28.4, 27.9, 25.8, 23.8, 20.8, 19.5, 15.1, 12.5, 11.3, 10.9.

HRMS calculated for $C_{25}H_{46}ON^+$: 376.3574, found: 376.3578 (MH$^+$).

Example 18

Intermediate
3β-Acetoxy-20-isopentylamino-5α-pregnane (49)

Following procedure B, 100 mg of compound 28 (0.28 mmol), 200 μL (1.72 mmol, 6.2 eq) of isopentylamine and 18 mg of sodium cyanoborohydride (0.29 mmol, 1.05 eq) were converted to 46 mg (41%) of compound 49 (Rf: 0.36 in 10% MeOH/AcOEt with 0.5% NEt$_3$).

¹H NMR (300 MHz, CDCl3) δ (ppm) 5.62 (s large, 2H), 4.65 (sept, 1H, J=6.2 Hz), 3.26-2.57 (m, 2H), 1.99 (s, 5H), 1.85-1.37 (m, 11H), 1.35-1.15 (m, 8H), 1.12 (d, 2H, J=6.3 Hz), 1.09-0.96 (m, 3H), 0.92 (d, 1H, J=6.3 Hz), 0.89 (d, 6H, J=6.4 Hz), 0.790 (s 3H), 0.69-0.55 (m, 4H).

Example 19

3β-Hydroxy-20-isopentylamino-5α-pregnane hydrochloride (50)

Following procedure D, 46 mg of compound 49 (0.11 mmol), were converted to 48 mg (100%) of compound 50 (Rf: 0.07 in 10% MeOH/AcOEt with 0.5% NEt$_3$).

¹H NMR (300 MHz, CD3OD) δ (ppm) 3.49 (m, 1H), 2.98 (m, 1H), 1.89-1.45 (m, 12H), 1.45-1.00 (m, 17H), 0.96 (d, 6H, J=6.4 Hz), 0.91-0.86 (m, 2H), 0.82 (s, 3H), 0.72 (s, 3H), 0.70-0.63 (m, 2H).

¹³C NMR (75.5 MHz, CD$_3$OD) δ (ppm) 70.4, 55.6, 54.4, 54.0, 52.0, 44.8, 42.3, 37.5, 37.4, 36.8, 35.2, 34.4, 31.7, 30.7, 28.4, 25.9, 23.5, 23.4, 21.4, 21.2, 20.6, 14.3, 11.5, 11.3.

HRMS calculated for $C_{26}H_{48}ON^+$: 390.3730, found: 390.3733 (MH$^+$).

Figure 1A:
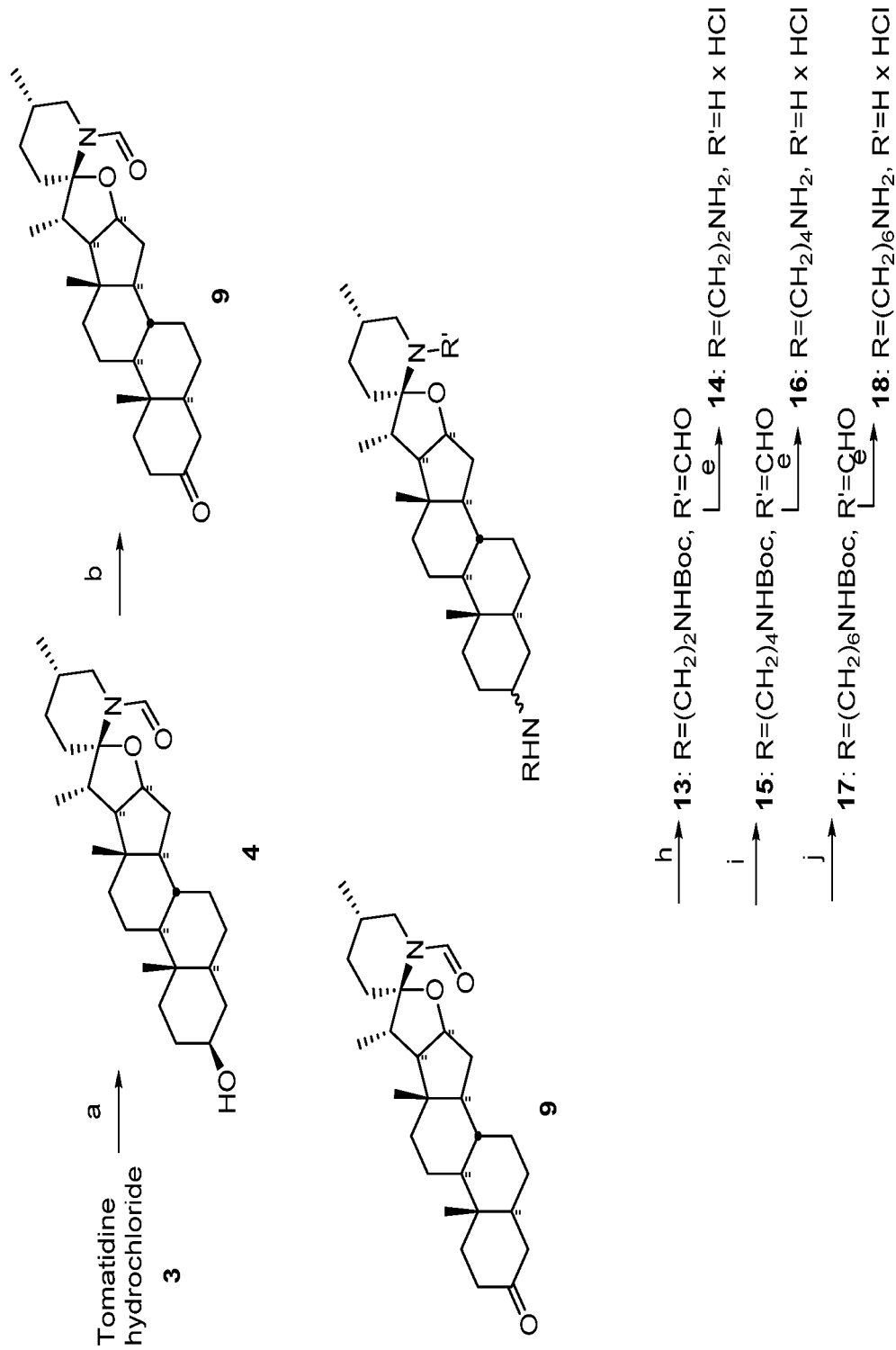
FIGS. 1A-B presents Scheme 1. Reagents and conditions: a) i-acetic formic anhydride, DIPEA, THF, rt; ii-EtOH, NaHCO$_3$ buffer pH=9.5, rt, 79% (2 steps); b) Dess-Martin periodinane, DCM, rt, 68%; e) HCl, MeOH, reflux, quant.; h) BocNH(CH$_2$)$_2$NH$_2$, NaBH$_3$CN, MeOH, pH=6, reflux, 89%; i) BocNH(CH$_2$)$_4$NH$_2$, NaBH$_3$CN, MeOH, pH=6, reflux, 44%; j) BocNH(CH$_2$)$_6$NH$_2$, NaBH$_3$CN, MeOH, pH=6, reflux, 46% (FIG. 1A). Scheme 2. Reagents and conditions: a) H$_2$, Pd/C, 200 PSI, rt, quant.; g) amine, NaBH$_3$CN, MeOH, THF, pH6 Reflux, 40-70%; f) HCl, THF, rt, 75% (FIG. 1B).
Figure 1B:
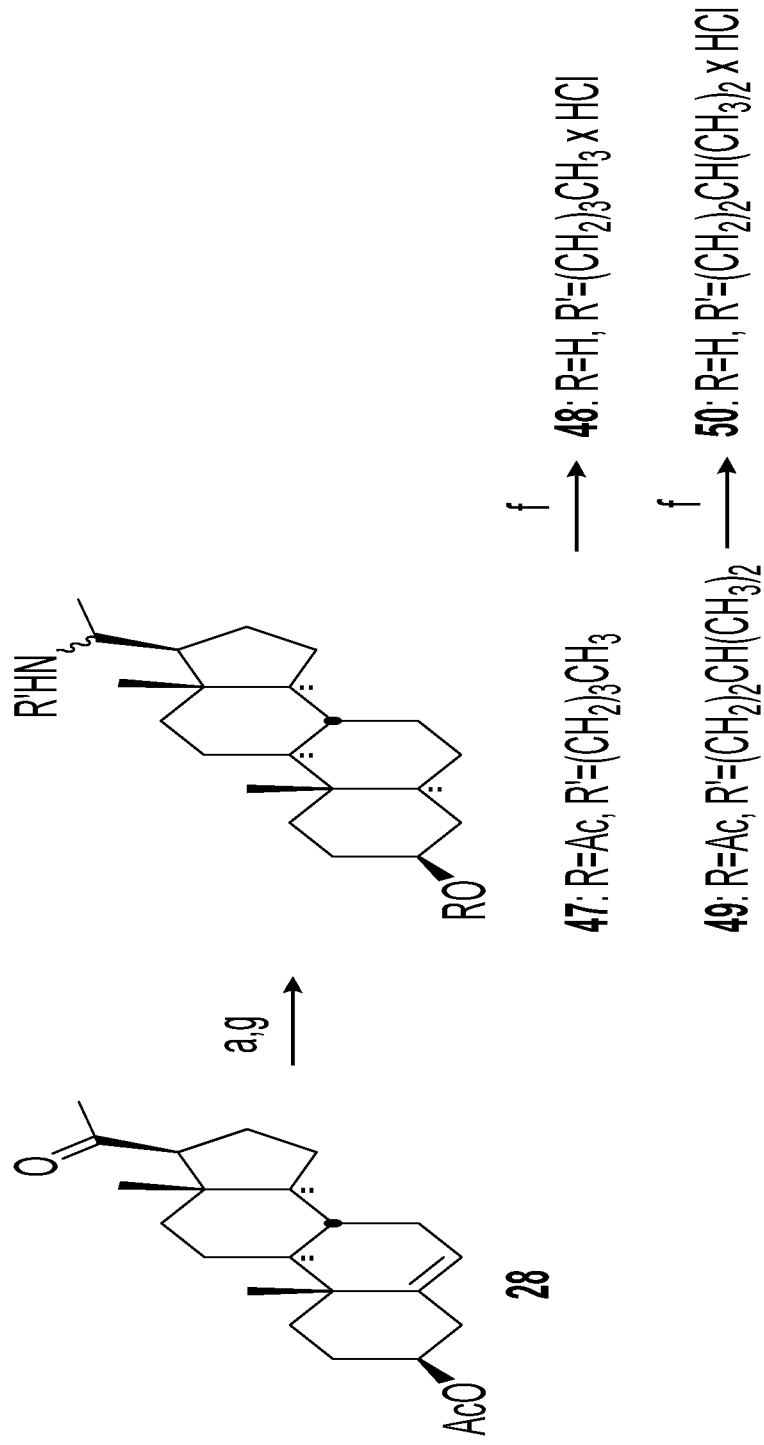

The syntheses of compounds described in Examples 1 to 15 are also presented in FIGS. 1A and B.

Example 20

Antibacterial Activity of Tomatidine and Derivatives Alone Against a Normal *Staphylococcus aureus* Strain (ATCC 29213) or a *Staphylococcus aureus* SCV Strain (hemB), or in Combination with an Aminoglycoside Against Normal *S. aureus* ATCC 29213

Method. The minimal inhibitory concentrations (MICs), (i.e. lowest concentration of an antimicrobial that will inhibit the visible growth of a microorganism after incubation), of test compounds were determined against the normal or SCV strains of bacterial species from the Firmicutes phylum. Briefly, MICs were determined using the microdilution method in 96-well plates (Clinical and Laboratory Standards Institute (CLSI), 2011). Bacteria were inoculated at ~10$^5$-10$^6$ CFU/mL and incubated at 35° C. for 20 h (normal strains) or 48 h (SCVs) in brain heart infusion (BHI) broth in order to allow SCVs to reach maximal growth as previously described (Mitchell et al., 2012). Then OD$_{595\ nm}$ was read on a microplate reader. The MICs obtained against the quality control strain *S. aureus* ATCC 29213 (normal strain) for the compounds tested were similar in BHI and in cation-adjusted Mueller-Hinton broth (CAMHB) showing that the type of cultivation medium did not influence results. In this example the range of compound concentrations tested was 0.03 to 64 μg/ml using doubling increments. Strain *Staphylococcus aureus* NewbouldΔhemB (hemB) was also used in the experiments and is a laboratory-derived stable SCV created by the insertion of the macrolide resistance gene ermA in the hemB gene of this strain to create the SCV phenotype (defective electron transport chain and respiratory deficiency) through inactivation of hemin biosynthesis (Brouillette et al., 2004).

Results.

The various antibacterial activities of the test compounds against *Staphylococcus aureus* ATCC 29213, alone or in combination with gentamicin, and alone against the SCV strain hemB are reported in Table 1. The MIC of gentamicin used alone against *S. aureus* ATCC 29213 is 0.5 μg/mL. In Table 1, the potentiation fold of compounds is defined as the ratio of the MIC of gentamicin alone and the MIC of gentamicin in combination with the test compound used at 8 μg/mL (except for compounds 14 and 16 that were used at 4 μg/mL).

TABLE 1

Biological activities of tomatidine analogs against *S. aureus* of the normal and SCV phenotypes alone or in combination with an aminoglycoside.

| Compound | MIC vs ATCC29213 (μg/ml)$^a$ | Combination MIC vs ATCC29213 (potentiaton fold with gentamicin)$^b$ | MIC vs SCV$^c$ (μg/ml)$^a$ |
|---|---|---|---|
| 3 | >64 | 0.06 (8x) High | 0.06 High |

TABLE 1-continued

Biological activities of tomatidine analogs against *S. aureus* of the normal and SCV phenotypes alone or in combination with an aminoglycoside.

| Compound | | MIC vs ATCC29213 (μg/ml)[a] | Combination MIC vs ATCC29213 (potentiaton fold with gentamicin)[b] | MIC vs SCV[c] (μg/ml)[a] |
|---|---|---|---|---|
| 4 | | >64 | 0.25 (2x) Low | >8 Low |
| 14 | | 8-16 Active | 0.06-0.12 (4-8x) Moderate-high | 0.5-1 Moderate |
| 16 | | 16 Active | 0.06-0.12 (4-8x) Moderate-high | 0.5 Moderate |
| 18 | | 32 | 0.12-0.25 (2-4x) Moderate | 1 Moderate |
| 48 | | 64 | 0.06 (8x) High | 4-8 Moderate |

TABLE 1-continued

Biological activities of tomatidine analogs against *S. aureus* of the normal and SCV phenotypes alone or in combination with an aminoglycoside.

| Compound | MIC vs ATCC29213 (μg/ml)[a] | Combination MIC vs ATCC29213 (potentiaton fold with gentamicin)[b] | MIC vs SCV[c] (μg/ml)[a] |
|---|---|---|---|
| 50 [structure] | >64 | 0.12 (4x) Moderate | >8 Low |

Compounds 14 to 18, 48 and 50 are racemic mixtures.
[a]Compound tested alone;
[b]The potentiation fold of compounds is defined as the ratio of the MIC of gentamicin alone and the MIC of gentamicin in combination with the compound used at 8 μg/mL (except for compounds 14 and 16 that were used at 4 μg/mL); and
[c]Activity of the compounds against the SCV strain NewbouldΔhemB (MIC = ≥8 μg/mL: low activity, MIC = 0.5-4 μg/mL: moderate activity, MIC = 0.06-0.25 μg/mL: high activity).

Interestingly, certain compounds, notably compounds 14, 16 and 18 showed some antibacterial activities of their own against *S. aureus* ATCC 29213 (minimal inhibitory concentrations [MICs] of 8-32 μg/ml), a property that is not seen with tomatidine hydrochloride salt (3) showing a poor activity against normal non-SCV strains (MIC>64 μg/ml in Table 1). In addition to their own antibacterial activity, Compounds 14 and 16 retain the ability to potentiate the activity of aminoglycosides against the normal *S. aureus* strain (ATCC 29213) and their antibacterial activity against the *S. aureus* SCV. Also noteworthy, the solubility of Compound 14 in DMSO is increased by more than tenfold (26 mg/ml in DMSO) compared to that of tomatidine hydrochloride salt (2 mg/ml in DMSO). Besides, among the tested compounds, Compounds 48 and 50 maintained a strong or moderate synergy with gentamicin against *S. aureus* ATCC 29213 despite the absence of the spiroaminoketal moiety found in tomatidine hydrochloride salt. These compounds thus represent a scaffold that is distinct from that of tomatidine but that still potentiate the activity of aminoglycoside agents.

Also in addition to that seen in Table 1 with gentamicin, Table 2 reports the activity of Compound 14 in combination with a variety of antibiotics of the aminoglycoside class showing that a combination with any aminoglycoside leads to an important synergy against a normal *S. aureus* strain.

TABLE 2

Biological activities of Compound 14 against *S. aureus* of the normal phenotype (ATCC 29213) in combination with an aminoglycoside (tobramycin, streptomycin, kanamycin or amikacin).

| | MIC of aminoglycoside (μg/mL) against *S. aureus* ATCC 29213 | | Potentiation |
|---|---|---|---|
| Aminoglycoside alone | | In combination with Compound 14 used at 4 μg/mL | fold with Compound 14[a] |
| Tobramycin | 1 | 0.125 | 8 |
| Streptomycin | 4-8 | 1 | 4-8 |
| Kanamycin | 4 | 0.25 | 16 |
| Amikacin | 4 | 0.25 | 16 |

TABLE 2-continued

Biological activities of Compound 14 against *S. aureus* of the normal phenotype (ATCC 29213) in combination with an aminoglycoside (tobramycin, streptomycin, kanamycin or amikacin).

| | MIC of aminoglycoside (μg/mL) against *S. aureus* ATCC 29213 | | Potentiation |
|---|---|---|---|
| Aminoglycoside alone | | In combination with Compound 14 used at 4 μg/mL | fold with Compound 14[a] |

[a]The potentiation fold is defined as the ratio of the MIC of the aminoglycoside alone and the MIC of the aminoglycoside in combination with Compound 14 used at 4 μg/mL.

Example 21

Antibacterial Effect of Compound 14 on Normal Antibiotic-Resistant *Staphylococcus aureus* (MRSA) when Used Alone or in Combination with Gentamicin or with Kanamycin and Cefalexin The potentiation effects of Compound 14 against antibiotic resistant strains such as methicillin-resistant *Staphylococcus aureus* (MRSA), when used in combination with gentamicin, or with kanamycin together with cefalexin (also named cephalexin), are reported in Table 3. The MICs were determined following a procedure similar to that described in Example 20. In the present Example the range of compound concentrations tested, using doubling increments, was 0.03 to 64 μg/ml for Compound 14 and up to 1024 μg/ml for gentamicin (GEN), kanamycin (KAN) and cefalexin (CEF) when these compounds were used alone. Compound 14 (Cpd 14) was used at a fixed concentration of 4 μg/ml when added to other antibiotics. The combination of CEF and KAN was used in a 3:2 ratio and doubling increments were used to test the antibacterial activity against MRSA in the absence or presence of Compound 14.

Results:
Table 3 reports the antibacterial activity of Compound 14 on MRSA strains (MIC of 16 μg/ml when used alone). This activity is similar to that determined against the methicillin-susceptible strain *S. aureus* ATCC 29213 (Table 1). Table 3 also reports the 4 to 8-fold increase of gentamicin activity in the presence of Compound 14 against MRSA strains which is also similar to that seen with methicillin-susceptible strains like *S. aureus* ATCC 29213 (Table 1). Noteworthy, all the tested MRSA strains were resistant to cefalexin (MIC 256 µg/ml) and two of the strains were also resistant to kanamycin (MICs of 256 and >1024 µg/ml). The combination of an antibiotic of the beta-lactam class such as cefalexin and an aminoglycoside such as kanamycin usually results in a synergy (Davis, 1982), and Table 3 reports this gain of inhibitory activity when both compounds are tested together in a 3:2 ratio. Interestingly, the further addition of Compound 14 to this cefalexin:kanamycin combination resulted in a major increase in activity, especially against MRSA strains resistant to both compounds (potentiation fold of 32, Table 3).

(BHIA) for colony-forming unit (CFU) determinations (i.e., viable bacterial counts). Plates were incubated for 24 h at 35° C. The antibacterial activities of these molecules as a function of time are presented in FIG. 2. It represents the results of three independent experiments.

Figure 2:
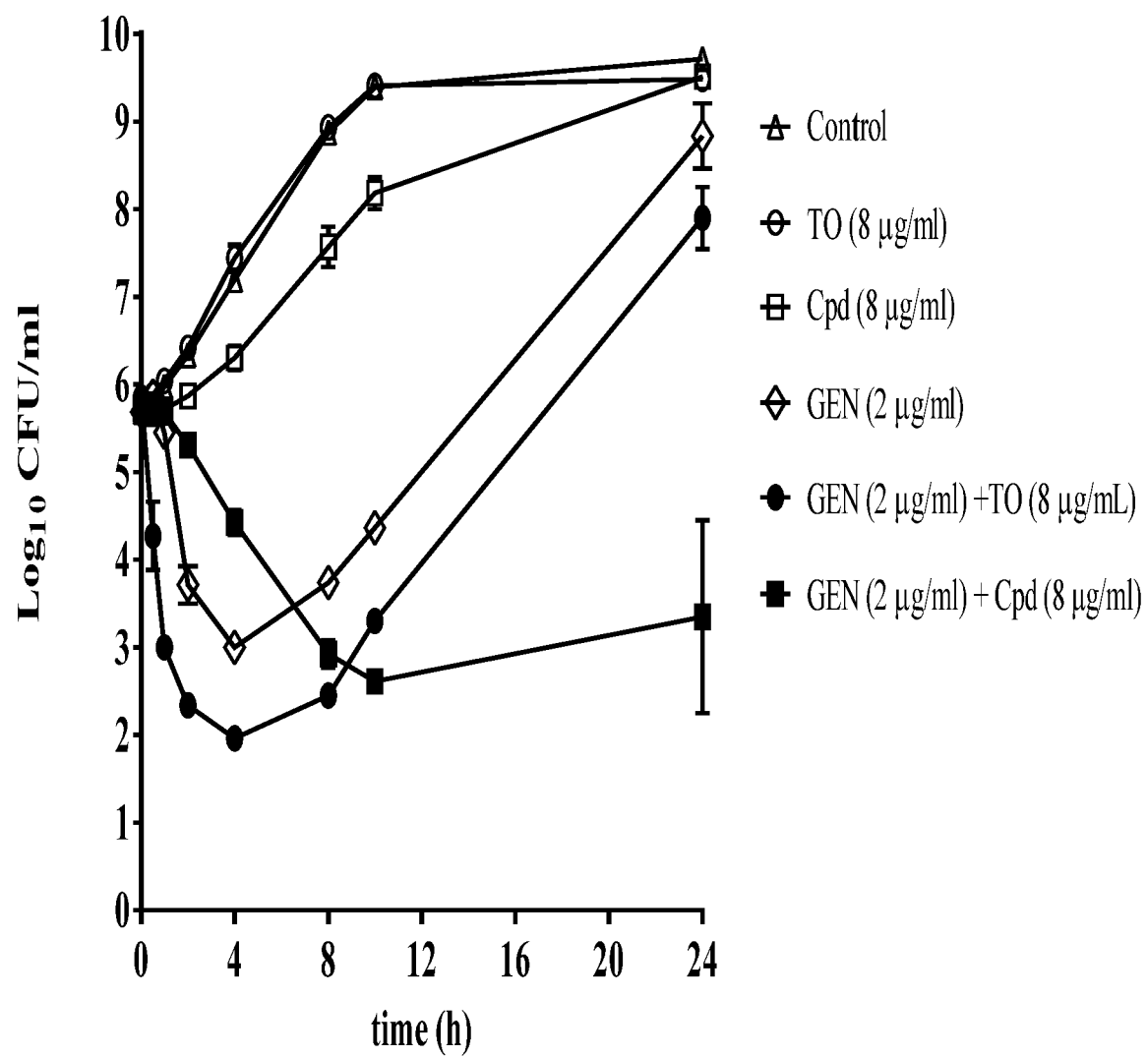
FIG. 2 presents time-kill experiments performed to determine whether the effect of tomatidine hydrochloride salt (TO) and compound #14 (Cpd) or the combination of each of these compounds with an aminoglycoside (gentamicin (GEN)) on Listeria monocytogenes (strain ATCC 13932) is bacteriostatic (prevents growth) or bactericidal (kills cells). The combination of gentamicin and Compound 14 results in an important bactericidal synergy.

Results:

FIG. 2 clearly demonstrates that tomatidine hydrochloride salt used alone does not affect the growth of *L. monocytogenes*, whereas at the same sub-inhibitory concentration, Compound 14 reduces the growth of this pathogen (FIG. 2). More interestingly, using a combination of gentamicin and Compound 14, results show an important bactericidal synergy that is not seen with either molecule used alone or when gentamicin is used in combination with tomatidine.

TABLE 3

Antibacterial effect of Compound 14 on normal antibiotic-resistant *Staphylococcus aureus* (MRSA) when used alone or in combination with gentamicin or with kanamycin and cefalexin.

| | MIC (µg/ml) | | | Potentiation fold | MIC (µg/ml) | | | | Potentiation fold |
|---|---|---|---|---|---|---|---|---|---|
| | | | c GEN + Cpd 14 at | d GEN + Cpd 14 at | | | g CEF + KAN | h CEF + KAN (3:2) + Cpd | i CEF + KAN (3:2) + Cpd |
| Strain | a Cpd 14 | b GEN | 4 µg/ml | 4 µg/ml | e CEF | f KAN | (3:2) | 14 at 4 µg/ml | 14 at 4 µg/ml |
| MRSA USA100 | 16 | 0.5 | 0.12 | 4 | 256 | 256 | 128:86 | 4:3 | 32 |
| MRSA USA300 | 16 | 0.5 | 0.06 | 8 | 256 | >1024 | 256:171 | 8:6 | 32 |
| MRSA COL | 16 | 0.25 | 0.06 | 4 | 256 | 4 | 4:3 | 0.5:0.35 | 8 | a: MIC of Compound 14 (Cpd 14) against the tested methicillin-resistant *S. aureus* strains (MRSA);
b: MIC of gentamicin (GEN) against the tested MRSA strains;
c: MIC of gentamicin (GEN) against the tested MRSA strains when Cpd 14 is present at 4 µg/ml;
d: The potentiation fold is defined as the ratio of the MIC of gentamicin (GEN) alone and the MIC of GEN in combination with Compound 14 (Cpd 14) used at 4 µg/mL;
e: MIC of cefalexin (CEF) against the tested MRSA strains;
f: MIC of kanamycin (KAN) against the tested MRSA strains;
g: MICs of cefalexin (CEF) and kanamycin (KAN) when used in combination at a ratio of 3:2;
h: MICs of cefalexin (CEF) and kanamycin (KAN) when used in combination at a ratio of 3:2, against the tested MRSA strains when Cpd 14 is present at 4 µg/ml;
i: The potentiation fold is defined as the ratio of the respective MICs of cefalexin (CEF) and kanamycin (KAN) when used in combination at a ratio of 3:2 and the MICs of CEF and KAN when used in combination at a ratio of 3:2 in the presence of Compound 14 (Cpd 14) used at 4 µg/mL.

Example 22

Bactericidal Activity of Tomatidine and Compound 14 Alone or in Combination with an Aminoglycoside Against *Listeria monocytogenes*

Time-kill experiments were performed in order to determine whether the effect of test compounds or the combination with an aminoglycoside on *Listeria monocytogenes* (strain ATCC 13932) is bacteriostatic (prevents growth) or bactericidal (kills cells).

Method:

Bacteria were inoculated at ~$10^5$-$10^6$ CFU/ml in BHI in the absence or presence of antibiotics at the specified concentrations: concentrations of 8 µg/ml of tomatidine hydrochloride salt (TO); 8 µg/ml of Compound 14 (Cpd); 2 µg/ml of gentamicin (GEN); combination of 8 µg/ml TO and 2 µg/ml gentamicin; or combination of 8 µg/ml Compound 14 and 2 µg/ml gentamicin (FIG. 2). At several time points during growth at 35° C. (225 RPM), bacteria were sampled, serially diluted and plated on Brain Hearth Infusion agar Example 23

Bactericidal Activity of Tomatidine and Compound 14 Against Small-Colony Variants (SCVs) of Bacterial Species of the Firmicutes Phylum Time-kill experiments were performed in order to determine whether the effect of test compounds on SCVs of bacterial species of the Firmicutes phylum is bacteriostatic (prevents growth) or bactericidal (kills cells).

Method:

*Listeria monocytogenes* ATCC 13932 SCVs were produced by plating a large inoculum (~$10^5$ bacterial cells) on brain heart infusion agar (BHIA) plates containing various amounts of gentamicin in order to create a selective pressure for the generation of electron transport-deficient bacteria with the SCV phenotype, which are known to be less susceptible to aminoglycoside antibiotics (e.g., gentamicin). Indeed, aminoglycosides require the proton-motive force in order to penetrate the bacterium (Bryan and Kwan, 1981). As expected, SCV isolates were collected from such selective plates and were then passaged on drug-free medium to assess stability of the SCV phenotype. SCV isolates keeping the SCV phenotype after several passages on drug-free medium were then used for experiments described below.

One of the *L. monocytogenes* SCV described above was used in time-kill experiments as described in Example 22. Bacteria were inoculated at ~$10^5$-$10^6$ CFU/mL in BHI in the absence or presence of antibiotics at the specified concentrations: concentrations of 8 µg/mL of tomatidine hydrochloride salt (TO) or 8 µg/mL of Compound 14 (Cpd). At some time-points during growth at 35° C. (225 RPM), bacteria were sampled, serially diluted and plated on BHIA for colony-forming unit (CFU) determinations (i.e., viable bacterial counts). Plates were incubated for 48 h at 35° C. The antibacterial activities of these molecules at the 8 h and 24 h time points are presented in FIGS. 3A-B. They represent the results of three independent experiments.

Figure 3A:
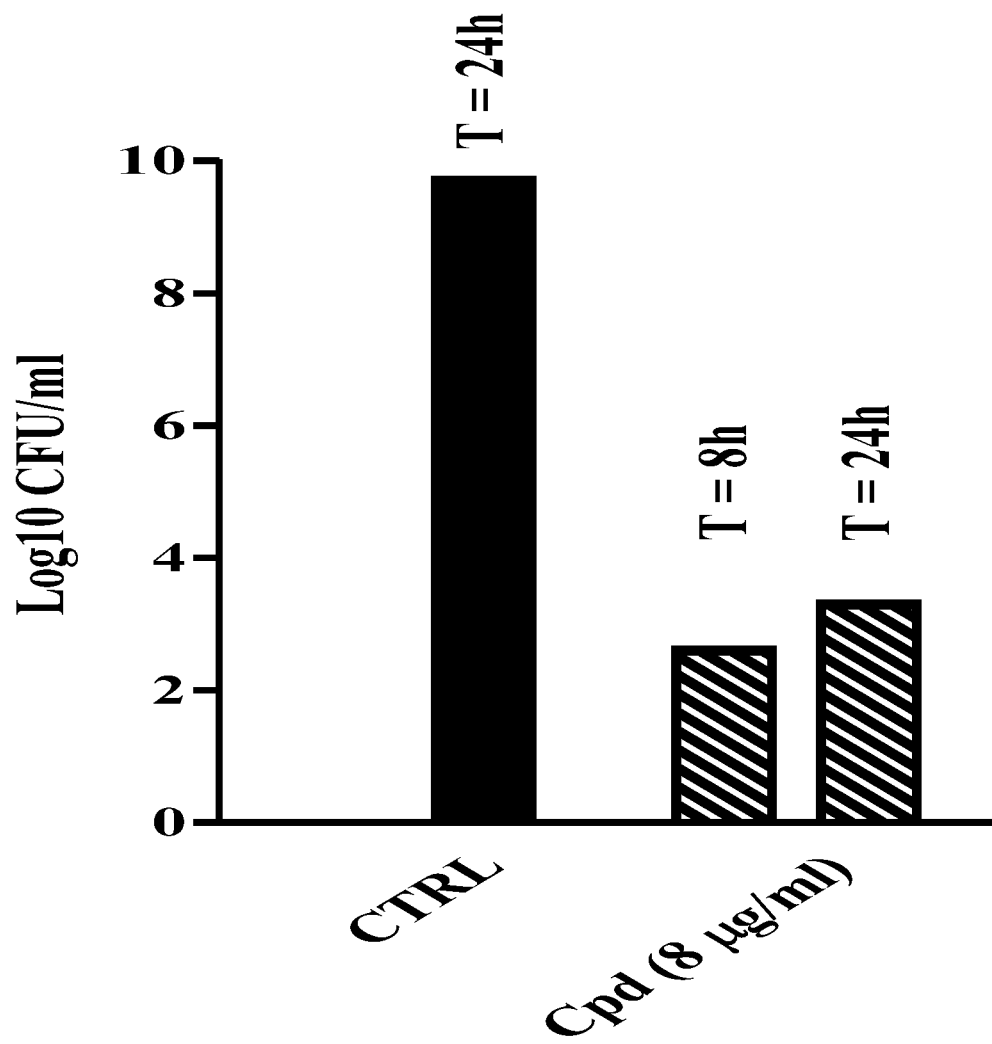
FIGS. 3A-B presents time-kill experiments showing (FIG. 3A) the bactericidal effect of compound 14 (Cpd; 8 μg/mL) on Listeria monocytogenes SCVs after 8 hours and 24 hours expressed as log 10 CFU.
Figure 3B:
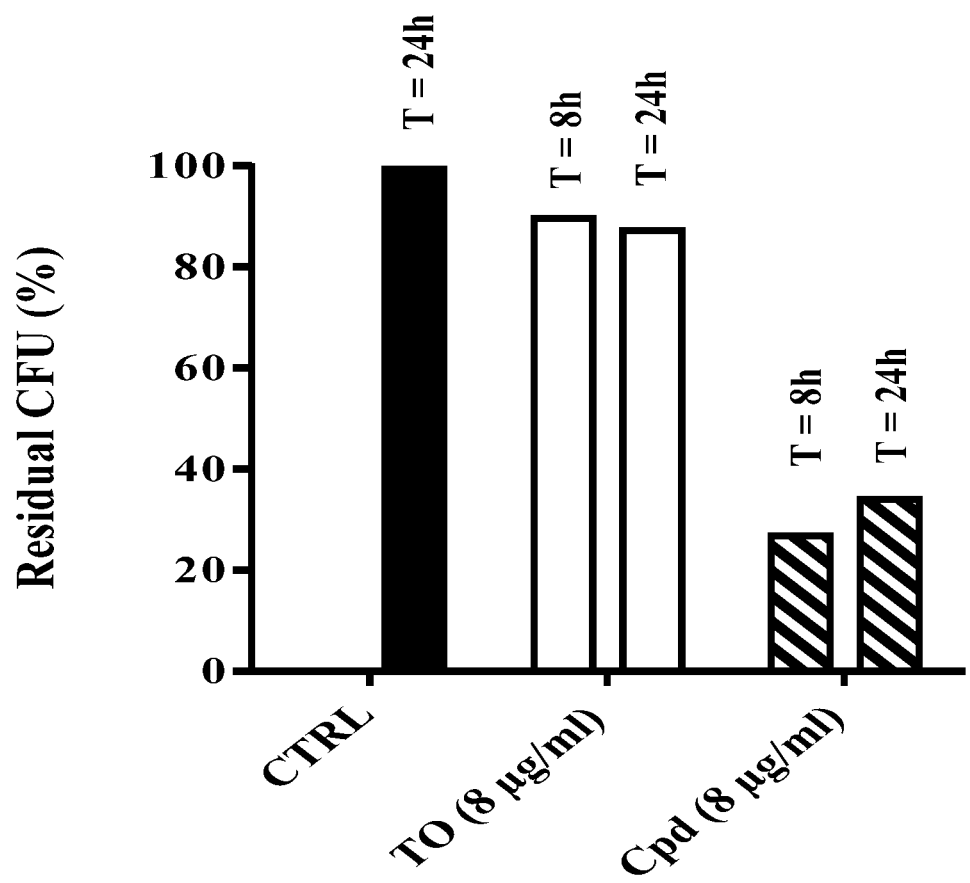

Results:

FIG. 3A clearly demonstrates that Compound 14 efficiently kills the SCV variants of *L. monocytogenes*, i.e., there is an important loss of bacterial CFUs compared to the no drug control (CTRL). FIG. 3B shows the superior bactericidal activity of Compound 14 compared to that obtained with tomatidine hydrochloride salt used at the same concentration. In FIG. 3B, data are expressed in percent of residual CFUs compared to the no drug control to facilitate the comparison between the activities of tomatidine hydrochloride salt and Compound 14 against the *L. monocytogenes* SCV.

Example 24

Bactericidal Activity of Tomatidine and Compound 14 Alone or in Combination with an Aminoglycoside Against *Staphylococcus aureus* Grown in a Biofilm The bactericidal activity of tomatidine and Compound 14 in combination with gentamicin against *Staphylococcus aureus* was evaluated against this bacterium grown in a biofilm. Biofilms confer to bacteria protection from host defenses as well as tolerance to some antibiotics that target active and dividing cells. In addition, biofilms also provide protection against hydrodynamic shear forces, and biofilm infections are generally difficult to eradicate even in hosts with intact immune system (Costerton et al, 1999; Davies 2003).

Method:

*Staphylococcus aureus* strain SH1000 of the normal phenotype (i.e., non-SCV) was used for its high ability to produce biofilms. The Calgary biofilm device (96-well plates with peg lids) was used to grow *S. aureus* in biofilms (Ceri et al, 1999) and to test the bactericidal activity of compounds (Moskowitz et al, 2004). Briefly, *S. aureus* SH1000 was grown in the Calgary biofilm device for 24 h at 35° C. until the biofilm forms on the pegs. The pegs were then washed, the medium was removed and the peg lids were dipped in fresh medium containing various amounts of test compounds. Bacteria in biofilms were allowed to grow in presence of compounds for 24 h at 35° C., after which pegs were washed and the remaining bacteria were released from biofilms by sonication before serial dilutions and plate counting (CFU determination). Replicate experiments were performed in order to quantify the residual amount of biofilm on pegs by crystal violet staining and spectrophotometry (absorbance [OD] at 562 nm).

Figure 4A:
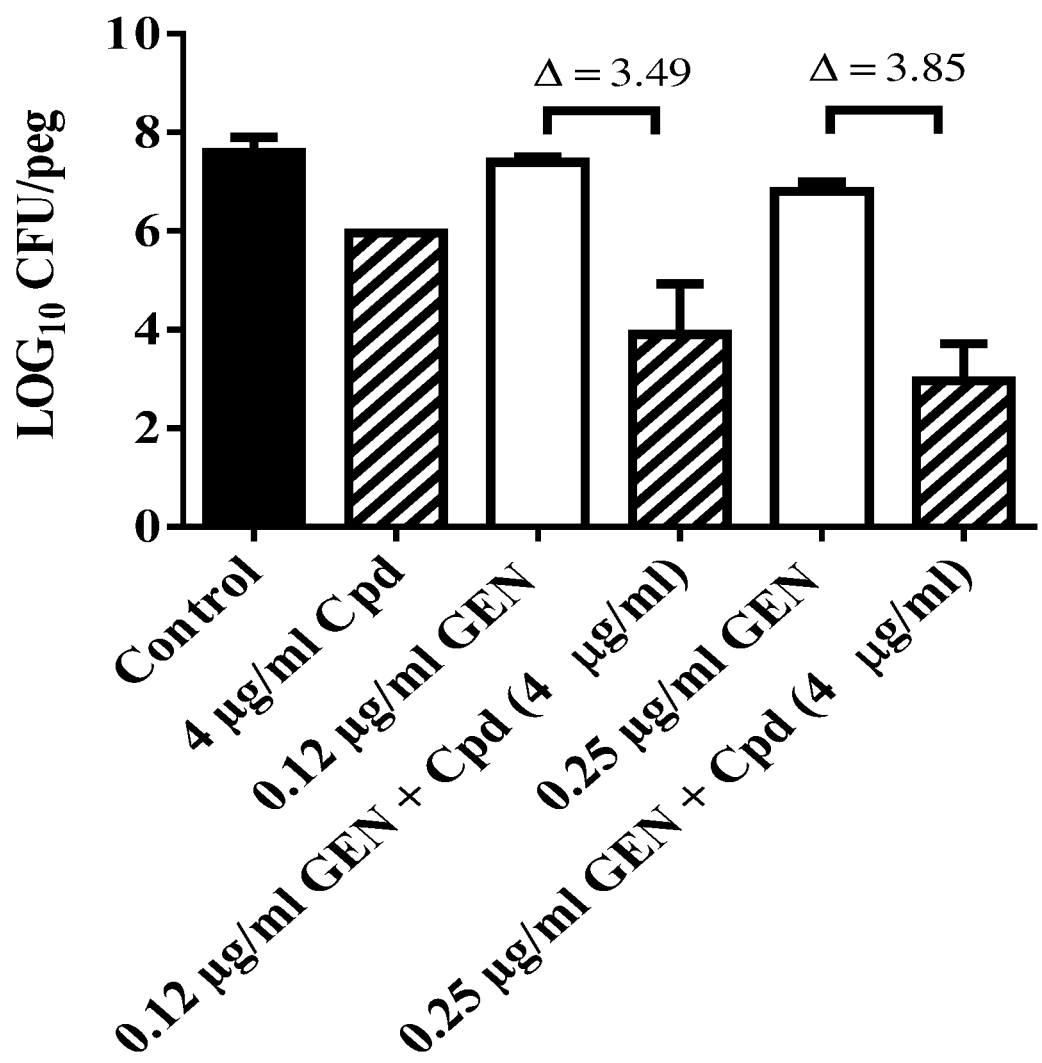
FIGS. 4A-B presents (FIG. 4A) the effect of compound 14 (Cpd) alone or in combination with gentamicin (GEN) against normal Staphylococcus aureus grown in biofilms.
Figure 4B:
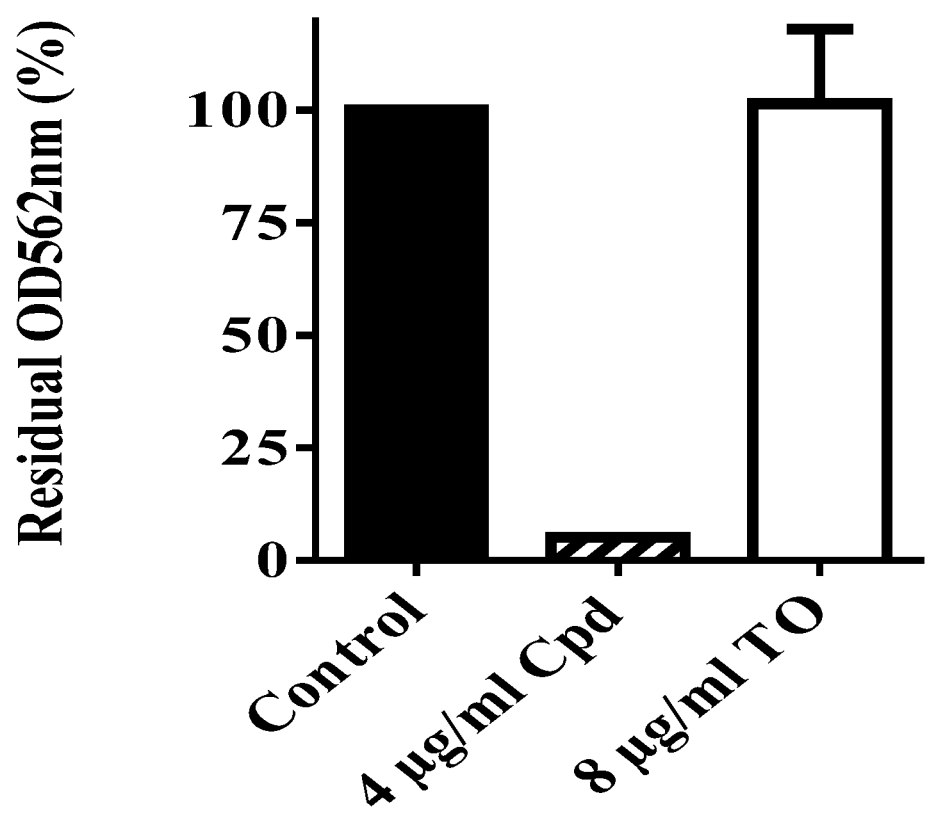

Results:

FIG. 4A demonstrates that Compound 14 (Cpd) efficiently kills *S. aureus* in biofilms especially when in combination with gentamicin (GEN), i.e., there was an important loss of bacterial CFUs compared to the no drug control or to either Compound 14 or gentamicin used alone at the indicated concentrations. FIG. 4B also shows the superior biofilm disrupting activity of Compound 14 used alone at 4 µg/ml compared to that observed with tomatidine hydrochloride salt (TO, used at 8 µg/ml). In FIG. 4B, data are expressed in percent of residual crystal violet absorbance (OD 562 nm) compared to the no drug control to facilitate the comparison between the biofilm disrupting activities of tomatidine hydrochloride salt and Compound 14 against *S. aureus* SH1000 biofilms.

Example 25

Testing the Biological Activity of the Compounds of the Invention

The biological activity of compounds of the present invention, used alone, can be evaluated using techniques as described in Examples 20-23 to determine the antibacterial activity against SCV strains (e.g., *Staphylococcus aureus, Bacillus cereus, Bacillus subtilis, Listeria monocytogenes*) and against normal bacterial strains (e.g., *S. aureus, B. cereus, B. subtilis, L monocytogenes*), as well as to determine the potentiating effect of compounds of the present invention on aminoglycoside antibiotics against normal strains (e.g., *S. aureus, B. cereus, B. subtilis, L. monocytogenes*), and using techniques as described in Example 24, to determine the antibacterial activity of compounds of the present invention, used alone or in combination with an aminoglycoside, against bacteria in biofilm (e.g., *S. aureus, B. cereus, B. subtilis, L monocytogenes*).

Also determined is the antibacterial activity against additional Firmicutes of the Bacillales group such as coagulase-positive and -negative staphylococci including *S. intermedius, S. hyicus, S. chromogenes, S. stimulans, S. lugdenensis S. capitis*, other bacilli such as *Bacillus anthracis, Bacillus coagulans*, and other *Listeria* such as *Listeria ivanovii*.

Example 26

Inhibitory Effect of Compounds of the Present Invention Measured in Cell Cultures The compounds of the present invention were tested for their ability to inhibit the growth of normal bacteria alone or in combination with aminoglycosides or of bacteria with electron transport deficiencies during infection of cell cultures.

Results herein show that Compound 14 has an antimicrobial activity against intracellular SCVs. This is particularly relevant because the ability of SCVs to persist within host cells is thought to be involved in the development of chronic and difficult-to-treat infections (Sendi and Proctor, 2009). This is also of particular relevance because *Listeria monocytogenes* is a notorious intracellular pathogen (Hamon et al, 2012). More precisely, the following results demonstrate that Compound 14 can significantly decrease the infection of polarized airway epithelial cells by SCVs by inhibiting their ability to replicate inside cells.

Method:

Human airway epithelial cells, the Calu-3 cell line ATCC HTB 55, were used in this cell culture assay. Cells were cultured in Eagle's Minimum Essential Medium (EMEM) supplemented with 0.1 mM MEM nonessential amino acids, 1 mM of sodium pyruvate, 100 U/ml penicillin, 0.1 mg/ml streptomycin, 2.5 µg/ml of Fungizone and 10% fetal bovine serum (FBS) at 37° C. in 5% $CO_2$. For routine culture, 4

µg/ml of puromycin was added to culture media. All cell culture reagents were purchased from Wisent (St-Bruno, QC, Canada). Cell infection assays were performed as previously described (Mitchell et al., 2011). Cells were seeded at $2.5 \times 10^5$ cells/inserts on 12-well Transwell™ plates and cultured for 9 to 10 days in an air:liquid system. The complete medium in the basal compartment was replaced by the invasion medium (1% FBS and no antibiotics) 18 h before assays. Inocula were prepared by suspending bacteria grown 20 h on BHIA plates in ice-cold PBS. Bacteria (the *S. aureus* SCV strain CF07-S; Mitchell et al., 2011) were then washed three times in ice-cold PBS and suspended in the invasion medium supplemented with 0.5% BSA at a density of approximately $4 \times 10^8$ CFU/ml. Cells were washed twice with PBS and 250 µl of bacterial suspension were apically added to each insert. Invasion was allowed for 3 h, inserts were emptied and washed three times with PBS. Invasion medium supplemented with 20 µg/ml of lysostaphin (Sigma) was then added to kill extracellular bacteria and the cells were further incubated 24 or 48 h in presence of lysostaphin. DMSO or the different concentrations of Compound 14 were added after invasion. Cells were washed once with PBS and the invasion medium supplemented with lysostaphin, DMSO and/or tomatidine was replaced at 24 h post-internalization. Fresh invasion medium supplemented with lysostaphin was also added 1 h before cell lysis to ensure that only intracellular bacteria were counted. Following three washes with PBS, cells were detached with 100 µl of trypsin 0.25% and lyzed for 10 min by the addition of 400 µl of water containing 0.05% of Triton X-100. Lysates were serially diluted 10-fold and plated on agar for bacterial CFU determination. Plates were incubated for 48 h at 35° C. Results are reported in FIG. 5.

Figure 5:
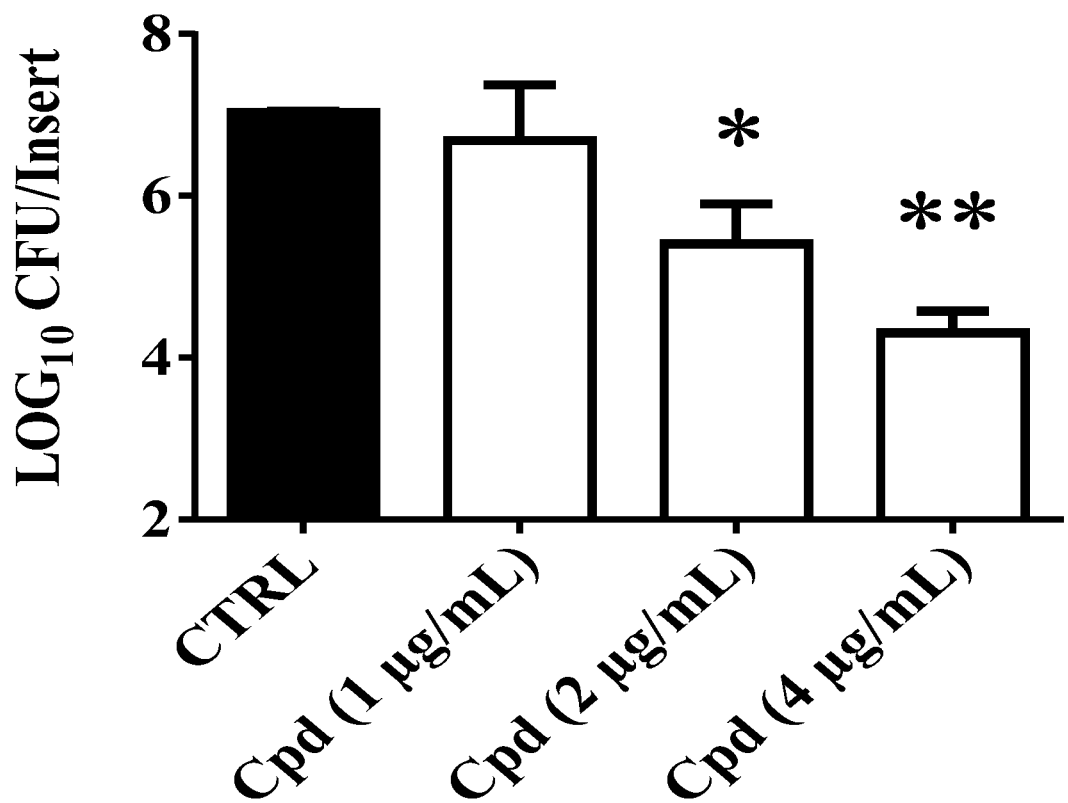
FIG. 5 shows the effect of Compound 14 (Cpd) on the intracellular replication of a clinical SCV strain of S. aureus (strain CF07-S) in polarized Calu-3 epithelial cells. The epithelial cells treated with 2 and 4 μg/ml of Compound 14 contained significantly less SCVs than DMSO-treated cells (control) 48 h post-internalization. Significant differences in comparison to the control are shown (*, P<0.01; **, P<0.001; one-way ANOVA with a Dunnett's post test). Data are presented as means with standard deviations.

Results:

FIG. 5 shows the effect of Compound 14 (Cpd) on the intracellular replication of a clinical SCV strain of *S. aureus* (strain CF07-S) in polarized Calu-3 epithelial cells. The epithelial cells treated with 2 and 4 µg/ml of Compound 14 contained significantly less SCVs than DMSO-treated cells (control) 48 h post-internalization. Significant differences in comparison to the control are shown (*, P<0.01; **, P<0.001; one-way ANOVA with a Dunnett's post test). Data are presented as means with standard deviations. This shows that Compound 14 can efficiently kill intracellular bacterial pathogens.

Example 27

Compound 14 Keeps Some of its Antibacterial Activity Against Tomatidine-Resistant *S. aureus* hemB Strains Having Mutations in the ATP Synthase Target Tomatidine was used as a selective pressure to raise tomatidine-resistant *S. aureus* hemB strains in order to identify the genomic mutations leading to resistance and to establish the nature of the molecular target of tomatidine.

Method:

The *S. aureus* SCV strain NewbouldΔhemB (hemB) that is susceptible to the antibacterial action of tomatidine hydrochloride salt and Compound 14 (Table 1) was passaged in BHI broth containing various amounts of tomatidine or tomatidine in combination with gentamicin. At each passage, using a microdilution method in 96-well microplates, *S. aureus* hemB was inoculated at $\sim 10^5$-$10^6$ CFU/ml and incubated at 35° C. for 48 h. The range of tomatidine concentrations tested was 0.03 to 64 µg/ml using doubling increments. The concentration of gentamicin was fixed at 4 µg/mL when it was used in combination with tomatidine. At each passage, the minimal inhibitory concentrations (MICs) (i.e. lowest concentration of an antimicrobial that inhibits the visible growth of bacteria), of tomatidine was determined. The bacteria used as inoculum for the next passage were from the well preceeding the well showing the MIC (i.e. the well containing half the MIC). At each passage, the population of bacteria serving as the inoculum for the next passage was spread on BHI agar plates and three isolated colonies were collected and frozen until used for whole-genome sequencing.

Illumina sequencing libraries were prepared using the multiplexing method of Rodrigue et al., 2010. Briefly, genomic DNA from bacteria were sheared by sonication using a Bioruptor Plus™, and the resulting DNA molecules were treated with T4 DNA polymerase and T4 polynucleotide kinase to be made blunt and phosphorylated. AMPure™ XP SPRI beads were used for size selection of the DNA fragments at an average size of ~500 bp. Short double-stranded adaptors were ligated and subjected to a nick translation reaction using Taq DNA polymerase. The adaptors were used as priming sites for PCR amplification to incorporate a 6 bp index for sample multiplexing. The size and concentration of the libraries were determined before being mixed and sent for sequencing on the Illumina HiSeg2000™ platform at the Genome Quebec and McGill University Innovation Centre (Montreal, QC, Canada). The obtained sequences were then aligned against reference *S. aureus* genomes with Burrows-Wheeler Alignment to identify possible SNPs, insertions/deletions, and genomic rearrangements (Li and Durbin 09).

Results:

Tomatidine-resistant mutants were found in the bacterial colonies isolated after sequential passages on tomatidine and on tomatidine and gentamicin. Genomic mutations that were conserved in each of the three isolated colonies of each of the passages showing the same level of resistance to tomatidine (MIC>32 µg/mL) were associated to the molecular target.

The target of tomatidine was thus identified as the ATP synthase subunit c (gene NWMN_2012, from the *S. aureus* Newman annotation).

The bacterial ATP synthase (also known as F-ATPase, F-Type ATPase or $F_OF_1$-ATPase) is divided into two regions: a cytoplasmic globular $F_1$ catalytic sector and a membrane-bound $F_O$ proton-translocating sector (Hong and Pedersen, 2008). $F_1$ (composed of five subunits: $\alpha_3\beta_3\gamma\delta\epsilon$) generates ATP from proton translocation through $F_O$. $F_O$ is composed of three types of subunits, namely subunit a, subunit b and subunit c. $F_O$ contains 1 subunit a, 2 subunits b and 8 to 15 subunits C, which is denoted by $ab_2c_{8-15}$. Compounds of the present invention target the c subunits (c-ring) of $F_O$.

The "O" in $F_O$ comes from oligomycin. Oligomycin binds at the interface of subunit a and the c-ring oligomer and is a poison that specifically blocks proton transport through $F_O$ in the mitochondrial ATP synthase. Oligomycin is mostly ineffective on ATP synthases from most bacteria. Inversely, Bedaquiline (TMC207) is specific for the Mycobacterial ATP synthase (i.e., has no inhibitory activity against *S. aureus* or *E. coli*) and is a poor inhibitor of the mitochondrial enzyme.

Figure 6B:
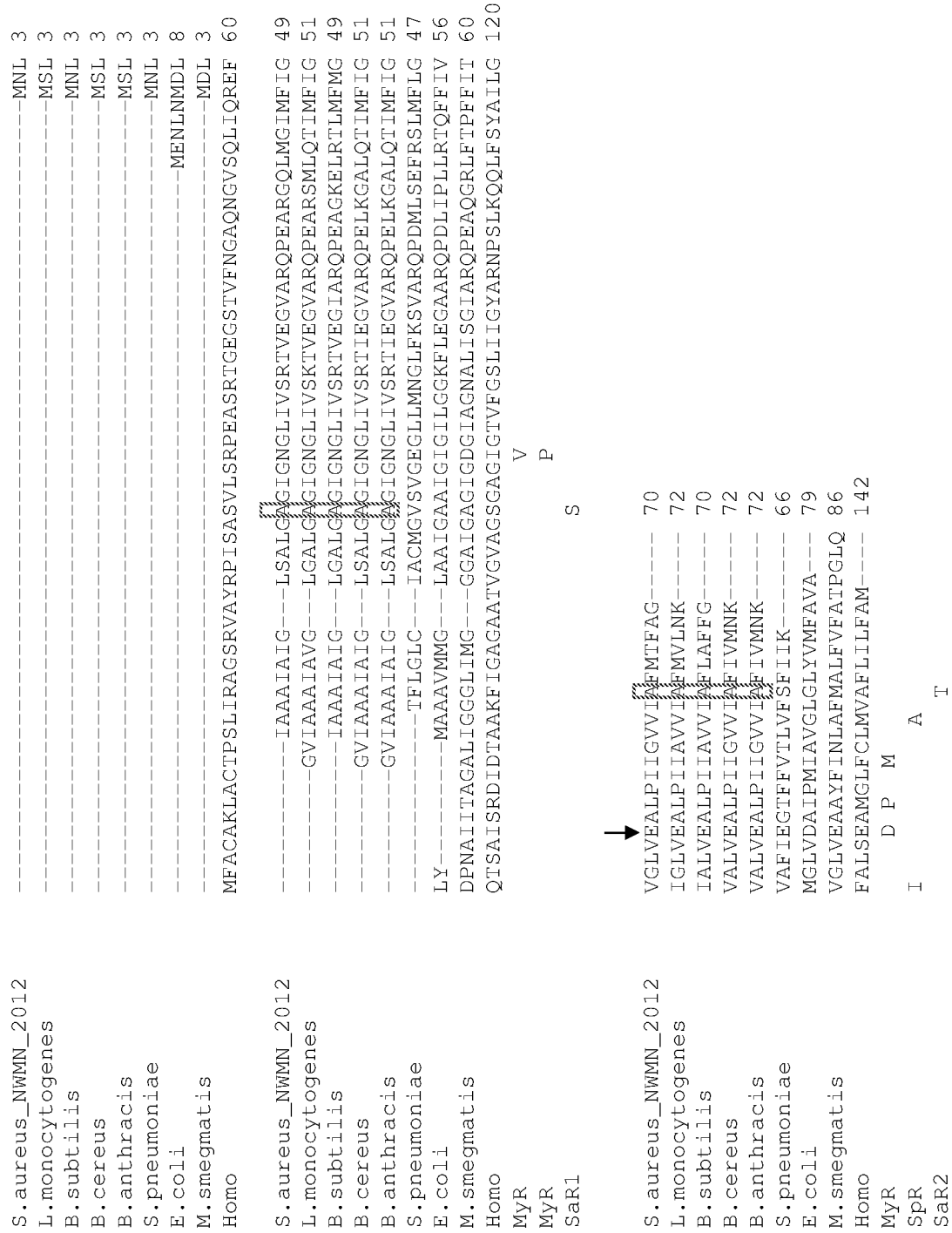

Two different mutations were found in the ATP synthase gene after sequential passages of the *S. aureus* strain hemB on tomatidine (e.g., mutant SaR1) and on tomatidine and gentamicin (e.g., mutant SaR2) (FIG. 6A). Interestingly, the resulting position and the type of amino acid changes that occurred from the mutations were different from those reported for *Mycobacterium* (MyR) or *Streptococcus pneumoniae* (SpR) mutants resistant to diarylquinoline ATP synthase inhibitors (bedaquiline or TMC207 or R207910 and derivatives; Andries et al, 2005; Petrella et al, 2006; Balemans et al, 2012; Segala et al, 2012) (FIG. 6B), showing that tomatidine interacts with the ATP synthase target differently than bedaquiline or its derivatives do. Notably, the nature of the amino acids that is present at the positions of the mutations for *S. aureus* SaR1 and SaR2 is conserved at both positions among the listed Firmicutes (boxed positions in FIGS. 6B-C).

Tomatidine and Compound 14 MICs were determined for *S. aureus* hemB and the resulting mutants obtained after sequential passages on tomatidine (e.g., mutant SaR1) and on tomatidine and gentamicin (e.g., mutant SaR2), and are reported in Table 4. Interestingly, Compound 14 retains some antibacterial activity against the tomatidine-resistant mutants, showing that Compound 14 is still able to reach the molecular target, ATP synthase, with some affinity despite the reported mutations (FIGS. 6A-B). For mutants SaR1 and SaR2, the fold increase in tomatidine MIC compared to the initial MIC level in hemB was >512, whereas the fold increase in Compound 14 MIC was only 16 and 8, respectively for SaR1 and SaR2, showing the improved potency of Compound 14 compared to tomatidine (Table 4).

Compound 14 are collected and subcultured to confirm resistance. Once the MIC of Compound 14 for these stable resistant isolates is confirmed, isolates are frozen until used for sequencing of the ATP synthase gene. The genomic analysis of the ATP synthase subunit c gene (*S. aureus*_N-WMN_2012) is determined using a PCR and DNA sequencing approach.

Example 29

Inhibition of ATP Synthase Activity by Compound 14

The effect of test compounds on the generation of ATP by the ATP synthase of inverted membrane vesicles of *Staphylococcus aureus* is measured as previously described (Balemans et al, 2012). Membrane vesicles are prepared by disrupting *S. aureus* cells using a French press. Vesicles are then incubated with test compounds for 10 min before adding NADH and measuring the amounts of ATP generated by the ATP synthase using an ATP bioluminescence assay kit.

TABLE 4

Antibacterial activity of gentamicin, tomatidine and Compound 14 against *S. aureus* hemB (SCV) and tomatidine-resistant SCV mutants (SaR1 and SaR2)

| | MIC (µg/mL) | | | Fold increase in Tomatidine resistance[d] | Fold increase in Compound 14 resistance[e] |
|---|---|---|---|---|---|
| SCV Strain | Gentamicin | Tomatidine | Compound 14 | | |
| *S. aureus* hemB[a] | 4-8 | 0.0625 | 0.5 | — | — |
| *S. aureus* hemB (SaR1)[b] | 4-8 | >32 | 8 | >512 | 16 |
| *S. aureus* hemB (SaR2)[c] | 16 | >32 | 4 | >512 | 8 |

[a] *S. aureus* SCV strain NewbouldΔhemB;
[b] *S. aureus* SCV strain NewbouldΔhemB tomatidine-resistant mutant (SaR1) selected by sequential passages on increasing amounts of tomatidine;
[c] *S. aureus* SCV strain NewbouldΔhemB tomatidine-resistant mutant (SaR2) selected by sequential passages on increasing amounts of tomatidine in combination with 4 µg/ml gentamicin;
[d] Fold increase in tomatidine resistance as measured by the ratio of the MIC of tomatidine for the indicated mutant and the MIC of tomatidine for the susceptible strain NewbouldΔhemB; and
[e] Fold increase in Compound 14 resistance as measured by the ratio of the MIC of Compound 14 for the indicated mutant and the MIC of Compound 14 for the susceptible strain NewbouldΔhemB.

Example 28

Generation of *Staphylococcus aureus* Mutants Resistant to the Action of Compound 14

As in Example 27 with tomatidine, Compound 14 is used as a selective pressure to raise Compound 14-resistant *S. aureus* strains in order to identify the genomic mutations leading to resistance and to confirm the nature of the molecular target of Compound 14. In this Example, the normal strain *S. aureus* Newman is used as the target organism.

Method:

A large inoculum ($10^8$-$10^{10}$ bacteria) of the *S. aureus* strain Newman that is susceptible to the antibacterial action of Compound 14 is spread on BHI plates containing various amounts of Compound 14 (2 to 64 µg/mL) and plates are incubated at 35° C. for 48 h. At least three individual colonies growing at the highest permissive concentration of Example 30

Inhibitory Effect of Compounds of the Present Invention, Alone or in Combination with at Least One Aminoglycoside, Measured During Infection in Animals (In Vivo)

The compounds of the present invention are able to inhibit the growth of normal bacteria alone or in combination with aminoglycosides or of bacteria with electron transport deficiencies during infection of an animal (in vivo). The antibacterial activity in vivo is demonstrated through the use of various infection models using, for example mice models of septicemia, soft tissue infections, respiratory infections, burned tissues, and mastitis.

The compounds of the present invention are able to inhibit the growth of mixed bacterial species, such as *Staphylococcus aureus* and *Pseudomonas aeruginosa*, in combination with aminoglycosides during a co-infection of an animal (in vivo).

Septicemia Model

The septicemia model (Deslouches et al, 2005) allows testing the efficacy of compounds to clear or diminish an infection. Bacteria are injected iv or ip with an inoculum that leads to 50-70% mortality in untreated mice (3-5 mice per test group). Following inoculation, compounds are administered either iv, ip, sc or im and treatment efficacy is measured by the reduction of bacterial CFU in various organs (e.g., liver, kidneys), in the peritoneal liquid or in blood or is evaluated based on the animals' survival rate.

Neutropenic Mouse Thigh Model

Compound efficacy in a neutropenic mouse thigh model is evaluated as follows (Malouin et al, 2005): Mice (immune suppressed with cyclophosphamide treatments prior to infection) are challenged with bacteria ($10^4$ CFU per thigh im). To determine efficacy, compounds are delivered iv, sc, ip or im 2 h post-infection. Mice (3-5 mice per treatment) are euthanized 8 h post-infection. The thigh tissues (two samples per animal) are recovered, homogenized, and bacterial CFU per g of tissue are determined by plating appropriate dilutions.

Lung Infection (Pneumonia) Model

Compound efficacy in a lung infection (pneumonia) model was evaluated as follow (Ragle et al, 2010; Mitchell et al, 2013): Mice (36) were challenged with an intratracheal injection of S. aureus SCV strain hemB ($10^7$ CFU) ($10^7$ CFU) (normal S. aureus could also have been used, mixed or not with P. aeruginosa for a co-infection). To determine efficacy, Compounds (Compound 14 or tomatidine hydrochloride salt [TO]) (could also be used in combination with an aminoglycoside) were delivered intratracheally (administration could also have been made iv, sc, ip, im or by aerosol), 4 h post-infection. More particularly, 11 mice were untreated (Unrteated); 4 mice were treated with 10 µg of tomatidine (TO (10)); 4 mice were treated with 100 µg of tomatidine (TO (100)); 3 mice were treated with 10 µg of compound 14 (Compound 14 (10)); 8 mice were treated with 100 µg of compound 14 (Compound 14 (100)); and 6 mice were treated with 200 µg of compound 14 (Compound 14 (200)). Mice were euthanized 24 h post-infection. The lungs were recovered, homogenized, and bacterial CFU per g of tissue were determined by plating appropriate dilutions on Brain Hearth Infusion agar media (other media such as for example, mannitol salt agar for S. aureus or cetrimide plates for P. aeruginosa could be used).

Results are presented in FIG. 7. Each dot represents the CFU per g of tissue for one mouse. The boxes represent the CFU data distribution, the first quartile, the median and the third quartile. Statistical differences (P<0.001) between CFU recovered from treated and untreated animals are shown by asterisks (non-parametric Kruskal-Wallis ANOVA with Dunn's post test).

This shows that Compound 14 can significantly reduce the bacterial load in mouse lungs infected with S. aureus SCV strain hemB. In this respect, Compound 14 was superior to tomatidine hydrochloride salt (TO) used at an equivalent concentration (100 µg).

Burned Tissue Model

A burned tissue model is performed as follow. Female CF-1 mice (22 to 25 g) receive a nonlethal, partial-thickness alcohol flame burn (10 s) covering 15% of the body surface (Goldberg et al., 1995) or by causing the thermal injury to the skin by placing the shaved exposed back area to 90° C. water for 10 s (McVay et al., 2007). Immediately after the thermal injury, the animals receive 0.5 ml of sterile normal saline subcutaneously as fluid replacement therapy. Subsequently, bacteria ($10^2$ CFU) such as S. aureus alone (or mixed with P. aeruginosa for a co-infection) are injected subcutaneously into the burned site. To determine efficacy, compounds (alone or in combination with an aminoglycoside) are delivered iv, sc, ip, im or diluted in an ointment spread on the burned area, 2 h post-infection. Mice (3-5 mice per treatment) are euthanized 24-48 h post-infection. The burned skin tissue is recovered, homogenized, and bacterial CFU per g of tissue are determined by plating appropriate dilutions on appropriate selective plates (for examples, manitol salt agar for S. aureus and cetrimide plates for P. aeruginosa).

Mouse Mastitis Model

Compound efficacy in a mouse mastitis model is evaluated as follow (Brouillette et al, 2004b): Lactating CD-1 mice are challenged with bacteria injected through the teat canal. A Hamilton syringe with a blunt needle is used to inoculate with $10^2$ CFU per gland in both L4 and R4 mammary glands. Compounds are delivered by an intramammary injection 4 h following challenge. Each experimental group is composed of 3-6 mice (i.e., 6-12 glands). Mammary glands are harvested, weighed and homogenized in PBS at 18 h. Homogenates are serially diluted and plated on agar for bacterial CFU determination.

Although the present invention has been described hereinabove by way of specific embodiments thereof, it can be modified, without departing from the spirit and nature of the subject invention as defined in the appended claims.

REFERENCES

Alexander, E. H., and Hudson, M. C. (2001) Factors influencing the internalization of Staphylococcus aureus and impacts on the course of infections in humans. Appl Microbiol Biotechnol 56: 361-366.

Allegrucci, M., and Sauer, K. (2008) Formation of Streptococcus pneumoniae non-phase-variable colony variants is due to increased mutation frequency present under biofilm growth conditions. J Bacteriol 190: 6330-6339.

Andries K et al. 2005. A Diarylquinoline Drug Active on the ATP Synthase of Mycobacterium tuberculosis. Science, 307: 223-227.

Archer, G. L. (1998) Staphylococcus aureus: a well-armed pathogen. Clin Infect Dis 26: 1179-1181.

Atalla, H., Gyles, C., Jacob, C. L., Moisan, H., Malouin, F., and Mallard, B. (2008) Characterization of a Staphylococcus aureus small colony variant (SCV) associated with persistent bovine mastitis. Foodborne Pathog Dis 5: 785-799.

Avni, T., A. Levcovich, D. D. Ad-El, L. Leibovici, M. Paul. 2010. Prophylactic antibiotics for burns patients: systematic review and meta-analysis. BMJ 2010; 340:c241 doi: 10.1136/bmj.c241.

Bad Bug Book. Bacillus cereus and other Bacillus spp. Foodborne Pathogenic Microorganisms and Natural Toxins Handbook. Food and Drug Administration (www.fda.gov).

Balemans, W, et al. 2012. Novel Antibiotics Targeting Respiratory ATP Synthesis in Gram-Positive Pathogenic Bacteria. Antimicrob. Agents Chemother. 56: 4131-4139.

Beierlein J M, Anderson A C. 2011. New developments in vaccines, inhibitors of anthrax toxins, and antibiotic therapeutics for Bacillus anthracis. Curr Med Chem. 18(33): 5083-94.

Black, J. G. (2008) Microbiology: Principles and Explorations $7^{th}$ ed. John Wiley & Sons.

Brouillette, E., Martinez, A., Boyll, B. J., Allen, N. E., and Malouin, F. (2004) Persistence of a Staphylococcus aureus small-colony variant under antibiotic pressure in vivo. *FEMS Immunol Med Microbiol* 41: 35-41.

Bryan, L. E., and Kwan, S. (1981) Mechanisms of aminoglycoside resistance of anaerobic bacteria and facultative bacteria grown anaerobically. *J Antimicrob Chemother* 8 Suppl D: 1-8.

Canadian Cystic Fibrosis Foundation (2007) Patient data registry report. Toronto, ON, Canada.

Casey, A. L., Lambert, P. A., and Elliott, T. S. (2007) Staphylococci. *Int J Antimicrob Agents* 29 Suppl 3: S23-32.

Ceri, H., M. E. Olson, et al. 1999. The Calgary Biofilm Device: new technology for rapid determination of antibiotic susceptibilities of bacterial biofilms. J Clin Microbiol 37(6): 1771-6.

Chastre, J., and Fagon, J. Y. (2002) Ventilator-associated pneumonia. *Am J Respir Crit Care Med* 165: 867-903.

Chatterjee, I., Herrmann, M., Proctor, R. A., Peters, G., and Kahl, B. C. (2007) Enhanced post-stationary-phase survival of a clinical thymidine-dependent small-colony variant of Staphylococcus aureus results from lack of a functional tricarboxylic acid cycle. *J Bacteriol* 189: 2936-2940.

Clinical and Laboratory Standards Institute. Performance Standards for Antimicrobial Susceptibility Testing: Twenty-First Informational Supplement M100-S21. CLSI, Wayne, Pa., USA, 2011.

Costerton J W, Stewart P S, Greenberg E P. 1999. Bacterial biofilms: a common cause of persistent infections. Science 284: 1318-1322.

Cystic Fibrosis Foundation (2008) Patient registry annual report. Washington, D.C.

Dasenbrook, E. C., Checkley, W., Merlo, C. A., Konstan, M. W., Lechtzin, N., and Boyle, M. P. (2010) Association between respiratory tract methicillin-resistant *Staphylococcus aureus* and survival in cystic fibrosis. *Jama* 303: 2386-2392.

Davies D. 2003. Understanding biofilm resistance to antibacterial agents. Nat Rev Drug Discov 2: 114-122.

Davis, B D. 1982. Bactericidal synergism between beta-lactams and aminoglycosides: mechanism and possible therapeutic implications. Rev Infect Dis. 4(2):237-245.

Galli, J., Ardito, F., Calo, L., Mancinelli, L., Imperiali, M., Parrilla, C., Picciotti, P. M., and Fadda, G. (2007) Recurrent upper airway infections and bacterial biofilms. *J Laryngol Otol* 121: 341-344.

Ginnes, R. B., and V. Stewart. 1996. Respiration. In *Escherichia coli* and *Salmonella*, cellular and molecular biology, p. 217-261. Ed. F. C. Neidhardt. American Society for Microbiology, Washington.

Goerke, C., and Wolz, C. (2004) Regulatory and genomic plasticity of *Staphylococcus aureus* during persistent colonization and infection. *Int J Med Microbiol* 294: 195-202.

Goldberg, J. B., M. J. Coyne, Jr., A. N. Neely, I. A. Holder. 1995. Avirulence of a Pseudomonas aeruginosa algC Mutant in a Burned-Mouse Model of Infection. Infect. Immun. 63: 4166-4169.

Guillet, C., O. Join-Lambert, A. Le Monnier, A. Leclercq, F. Mechaï, M.-F. Mamzer-Bruneel, M. K. Bielecka, M. Scortti, O. Disson, P. Berche, J. Vazquez-Boland, O. Lortholary and M. Lecuit. 2010. Human Listeriosis Caused by Listeria ivanovii. Emerging Infectious Diseases, 16:136-138.

Hamon M A, Ribet D, Stavru F, Cossart P. 2012. Listeriolysin O: the Swiss army knife of *Listeria*. Trends Microbiol. 2012 August; 20(8):360-368.

Harlid, R., Andersson, G., Frostell, C. G., Jorbeck, H. J., and Ortqvist, A. B. (1996) Respiratory tract colonization and infection in patients with chronic tracheostomy. A one-year study in patients living at home. *Am J Respir Crit Care Med* 154: 124-129.

Harrison, F. (2007) Microbial ecology of the cystic fibrosis lung. *Microbiology* 153: 917-923.

Hoffman, L. R., Deziel, E., D'Argenio, D. A., Lepine, F., Emerson, J., McNamara, S., Gibson, R. L., Ramsey, B. W., and Miller, S. I. (2006) Selection for *Staphylococcus aureus* small-colony variants due to growth in the presence of *Pseudomonas aeruginosa*. *Proc Natl Acad Sci USA* 103: 19890-19895.

Hong, and Pedersen. 2008. ATP Synthase and the Actions of Inhibitors Utilized To Study Its Roles in Human Health, Disease, and Other Scientific Areas. Microbiol. Mol. Biol. Rev. 72:590-641.

Hubert D, H Réglier-Poupet, I Sermet-Gaudelus, A. Ferroni, M. Le Bourgeois, P-R Burgel, R Serreau, D Dusser, C Poyart, J Coste. 2012. Association between *Staphylococcus aureus* alone or combined with *Pseudomonas aeruginosa* and the clinical condition of patients with cystic fibrosis. J. Cystic Fibrosis. Publish ahead of print 2012.

Jacques, M., Aragon, V., and Tremblay, Y. D. (2010) Biofilm formation in bacterial pathogens of veterinary importance. *Anim Health Res Rev* 11: 97-121.

Jensen K. B., Braxmeier T. M., Demarcus M., Frey J. G., Kilburn J. D., (2002) Synthesis of Guanidinium-Derived Receptor Libraries and Screening for Selective Peptide Receptors in Water, *Chemistry—A European Journal*, 8:1300-1309.

Kloos, W. E., and Bannerman, T. L. (1994) Update on clinical significance of coagulase-negative staphylococci. *Clin Microbiol Rev* 7: 117-140.

Li and Durbin R. 2009. Fast and accurate short read alignment with Burrows-Wheeler Transform. Bioinformatics, 25:1754-60. [PMID: 19451168]

Lightbown, J. W., and Jackson, F. L. (1956) Inhibition of cytochrome systems of heart muscle and certain bacteria by the antagonists of dihydrostreptomycin: 2-alkyl-4-hydroxyquinoline N-oxides. *Biochem J* 63: 130-137.

Lyczak, J. B., Cannon, C. L., and Pier, G. B. (2002) Lung infections associated with cystic fibrosis. *Clin Microbiol Rev* 15: 194-222.

Machan, Z. A., Taylor, G. W., Pitt, T. L., Cole, P. J., and Wilson, R. (1992) 2-Heptyl-4-hydroxyquinoline N-oxide, an antistaphylococcal agent produced by *Pseudomonas aeruginosa*. *J Antimicrob Chemother* 30: 615-623.

Mates, S. M., L. Patel, H. R. Kaback, and M. H. Miller. 1983. Membrane potential in anaerobically growing *Staphylococcus aureus* and its relationship to gentamicin uptake. Antimicrob. Agents Chemother. 23:526-530.

McVay, C. S., M. Vela'squez, and J. A. Fralick. 2007. Phage Therapy of Pseudomonas aeruginosa Infection in a Mouse Burn Wound Model. Antimicrob. Agents Chemother. 51:1934-1938.

Mead, P. S., Slutsker, L., Dietz, V., McCaig, L. F., Bresee, J. S., Shapiro, C., Griffin, P. M., and Tauxe, R. V. (1999) Food-related illness and death in the United States. *Emerg Infect Dis* 5: 607-625.

Melter, O., and Radojevic, B. (2010) Small colony variants of *Staphylococcus aureus*—review. *Folia Microbiol (Praha)* 55: 548-558.

Mitchell, G., Brouillette, E., Seguin, D. L., Asselin, A. E., Jacob, C. L., and Malouin, F. (2010a) A role for sigma factor B in the emergence of *Staphylococcus aureus* small-colony variants and elevated biofilm production resulting from an exposure to aminoglycosides. *Microb Pathog* 48: 18-27.

Mitchell, G., Seguin, D. L., Asselin, A. E., Deziel, E., Cantin, A. M., Frost, E. H., Michaud, S., and Malouin, F. (2010b) *Staphylococcus aureus* sigma B-dependent emergence of small-colony variants and biofilm production following exposure to *Pseudomonas aeruginosa* 4-hydroxy-2-heptylquinoline-N-oxide. *BMC Microbiol* 10: 33.

Mitchell, G., M. Gattuso, G. Grondin, É. Marsault, K. Bouarab, F. Malouin. 2011. Tomatidine Inhibits the Replication of *Staphylococcus aureus* Small-Colony Variants in Cystic Fibrosis Airway Epithelial Cells. Antimicrob. Agents Chemother. 55:1937-1945.

Mitchell, G., M. Lafrance, S. Boulanger, D. L. Seguin, I. Guay, M. Gattuso, É. Marsault, K. Bouarab, and F. Malouin. 2012. Tomatidine acts in synergy with aminoglycoside antibiotics against multiresistant *Staphylococcus aureus* and prevents virulence gene expression. J. Antimicrob. Chemother. 67: 559-568.

Mitchell, G., K. Pépin Gaudreau, A. Fugère, É. Brouillette, E. H. Frost, A. M. Cantin, F. Malouin. 2013. SigB is a dominant regulator of virulence in *Staphylococcus aureus* small-colony variants. PLoS ONE 8(5): e65018. doi: 10.1371/journal.pone.0065018

Moisan, H., Brouillette, E., Jacob, C. L., Langlois-Begin, P., Michaud, S., and Malouin, F. (2006) Transcription of virulence factors in *Staphylococcus aureus* small-colony variants isolated from cystic fibrosis patients is influenced by SigB. *J Bacteriol* 188: 64-76.

Moskowitz, S. M., J. M. Foster, et al. 2004. Clinically feasible biofilm susceptibility assay for isolates of *Pseudomonas aeruginosa* from patients with cystic fibrosis. J Clin Microbiol 42(5): 1915-22.

Nagy, E. (2010) Anaerobic infections: update on treatment considerations. *Drugs* 70: 841-858.

Osbourn, A. E. (1996) Preformed Antimicrobial Compounds and Plant Defense against Fungal Attack. *Plant Cell* 8: 1821-1831.

Parkins, M. D., and Elborn, J. S. (2010) Newer antibacterial agents and their potential role in cystic fibrosis pulmonary exacerbation management. *J Antimicrob Chemother* 65: 1853-1861.

Petrella, S., E. Cambau, A. Chauffour, K. Andries, V. Jarlier, and W. Sougakoff. 2006. Genetic Basis for Natural and Acquired Resistance to the Diarylquinoline R207910 in Mycobacteria. Antimicrob. Agents Chemother. 50: 2853-2856.

Proctor, R. A., von Eiff, C., Kahl, B. C., Becker, K., McNamara, P., Herrmann, M., and Peters, G. (2006) Small colony variants: a pathogenic form of bacteria that facilitates persistent and recurrent infections. *Nat Rev Microbiol* 4: 295-305.

Pyorala, S., and Taponen, S. (2009) Coagulase-negative staphylococci-emerging mastitis pathogens. *Vet Microbiol* 134: 3-8.

Rodrigue S, Materna A C, Timberlake S C, Blackburn M C, Malmstrom R R, et al. (2010) Unlocking Short Read Sequencing for Metagenomics. PLoS ONE 5(7): e11840. doi:10.1371/journal.pone.0011840.

Rupnik, M., Wilcox, M. H., and Gerding, D. N. (2009) *Clostridium difficile* infection: new developments in epidemiology and pathogenesis. *Nat Rev Microbiol* 7: 526-536.

Sears, P. M., and McCarthy, K. K. (2003) Management and treatment of staphylococcal mastitis. *Vet Clin North Am Food Anim Pract* 19: 171-185, vii.

Segala, E., W. Sougakoff, A. Nevejans-Chauffour, V. Jarlier, and S. Petrella. 2012. New mutations in the Mycobacterial ATP synthase: New insights into the binding of the diarylquinoline TMC207 to the ATP synthase C-ring structure. Antimicrob. Agents Chemother. 56:2326-2334.

Sendi, P., and Proctor, R. A. (2009) *Staphylococcus aureus* as an intracellular pathogen: the role of small colony variants. *Trends Microbiol* 17: 54-58.

Shah, P. M. (2005) The need for new therapeutic agents: what is the pipeline? *Clin Microbiol Infect* 11 Suppl 3: 36-42.

Sibley, C. D., Parkins, M. D., Rabin, H. R., and Surette, M. G. (2009) The relevance of the polymicrobial nature of airway infection in the acute and chronic management of patients with cystic fibrosis. *Curr Opin Investig Drugs* 10: 787-794.

Sibley, C. D., and Surette, M. G. (2011) The polymicrobial nature of airway infections in cystic fibrosis: Cangene Gold Medal Lecture. *Can J Microbiol* 57: 69-77.

Songer, J. G. (2010) Clostridia as agents of zoonotic disease. *Vet Microbiol* 140: 399-404.

Songer, J. G., and F. A. Uzal. 2005. Clostridial enteric infections in pigs. J. Vet. Diagn. Invest. 17:528-536.

Stepan, J., Pantucek, R., and Doskar, J. (2004) Molecular diagnostics of clinically important staphylococci. *Folia Microbiol (Praha)* 49: 353-386.

Stewart, P. S. (2002) Mechanisms of antibiotic resistance in bacterial biofilms. *Int J Med Microbiol* 292: 107-113.

Talbot, G. H., Bradley, J., Edwards, J. E., Jr., Gilbert, D., Scheld, M., and Bartlett, J. G. (2006) Bad bugs need drugs: an update on the development pipeline from the Antimicrobial Availability Task Force of the Infectious Diseases Society of America. *Clin Infect Dis* 42: 657-668.

Tenhagen, B. A., G. Koster, et al. (2006). "Prevalence of mastitis pathogens and their resistance against antimicrobial agents in dairy cows in Brandenburg, Germany." J Dairy Sci 89(7): 2542-51.

Tuchscherr, L., Medina, E., Hussain, M., Volker, W., Heitmann, V., Niemann, S., Holzinger, D., Roth, J., Proctor, R. A., Becker, K., Peters, G., and Loffler, B. (2011) *Staphylococcus aureus* phenotype switching: an effective bacterial strategy to escape host immune response and establish a chronic infection. *EMBO Mol Med* (in press).

Van Immerseel, F., J. De Buck, F. Pasmans, G. Huyghebaert, F. Haesebrouck, and R. Ducatelle. 2004. *Clostridium perfringens* in poultry: an emerging threat for animal and public health. *Avian Pathol.* 33:537-549.

Vergison, A., O. Denis, A. Deplano, G. Casimir, G. Claeys, F. DeBaets, K. DeBoeck, N. Douat, H. Franckx, J. Gigi, M. Ieven, C. Knoop, P. Lebeque, F. Lebrun, A. Malfroot, F. Paucquay, D. Pierard, J. Van Eldere and M. J. Struelens. 2007. National survey of molecular epidemiology of *Staphylococcus aureus* colonization in Belgian cystic fibrosis patients. *J. of Antimicrob Chemother.* 59:893-899.

Vial, L., Lepine, F., Milot, S., Groleau, M. C., Dekimpe, V., Woods, D. E., and Deziel, E. (2008) *Burkholderia pseudomallei, B. thailandensis*, and *B. ambifaria* produce 4-hydroxy-2-alkylquinoline analogues with a methyl group at the 3 position that is required for quorum-sensing regulation. J Bacteriol 190: 5339-5352.

Voggu, L., Schlag, S., Biswas, R., Rosenstein, R., Rausch, C., and Gotz, F. (2006) Microevolution of cytochrome bd oxidase in Staphylococci and its implication in resistance to respiratory toxins released by *Pseudomonas*. *J Bacteriol* 188: 8079-8086.

Vuong, C., and Otto, M. (2002) *Staphylococcus epidermidis* infections. *Microbes Infect* 4: 481-489.

Wellinghausen, N., Chatterjee, I., Berger, A., Niederfuehr, A., Proctor, R. A., and Kahl, B. C. (2009) Characterization of clinical *Enterococcus faecalis* small-colony variants. *J Clin Microbiol* 47: 2802-2811.

Witte, W., Cuny, C., Klare, I., Nubel, U., Strommenger, B., and Werner, G. (2008) Emergence and spread of antibiotic-resistant Gram-positive bacterial pathogens. *Int J Med Microbiol* 298: 365-377.

Wolter D J, Emerson J C, McNamara S, Buccat A M, Qin X, Cochrane E, Houston L S, Rogers G B, Marsh P, Prehar K, Pope C E, Blackledge M, Déziel E, Bruce K D, Ramsey B W, Gibson R L, Burns J L, Hoffman L R. 2013. *Staphylococcus aureus* small-colony variants are independently associated with worse lung disease in children with cystic fibrosis. Clin Infect Dis. 57(3):384-91. doi: 10.1093/cid/cit270. Epub April 26.

Xie W., Structure-activity relationship of Aza-steroids as PI-PLC inhibitors, Bioorganic & Medicinal Chemistry, 9 (2001) 1073-1083.

The invention claimed is:

1. A compound of formula (I):

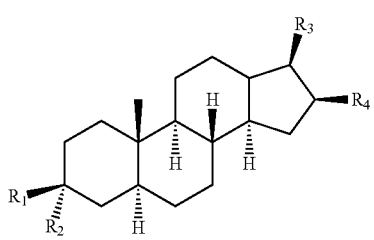

(I)

wherein:

R1 is H; and R2 is —NR5R6; or

R1 is —NR5R6; and R2 is H;

wherein R5 is H and R6 is —(CH$_2$)nNR7R8 or R6 is H and R5 is —(CH$_2$)nNR7R8, wherein n is 2-10; and R7 and R8 are identical or different and are selected from the group consisting of H, substituted or unsubstituted alkyl, substituted or unsubstituted aryl; substituted or unsubstituted cycloalkyl, and substituted or unsubstituted aralkyl;

wherein the substituted alkyl(s), substituted aryl(s), substituted aralkyl(s), substituted cycloalkyl(s), and substituted —(CH$_2$)nNR7R8 comprise(s) one or more identical or different substitutions selected from alkyl, aryl, cycloalkyl and aralkyl;

R3 and R4 form together with the carbon atoms to which they are attached form a spirocyclic structure of formula II:

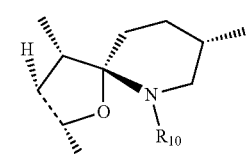

(II)

wherein R10 is H, substituted or unsubstituted alkyl, or substituted or unsubstituted —(CH$_2$)pNR13R14, wherein p is 2-10; and R13 and R14 are identical or different and are selected from the group consisting of H, substituted or unsubstituted alkyl, substituted or unsubstituted aryl, substituted or unsubstituted cycloalkyl, and substituted or unsubstituted aralkyl;

wherein substituted alkyl, substituted aryl, substituted aralkyl, substituted cycloalkyl, and substituted —(CH$_2$)pNR13R14 comprises one or more identical or different substitutions selected from alkyl, aryl, cycloalkyl and aralkyl, or a stereoisomer or mixture of stereoisomers or a salt thereof.

2. The compound of claim 1, wherein R10 is (i) H, or substituted or unsubstituted alkyl; (ii) H, or substituted or unsubstituted alkyl C1-C5; or (iii) H.

3. The compound of claim 1, wherein R7 and R8 are (i) identical or different and are selected from the group consisting of H and substituted or unsubstituted alkyl; (ii) identical or different and are selected from the group consisting of H and substituted or unsubstituted alkyl C1 to C3; or (iii) H.

4. The compound of claim 1, wherein n is (ii) 2 to 6; (iii) 2; (iii) 4; or (iv) 6.

5. The compound of claim 1, which is

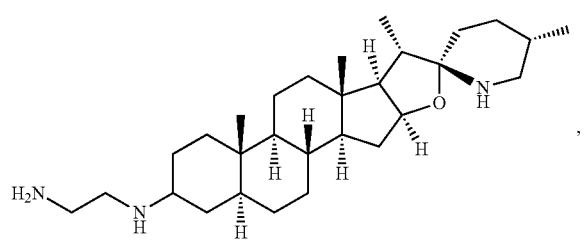

or a salt, stereoisomer or any mixture of stereoisomers of the compound.

6. The compound of claim 1, which is

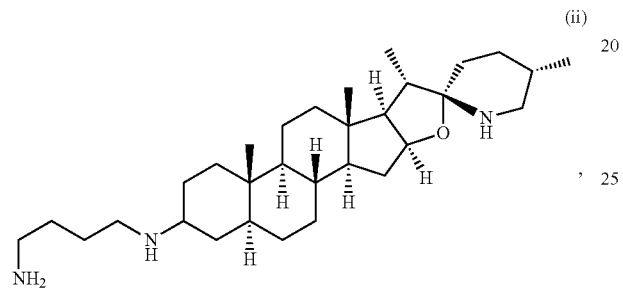

(ii)

or a salt, stereoisomer or any mixture of stereoisomers of the compound.

7. The compound of claim 1, which is

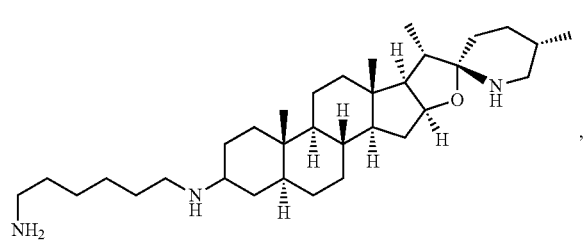

or a salt, stereoisomer or any mixture of stereoisomers of the compound.

8. A composition comprising (a) the compound as defined in claim 1, and
- (i) an antibiotic;
- (ii) an antiseptic;
- (iii) a disinfectant;
- (iv) a diluent;
- (v) an excipient;
- (vi) a pharmaceutically acceptable carrier; or
- (vii) any combination of (i)-(vi).

9. The composition of claim 8, comprising a compound which is

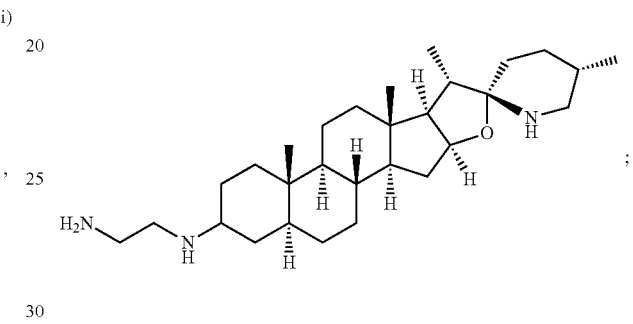

and a pharmaceutically acceptable carrier.

10. The composition of claim 9, further comprising an aminoglycoside antibiotic.

11. A kit comprising at least one of the compounds as defined in claim 1, and instructions to use same in (a) the prevention or treatment of a bacterial infection; or (b) the disinfection, sterilization and/or antisepsis of an object, further optionally comprising (i) an aminoglycoside antibiotic; (ii) an antiseptic; (iii) a disinfectant; (iv) a diluent; (v) an excipient; (vi) a pharmaceutically acceptable carrier; or (vii) any combination of (i)-(vi).

\* \* \* \* \*

SEQUENCE LISTING

```
<160> NUMBER OF SEQ ID NOS: 36

<210> SEQ ID NO 1
<211> LENGTH: 11
<212> TYPE: DNA
<213> ORGANISM: Staphylococcus aureus

<400> SEQUENCE: 1
taggagcagg t                                                           11

<210> SEQ ID NO 2
<211> LENGTH: 11
<212> TYPE: DNA
<213> ORGANISM: Staphylococcus aureus

<400> SEQUENCE: 2
taggatcagg t                                                           11

<210> SEQ ID NO 3
<211> LENGTH: 11
<212> TYPE: DNA
<213> ORGANISM: Staphylococcus aureus

<400> SEQUENCE: 3
aattgcattc a                                                           11

<210> SEQ ID NO 4
<211> LENGTH: 11
<212> TYPE: DNA
<213> ORGANISM: Staphylococcus aureus

<400> SEQUENCE: 4
aattacattc a                                                           11

<210> SEQ ID NO 5
<211> LENGTH: 70
<212> TYPE: PRT
<213> ORGANISM: Staphylococcus aureus

<400> SEQUENCE: 5

Met Asn Leu Ile Ala Ala Ala Ile Ala Ile Gly Leu Ser Ala Leu Gly
1               5                   10                  15

Ala Gly Ile Gly Asn Gly Leu Ile Val Ser Arg Thr Val Glu Gly Val
            20                  25                  30

Ala Arg Gln Pro Glu Ala Arg Gly Gln Leu Met Gly Ile Met Phe Ile
        35                  40                  45

Gly Val Gly Leu Val Glu Ala Leu Pro Ile Ile Gly Val Val Ile Ala
    50                  55                  60

Phe Met Thr Phe Ala Gly
```

-continued 65            70

<210> SEQ ID NO 6
<211> LENGTH: 72
<212> TYPE: PRT
<213> ORGANISM: Listeria monocytogenes

<400> SEQUENCE: 6

Met Ser Leu Gly Val Ile Ala Ala Ile Ala Val Gly Leu Gly Ala
1               5                   10                  15

Leu Gly Ala Gly Ile Gly Asn Gly Leu Ile Val Ser Lys Thr Val Glu
            20                  25                  30

Gly Val Ala Arg Gln Pro Glu Ala Arg Ser Met Leu Gln Thr Ile Met
        35                  40                  45

Phe Ile Gly Ile Gly Leu Val Glu Ala Leu Pro Ile Ile Ala Val Val
    50                  55                  60

Ile Ala Phe Met Val Leu Asn Lys
65              70

<210> SEQ ID NO 7
<211> LENGTH: 70
<212> TYPE: PRT
<213> ORGANISM: Bacillus subtilis

<400> SEQUENCE: 7

Met Asn Leu Ile Ala Ala Ala Ile Ala Ile Gly Leu Gly Ala Leu Gly
1               5                   10                  15

Ala Gly Ile Gly Asn Gly Leu Ile Val Ser Arg Thr Val Glu Gly Ile
            20                  25                  30

Ala Arg Gln Pro Glu Ala Gly Lys Glu Leu Arg Thr Leu Met Phe Met
        35                  40                  45

Gly Ile Ala Leu Val Glu Ala Leu Pro Ile Ile Ala Val Val Ile Ala
    50                  55                  60

Phe Leu Ala Phe Phe Gly
65              70

<210> SEQ ID NO 8
<211> LENGTH: 72
<212> TYPE: PRT
<213> ORGANISM: Bacillus cereus

<400> SEQUENCE: 8

Met Ser Leu Gly Val Ile Ala Ala Ile Ala Ile Gly Leu Ser Ala
1               5                   10                  15

Leu Gly Ala Gly Ile Gly Asn Gly Leu Ile Val Ser Arg Thr Ile Glu
            20                  25                  30

Gly Val Ala Arg Gln Pro Glu Leu Lys Gly Ala Leu Gln Thr Ile Met
        35                  40                  45

Phe Ile Gly Val Ala Leu Val Glu Ala Leu Pro Ile Ile Gly Val Val
    50                  55                  60

Ile Ala Phe Ile Val Met Asn Lys
65              70

<210> SEQ ID NO 9
<211> LENGTH: 72
<212> TYPE: PRT
<213> ORGANISM: Bacillus anthracis

<400> SEQUENCE: 9

```
Met Ser Leu Gly Val Ile Ala Ala Ala Ile Ala Gly Leu Ser Ala
1               5                  10                  15

Leu Gly Ala Gly Ile Gly Asn Gly Leu Ile Val Ser Arg Thr Ile Glu
            20                  25                  30

Gly Val Ala Arg Gln Pro Glu Leu Lys Gly Ala Leu Gln Thr Ile Met
            35                  40                  45

Phe Ile Gly Val Ala Leu Val Glu Ala Leu Pro Ile Ile Gly Val Val
        50                  55                  60

Ile Ala Phe Ile Val Met Asn Lys
65                  70
```

<210> SEQ ID NO 10
<211> LENGTH: 66
<212> TYPE: PRT
<213> ORGANISM: Streptococcus pneumoniae

<400> SEQUENCE: 10

```
Met Asn Leu Thr Phe Leu Gly Leu Cys Ile Ala Cys Met Gly Val Ser
1               5                   10                  15

Val Gly Glu Gly Leu Leu Met Asn Gly Leu Phe Lys Ser Val Ala Arg
            20                  25                  30

Gln Pro Asp Met Leu Ser Glu Phe Arg Ser Leu Met Phe Leu Gly Val
            35                  40                  45

Ala Phe Ile Glu Gly Thr Phe Phe Val Thr Leu Val Phe Ser Phe Ile
        50                  55                  60

Ile Lys
65
```

<210> SEQ ID NO 11
<211> LENGTH: 79
<212> TYPE: PRT
<213> ORGANISM: Escherichia coli

<400> SEQUENCE: 11

```
Met Glu Asn Leu Asn Met Asp Leu Leu Tyr Met Ala Ala Ala Val Met
1               5                   10                  15

Met Gly Leu Ala Ala Ile Gly Ala Ala Ile Gly Ile Gly Ile Leu Gly
            20                  25                  30

Gly Lys Phe Leu Glu Gly Ala Ala Arg Gln Pro Asp Leu Ile Pro Leu
            35                  40                  45

Leu Arg Thr Gln Phe Phe Ile Val Met Gly Leu Val Asp Ala Ile Pro
        50                  55                  60

Met Ile Ala Val Gly Leu Gly Leu Tyr Val Met Phe Ala Val Ala
65                  70                  75
```

<210> SEQ ID NO 12
<211> LENGTH: 86
<212> TYPE: PRT
<213> ORGANISM: Mycobacterium smegmatis

<400> SEQUENCE: 12

```
Met Asp Leu Asp Pro Asn Ala Ile Ile Thr Ala Gly Ala Leu Ile Gly
1               5                   10                  15

Gly Gly Leu Ile Met Gly Gly Gly Ala Ile Gly Ala Gly Ile Gly Asp
            20                  25                  30

Gly Ile Ala Gly Asn Ala Leu Ile Ser Gly Ile Ala Arg Gln Pro Glu
            35                  40                  45

Ala Gln Gly Arg Leu Phe Thr Pro Phe Phe Ile Thr Val Gly Leu Val
```

```
                50                 55                 60
Glu Ala Ala Tyr Phe Ile Asn Leu Ala Phe Met Ala Leu Phe Val Phe
 65                 70                 75                 80

Ala Thr Pro Gly Leu Gln
                 85

<210> SEQ ID NO 13
<211> LENGTH: 142
<212> TYPE: PRT
<213> ORGANISM: Homo sapiens

<400> SEQUENCE: 13

Met Phe Ala Cys Ala Lys Leu Ala Cys Thr Pro Ser Leu Ile Arg Ala
 1               5                  10                  15

Gly Ser Arg Val Ala Tyr Arg Pro Ile Ser Ala Ser Val Leu Ser Arg
                20                 25                  30

Pro Glu Ala Ser Arg Thr Gly Glu Gly Ser Thr Val Phe Asn Gly Ala
             35                  40                  45

Gln Asn Gly Val Ser Gln Leu Ile Gln Arg Glu Phe Gln Thr Ser Ala
         50                  55                  60

Ile Ser Arg Asp Ile Asp Thr Ala Ala Lys Phe Ile Gly Ala Gly Ala
 65                 70                  75                  80

Ala Thr Val Gly Val Ala Gly Ser Gly Ala Gly Ile Gly Thr Val Phe
                85                  90                  95

Gly Ser Leu Ile Ile Gly Tyr Ala Arg Asn Pro Ser Leu Lys Gln Gln
               100                 105                 110

Leu Phe Ser Tyr Ala Ile Leu Gly Phe Ala Leu Ser Glu Ala Met Gly
           115                 120                 125

Leu Phe Cys Leu Met Val Ala Phe Leu Ile Leu Phe Ala Met
       130                 135                 140

<210> SEQ ID NO 14
<211> LENGTH: 72
<212> TYPE: PRT
<213> ORGANISM: Listeria ivanovii

<400> SEQUENCE: 14

Met Ser Leu Gly Val Ile Ala Ala Ala Ile Ala Val Gly Leu Gly Ala
 1               5                  10                  15

Leu Gly Ala Gly Ile Gly Asn Gly Leu Ile Val Ser Lys Thr Val Glu
                20                  25                  30

Gly Val Ala Arg Gln Pro Glu Ala Arg Ser Met Leu Gln Ser Ile Met
             35                  40                  45

Phe Val Gly Val Ala Leu Val Glu Ala Leu Pro Ile Ile Ala Val Val
         50                  55                  60

Ile Ala Phe Met Val Leu Asn Lys
 65                 70

<210> SEQ ID NO 15
<211> LENGTH: 70
<212> TYPE: PRT
<213> ORGANISM: Staphylococcus haemolyticus

<400> SEQUENCE: 15

Met Gly Leu Ile Ala Ala Ala Ile Ala Ile Gly Leu Ser Ala Leu Gly
 1               5                  10                  15

Ala Gly Ile Gly Asn Gly Leu Ile Val Ser Arg Thr Val Glu Gly Val
                20                  25                  30
```

Ala Arg Gln Pro Glu Ala Arg Gly Gln Leu Met Ser Ile Met Phe Ile
            35                  40                  45

Gly Ile Gly Leu Val Glu Ala Leu Pro Ile Ile Gly Val Val Ile Ala
        50                  55                  60

Phe Met Thr Leu Phe Gln
65                  70

<210> SEQ ID NO 16
<211> LENGTH: 70
<212> TYPE: PRT
<213> ORGANISM: Staphylococcus lugdunensis

<400> SEQUENCE: 16

Met Gly Leu Ile Ala Ala Ala Ile Ala Ile Gly Leu Ser Ala Leu Gly
1               5                   10                  15

Ala Gly Ile Gly Asn Gly Leu Ile Val Ser Arg Thr Val Glu Gly Val
            20                  25                  30

Ala Arg Gln Pro Glu Ala Arg Gly Gln Leu Met Ser Ile Met Phe Ile
            35                  40                  45

Gly Ile Gly Leu Val Glu Ala Leu Pro Ile Ile Gly Val Val Ile Ala
        50                  55                  60

Phe Met Thr Leu Phe Arg
65                  70

<210> SEQ ID NO 17
<211> LENGTH: 70
<212> TYPE: PRT
<213> ORGANISM: Staphylococcus epidermidis

<400> SEQUENCE: 17

Met Asn Leu Ile Ala Ala Ala Ile Ala Ile Gly Leu Ser Ala Leu Gly
1               5                   10                  15

Ala Gly Ile Gly Asn Gly Leu Ile Val Ser Arg Thr Val Glu Gly Val
            20                  25                  30

Ala Arg Gln Pro Glu Ala Arg Gly Gln Leu Met Gly Ile Met Phe Ile
            35                  40                  45

Gly Val Gly Leu Val Glu Ala Leu Pro Ile Ile Gly Val Val Ile Ala
        50                  55                  60

Phe Met Thr Phe Ala Gly
65                  70

<210> SEQ ID NO 18
<211> LENGTH: 70
<212> TYPE: PRT
<213> ORGANISM: Staphylococcus pasteuri

<400> SEQUENCE: 18

Met Asn Leu Ile Ala Ala Ala Ile Ala Ile Gly Leu Ser Ala Leu Gly
1               5                   10                  15

Ala Gly Ile Gly Asn Gly Leu Ile Val Ser Arg Thr Val Glu Gly Val
            20                  25                  30

Ala Arg Gln Pro Glu Ala Arg Gly Gln Leu Met Gly Ile Met Phe Ile
            35                  40                  45

Gly Val Gly Leu Val Glu Ala Leu Pro Ile Ile Gly Val Val Ile Ala
        50                  55                  60

Phe Met Thr Phe Ala Gly
65                  70

<210> SEQ ID NO 19
<211> LENGTH: 70
<212> TYPE: PRT
<213> ORGANISM: Staphylococcus warneri

<400> SEQUENCE: 19

Met Asn Leu Ile Ala Ala Ala Ile Ala Ile Gly Leu Ser Ala Leu Gly
1               5                   10                  15

Ala Gly Ile Gly Asn Gly Leu Ile Val Ser Arg Thr Val Glu Gly Val
            20                  25                  30

Ala Arg Gln Pro Glu Ala Arg Gly Gln Leu Met Gly Ile Met Phe Ile
        35                  40                  45

Gly Val Gly Leu Val Glu Ala Leu Pro Ile Ile Gly Val Val Ile Ala
    50                  55                  60

Phe Met Thr Phe Ala Gly
65                  70

<210> SEQ ID NO 20
<211> LENGTH: 68
<212> TYPE: PRT
<213> ORGANISM: Staphylococcus saprophyticus

<400> SEQUENCE: 20

Met Asn Leu Ile Ala Ala Ala Ile Ala Ile Gly Leu Ser Ala Leu Gly
1               5                   10                  15

Ala Gly Ile Gly Asn Gly Leu Ile Val Ser Arg Thr Val Glu Gly Val
            20                  25                  30

Ala Arg Gln Pro Glu Ala Arg Gly Gln Leu Met Gly Ile Met Phe Ile
        35                  40                  45

Gly Ile Gly Leu Val Glu Ala Leu Pro Ile Ile Gly Val Val Ile Ala
    50                  55                  60

Phe Met Ser Leu
65

<210> SEQ ID NO 21
<211> LENGTH: 72
<212> TYPE: PRT
<213> ORGANISM: Bacillus coagulans

<400> SEQUENCE: 21

Met Ser Leu Gly Ile Leu Ala Ala Ala Ile Ala Val Gly Leu Ala Ala
1               5                   10                  15

Leu Gly Ala Gly Ile Gly Asn Gly Leu Ile Val Gly Arg Thr Val Glu
            20                  25                  30

Gly Ile Ala Arg Gln Pro Glu Ala Arg Gly Leu Leu Gln Thr Thr Met
        35                  40                  45

Phe Ile Gly Ile Gly Leu Val Glu Ala Leu Pro Ile Ile Ala Val Val
    50                  55                  60

Ile Ala Phe Ile Ala Leu Gly Arg
65                  70

<210> SEQ ID NO 22
<211> LENGTH: 72
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)

```
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(43)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (68)..(72)
<223> OTHER INFORMATION: Xaa can be any naturally occurring amino acid

<400> SEQUENCE: 22

Met Xaa Leu Xaa Xaa Xaa Ala Ala Ala Ile Ala Xaa Gly Leu Xaa Ala
1               5                   10                  15

Leu Gly Ala Gly Ile Gly Asn Gly Leu Ile Val Xaa Xaa Thr Xaa Glu
                20                  25                  30

Gly Xaa Ala Arg Gln Pro Glu Xaa Xaa Xaa Leu Xaa Xaa Xaa Xaa Met
            35                  40                  45

Phe Xaa Gly Xaa Xaa Leu Val Glu Ala Leu Pro Ile Ile Xaa Val Val
    50                  55                  60

Ile Ala Phe Xaa Xaa Xaa Xaa Xaa
65                  70

<210> SEQ ID NO 23
<211> LENGTH: 72
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
```

```
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(43)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (68)..(72)
<223> OTHER INFORMATION: Xaa can be any naturally occurring amino acid

<400> SEQUENCE: 23

Met Xaa Leu Xaa Xaa Ile Ala Ala Ala Ile Ala Xaa Gly Leu Xaa Ala
1               5                   10                  15

Leu Gly Ala Gly Ile Gly Asn Gly Leu Ile Val Ser Xaa Thr Xaa Glu
            20                  25                  30

Gly Xaa Ala Arg Gln Pro Glu Xaa Xaa Xaa Xaa Leu Xaa Xaa Xaa Met
        35                  40                  45

Phe Xaa Gly Xaa Xaa Leu Val Glu Ala Leu Pro Ile Ile Xaa Val Val
    50                  55                  60

Ile Ala Phe Xaa Xaa Xaa Xaa Xaa
65                  70

<210> SEQ ID NO 24
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (10)..(10)
```

```
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 24

Leu Xaa Xaa Xaa Ala Ala Ala Ile Ala Xaa Gly Leu Xaa Ala Leu Gly
1               5                   10                  15

Ala Gly Ile Gly Asn Gly Leu Ile Val Xaa Xaa Thr Xaa Glu Gly Xaa
            20                  25                  30

Ala Arg Gln Pro Glu Xaa
        35

<210> SEQ ID NO 25
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa is any aliphatic amino acid residue or
      absent
<220> FEATURE:
<221> NAME/KEY: misc_feature
<222> LOCATION: (4)..(4)
<223> OTHER INFORMATION: Xaa is any aliphatic amino acid residue
<220> FEATURE:
<221> NAME/KEY: misc_feature
<222> LOCATION: (10)..(10)
<223> OTHER INFORMATION: Xaa is any aliphatic amino acid residue
<220> FEATURE:
<221> NAME/KEY: misc_feature
<222> LOCATION: (13)..(13)
<223> OTHER INFORMATION: Xaa is any aliphatic or hydroxyl- or sulfur-
      containing amino acid residue
<220> FEATURE:
<221> NAME/KEY: misc_feature
<222> LOCATION: (26)..(26)
<223> OTHER INFORMATION: Xaa is any aliphatic or hydroxyl- or sulfur-
      containing amino acid residue
<220> FEATURE:
<221> NAME/KEY: misc_feature
<222> LOCATION: (27)..(27)
<223> OTHER INFORMATION: Xaa is any basic amino acid residue
<220> FEATURE:
<221> NAME/KEY: misc_feature
<222> LOCATION: (29)..(29)
<223> OTHER INFORMATION: Xaa is any aliphatic amino acid residue
<220> FEATURE:
<221> NAME/KEY: misc_feature
<222> LOCATION: (32)..(32)
<223> OTHER INFORMATION: Xaa is any aliphatic amino acid residue
<220> FEATURE:
<221> NAME/KEY: MISC_FEATURE
<222> LOCATION: (38)..(38)
<223> OTHER INFORMATION: Xaa is any aliphatic amino acid residue
```

<400> SEQUENCE: 25

```
Leu Xaa Xaa Xaa Ala Ala Ala Ile Ala Xaa Gly Leu Xaa Ala Leu Gly
1               5                   10                  15

Ala Gly Ile Gly Asn Gly Leu Ile Val Xaa Xaa Thr Xaa Glu Gly Xaa
            20                  25                  30

Ala Arg Gln Pro Glu Xaa
        35
```

<210> SEQ ID NO 26
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is glycine or absent
<220> FEATURE:
<221> NAME/KEY: misc_feature
<222> LOCATION: (3)..(3)
<223> OTHER INFORMATION: Xaa is valine or absent
<220> FEATURE:
<221> NAME/KEY: misc_feature
<222> LOCATION: (4)..(4)
<223> OTHER INFORMATION: Xaa is isoleucine or leucine
<220> FEATURE:
<221> NAME/KEY: misc_feature
<222> LOCATION: (10)..(10)
<223> OTHER INFORMATION: Xaa is valine or isoleucine
<220> FEATURE:
<221> NAME/KEY: misc_feature
<222> LOCATION: (13)..(13)
<223> OTHER INFORMATION: Xaa is glycine, serine or alanine
<220> FEATURE:
<221> NAME/KEY: misc_feature
<222> LOCATION: (26)..(26)
<223> OTHER INFORMATION: Xaa is serine or glycine
<220> FEATURE:
<221> NAME/KEY: misc_feature
<222> LOCATION: (27)..(27)
<223> OTHER INFORMATION: Xaa is lysine or arginine
<220> FEATURE:
<221> NAME/KEY: misc_feature
<222> LOCATION: (29)..(29)
<223> OTHER INFORMATION: Xaa is valine or isoleucine
<220> FEATURE:
<221> NAME/KEY: misc_feature
<222> LOCATION: (32)..(32)
<223> OTHER INFORMATION: Xaa is valine or isoleucine
<220> FEATURE:
<221> NAME/KEY: misc_feature
<222> LOCATION: (38)..(38)
<223> OTHER INFORMATION: Xaa is alanine or leucine

<400> SEQUENCE: 26

```
Leu Xaa Xaa Xaa Ala Ala Ala Ile Ala Xaa Gly Leu Xaa Ala Leu Gly
1               5                   10                  15

Ala Gly Ile Gly Asn Gly Leu Ile Val Xaa Xaa Thr Xaa Glu Gly Xaa
            20                  25                  30

Ala Arg Gln Pro Glu Xaa
        35
```

<210> SEQ ID NO 27
<211> LENGTH: 38
<212> TYPE: PRT
<213> ORGANISM: Artificial sequence
<220> FEATURE:
<223> OTHER INFORMATION: Synthetic sequence
<220> FEATURE:

```
<221> NAME/KEY: misc_feature
<222> LOCATION: (2)..(3)
<223> OTHER INFORMATION: Xaa can be any naturally occurring amino acid
<220> FEATURE:
<221

```
Leu Xaa Xaa Ile Ala Ala Ala Ile Ala Xaa Gly Leu Xaa Ala Leu Gly
1               5                   10                  15

Ala Gly Ile Gly Asn Gly Leu Ile Val Ser Xaa Thr Xaa Glu Gly Xaa
            20                  25                  30

Ala Arg Gln Pro Glu Xaa
        35

<210> SEQ ID NO 29
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is glycine or absent
<220> FEATURE:
<221> NAME/KEY: misc_feature
<222> LOCATION: (3)..(3)
<223> OTHER INFORMATION: Xaa is valine or absent
<220> FEATURE:
<221> NAME/KEY: misc_feature
<222> LOCATION: (10)..(10)
<223> OTHER INFORMATION: Xaa is valine or isoleucine
<220> FEATURE:
<221> NAME/KEY: misc_feature
<222> LOCATION: (13)..(13)
<223> OTHER INFORMATION: Xaa is glycine or serine
<220> FEATURE:
<221> NAME/KEY: misc_feature
<222> LOCATION: (27)..(27)
<223> OTHER INFORMATION: Xaa is lysine or arginine
<220> FEATURE:
<221> NAME/KEY: misc_feature
<222> LOCATION: (29)..(29)
<223> OTHER INFORMATION: Xaa is valine or isoleucine
<220> FEATURE:
<221> NAME/KEY: misc_feature
<222> LOCATION: (32)..(32)
<223> OTHER INFORMATION: Xaa is valine or isoleucine
<220> FEATURE:
<221> NAME/KEY: misc_feature
<222> LOCATION: (38)..(38)
<223> OTHER INFORMATION: Xaa is alanine or leucine

<400> SEQUENCE: 29

Leu Xaa Xaa Ile Ala Ala Ala Ile Ala Xaa Gly Leu Xaa Ala Leu Gly
1               5                   10                  15

Ala Gly Ile Gly Asn Gly Leu Ile Val Ser Xaa Thr Xaa Glu Gly Xaa
            20                  25                  30

Ala Arg Gln Pro Glu Xaa
        35

<210> SEQ ID NO 30
<211> LENGTH: 17
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 30

Gly Xaa Xaa Leu Val Glu Ala Leu Pro Ile Ile Xaa Val Val Ile Ala
```

```
1               5                   10                  15

Phe

<210> SEQ ID NO 31
<211> LENGTH: 17
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa is any aliphatic amino acid residue
<220> FEATURE:
<221> NAME/KEY: misc_feature
<222> LOCATION: (12)..(12)
<223> OTHER INFORMATION: Xaa is any aliphatic amino acid residue

<400> SEQUENCE: 31

Gly Xaa Xaa Leu Val Glu Ala Leu Pro Ile Ile Xaa Val Val Ile Ala
1               5                   10                  15

Phe

<210> SEQ ID NO 32
<211> LENGTH: 17
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa is valine or isoleucine
<220> FEATURE:
<221> NAME/KEY: misc_feature
<222> LOCATION: (3)..(3)
<223> OTHER INFORMATION: Xaa is glycine or alanine
<220> FEATURE:
<221> NAME/KEY: misc_feature
<222> LOCATION: (12)..(12)
<223> OTHER INFORMATION: Xaa is glycine or alanine

<400> SEQUENCE: 32

Gly Xaa Xaa Leu Val Glu Ala Leu Pro Ile Ile Xaa Val Val Ile Ala
1               5                   10                  15

Phe

<210> SEQ ID NO 33
<211> LENGTH: 7
<212> TYPE: PRT
<213> ORGANISM: Artificial sequence
<220> FEATURE:
<223> OTHER INFORMATION: Synthetic sequence

<400> SEQUENCE: 33

Ala Leu Gly Ala Gly Ile Gly
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic sequence

<400> SEQUENCE: 34

Leu Gly Ala Gly Ile
1               5
```

```
<210> SEQ ID NO 35
<211> LENGTH: 5
<212> TYPE: PRT
<213> ORGANISM: Artificial sequence
<220> FEATURE:
<223> OTHER INFORMATION: Synthetic sequence

<400> SEQUENCE: 35

Ala Leu Gly Ala Gly
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic sequence

<400> SEQUENCE: 36

Gly Ala Gly Ile Gly
1               5
```